United States Patent
Shin et al.

(10) Patent No.: US 12,035,617 B2
(45) Date of Patent: Jul. 9, 2024

(54) ORGANIC ELECTROLUMINESCENCE DEVICE AND ORGANOMETALLIC COMPOUND FOR ORGANIC ELECTROLUMINESCENCE DEVICE

(71) Applicant: Samsung Display Co., Ltd., Yongin-si (KR)

(72) Inventors: Hyun Shin, Hwaseong-si (KR); Sunwoo Kang, Hwaseong-si (KR); Jaejin Lyu, Gwangju-si (KR); Yoonkyoo Lee, Seoul (KR); Jin-Won Sun, Seoul (KR); Jungsub Lee, Yongin-si (KR)

(73) Assignee: Samsung Display Co., Ltd., Yongin-si (KR)

( * ) Notice: Subject to any disclaimer, the term of this patent is extended or adjusted under 35 U.S.C. 154(b) by 673 days.

(21) Appl. No.: 17/246,691

(22) Filed: May 2, 2021

(65) Prior Publication Data

US 2021/0359227 A1    Nov. 18, 2021

(30) Foreign Application Priority Data

May 18, 2020   (KR) .................. 10-2020-0058817

(51) Int. Cl.
  *H01L 51/50*   (2006.01)
  *C07D 209/88*   (2006.01)
  (Continued)

(52) U.S. Cl.
  CPC ......... *H10K 85/346* (2023.02); *C07D 209/88* (2013.01); *C07D 405/10* (2013.01); *C07F 7/0812* (2013.01); *C07F 15/0086* (2013.01); *C09K 11/06* (2013.01); *H10K 85/40* (2023.02); *H10K 85/6572* (2023.02); *H10K 85/6574* (2023.02); *C07B 2200/05* (2013.01); *C09K 2211/1018* (2013.01); *C09K 2211/1044* (2013.01); *C09K 2211/185* (2013.01); *H10K 50/11* (2023.02); *H10K 50/15* (2023.02); *H10K 50/16* (2023.02); *H10K 50/17* (2023.02);
  (Continued)

(58) Field of Classification Search
  None
  See application file for complete search history.

(56) References Cited

U.S. PATENT DOCUMENTS

| 9,093,650 B2 | 7/2015 | Kim et al. |
| 9,550,801 B2 | 1/2017 | Li et al. |

(Continued)

FOREIGN PATENT DOCUMENTS

| KR | 10-1659104 | 9/2016 |
| KR | 10-2018-0126655 | 11/2018 |

(Continued)

*Primary Examiner* — Gregory D Clark
(74) *Attorney, Agent, or Firm* — Lewis Roca Rothgerber Christie LLP

(57) ABSTRACT

An organic electroluminescence device includes: a first electrode; a second electrode facing the first electrode; and a plurality of organic layers disposed between the first electrode and the second electrode, wherein at least one organic layer of the plurality of organic layers includes a first compound represented by Formula 1, a second compound represented by Formula 2, and a third compound represented by Formula 3, wherein Formulae 1-3 are defined herein.

20 Claims, 3 Drawing Sheets

(51) Int. Cl.
  *C07D 405/10* (2006.01)
  *C07F 7/08* (2006.01)
  *C07F 15/00* (2006.01)
  *C09K 11/06* (2006.01)
  *H10K 85/30* (2023.01)
  *H10K 85/40* (2023.01)
  *H10K 85/60* (2023.01)
  *H10K 50/11* (2023.01)
  *H10K 50/15* (2023.01)
  *H10K 50/16* (2023.01)
  *H10K 50/17* (2023.01)
  *H10K 50/18* (2023.01)
  *H10K 101/00* (2023.01)
  *H10K 101/10* (2023.01)

(52) U.S. Cl.
  CPC ........... *H10K 50/171* (2023.02); *H10K 50/18* (2023.02); *H10K 85/654* (2023.02); *H10K 2101/10* (2023.02); *H10K 2101/90* (2023.02)

(56) References Cited

U.S. PATENT DOCUMENTS

| | | |
|---|---|---|
| 10,326,111 B2 | 6/2019 | Yoo et al. |
| 2011/0227058 A1 | 9/2011 | Masui et al. |
| 2015/0105556 A1* | 4/2015 | Li .................. C09K 11/06 546/4 |
| 2017/0018600 A1 | 1/2017 | Ito et al. |
| 2017/0200899 A1 | 7/2017 | Kim et al. |
| 2018/0337361 A1 | 11/2018 | Lee et al. |
| 2019/0225636 A1 | 7/2019 | Bae et al. |
| 2019/0280222 A1 | 9/2019 | Kim et al. |

FOREIGN PATENT DOCUMENTS

| | | |
|---|---|---|
| KR | 10-2019-0089626 | 7/2019 |
| KR | 10-2019-0107264 | 9/2019 |

* cited by examiner

ORGANIC ELECTROLUMINESCENCE DEVICE AND ORGANOMETALLIC COMPOUND FOR ORGANIC ELECTROLUMINESCENCE DEVICE

CROSS-REFERENCE TO RELATED APPLICATION

This application claims priority from and the benefit of Korean Patent Application No. 10-2020-0058817, filed on May 18, 2020, which is hereby incorporated by reference for all purposes as if fully set forth herein.

BACKGROUND

Field

Exemplary implementations of the invention relate generally to an organic electroluminescence device and, more particularly, to an organometallic compound used therein.

Discussion of the Background

Recently, the use of an organic electroluminescence display as an image display device is being actively developed. The organic electroluminescence display is so-called a self-luminescent display in which holes and electrons injected from a first electrode and a second electrode recombine in an emission layer to generate excitons, and the generated excitons fall to the ground state and emits light to implement display.

In the application of an organic electroluminescence device to a display, development of an organometallic compound used as a dopant material of an emission layer material is ongoing.

The above information disclosed in this Background section is only for understanding of the background of the inventive concepts, and, therefore, it may contain information that does not constitute prior art.

SUMMARY

There is a need for continued development of an organometallic compound for use in an organic electroluminescence device having an optimal emission wavelength and a long life time.

Organic electroluminescence devices having organometallic compounds made according to principles and exemplary implementations of the invention have an increased life time.

Additional features of the inventive concepts will be set forth in the description which follows, and in part will be apparent from the description, or may be learned by practice of the inventive concepts.

According to one aspect of the invention, an organic electroluminescence device includes: a first electrode; a second electrode facing the first electrode; and a plurality of organic layers disposed between the first electrode and the second electrode, wherein at least one organic layer of the plurality of organic layers includes a first compound represented by Formula 1, a second compound represented by Formula 2, and a third compound represented by Formula 3:

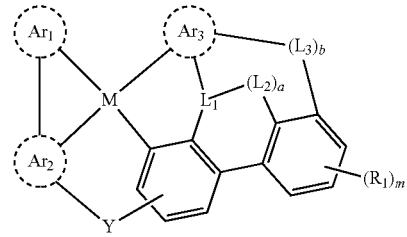

Formula 1 wherein, in Formula 1,

M is Pt, Au, Pd, Cu, or Ag,

Y is O or S, $Ar_1$, $Ar_2$, and $Ar_3$ are each, independently from one another, a substituted or unsubstituted aromatic hydrocarbon group of 6 to 30 ring-forming carbon atoms, or a substituted or unsubstituted aromatic heterocycle of 2 to 30 ring-forming carbon atoms, and $Ar_1$ includes, as a substituent, an aryl group substituted with at least one of a hydrogen atom, a deuterium atom, a substituted or unsubstituted alkyl group, a cyano group, a substituted or unsubstituted aryl group, a substituted or unsubstituted alkyl group, and a substituted borazine group, $L_1$ is a direct linkage or N, $L_2$ is a direct linkage, $L_3$ is a substituted or unsubstituted alkylene group having 1 to 30 carbon atoms, a is 0 or 1, b is an integer of 0 to 2, $R_1$ is a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, and m is an integer of 0 to 4,

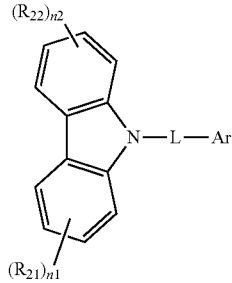

Formula 2 wherein, in Formula 2,

Ar is a substituted or unsubstituted silyl group, a substituted or unsubstituted aryl group of 6 to 30 ring-forming carbon atoms, or a substituted or unsubstituted heteroaryl group of 3 to 30 ring-forming carbon atoms, L is a direct linkage, a substituted or unsubstituted arylene group having 6 to 30 ring-forming carbon atoms, or a substituted or unsubstituted heteroarylene group having 3 to 30 ring-forming carbon atoms, $R_{21}$ and $R_{22}$ are each, independently from one another, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and n1 and n2 are each, independently from one another, an integer of 0 to 4,

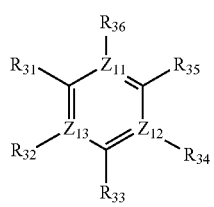

Formula 3 wherein, in Formula 3, $R_{31}$, $R_{32}$, $R_{33}$, $R_{34}$, $R_{35}$, and $R_{36}$ are each, independently from one another, a hydrogen atom, a deuterium atom, a cyano group, a substituted silyl group, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and $Z_{11}$, $Z_{12}$, and $Z_{13}$ are each, independently from one another, C or N.

The first compound may be represented by Formula 1-1a or Formula 1-1b:

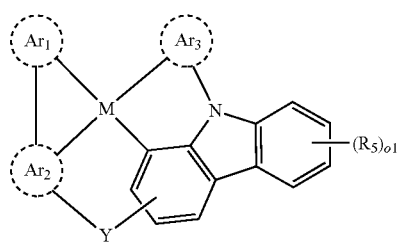

Formula 1-1a

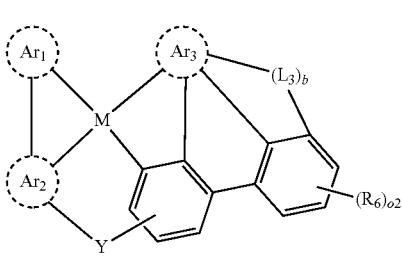

Formula 1-1b wherein, in Formula 1-1a and Formula 1-1b, the variables are defined herein.

The first compound may be represented by Formula 1-2a or Formula 1-2b:

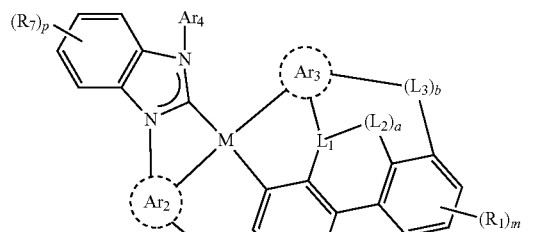

Formula 1-2a

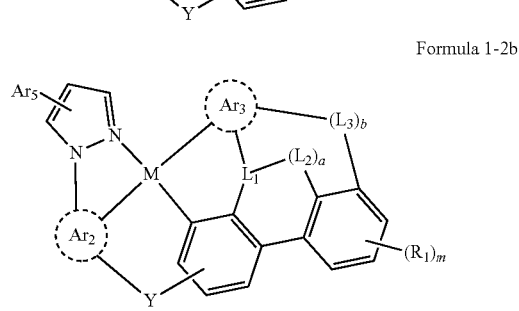

Formula 1-2b wherein, in Formula 1-2a and 1-2b, the variables are defined herein.

The first compound may be represented by Formula 1-3a or Formula 1-3b:

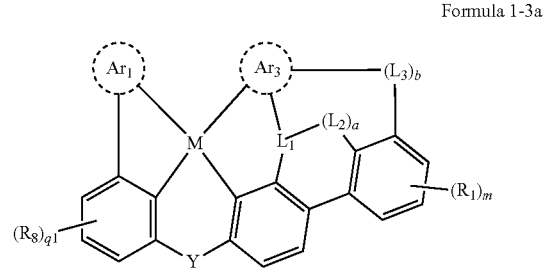

Formula 1-3a

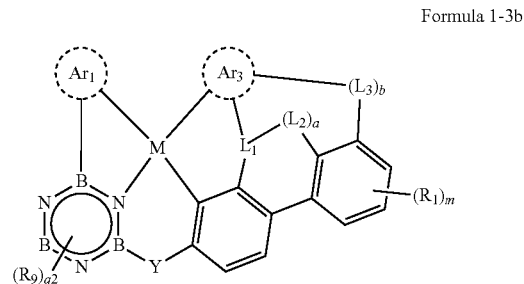

Formula 1-3b wherein, in Formula 1-3a and Formula 1-3b, wherein the variables are defined herein.

The first compound may be represented by Formula 1-4a or Formula 1-4b:

Formula 1-4a

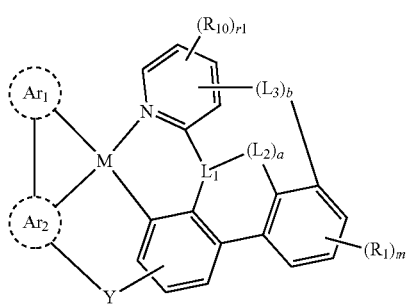

Formula 1-4b

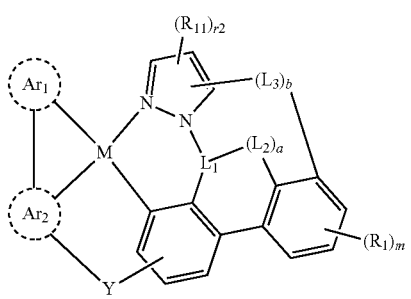

wherein, in Formula 1-4a and Formula 1-4b, wherein the variables are defined herein.

The first compound may be represented by Formula 1-5:

Formula 1-5

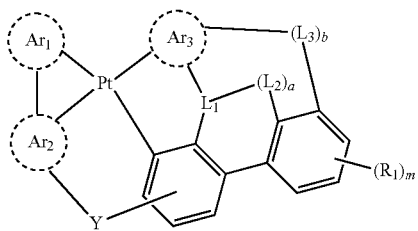

wherein, in Formula 1-5, wherein the variables are defined herein.

The first compound may be represented by Formula 1-6:

Formula 1-6

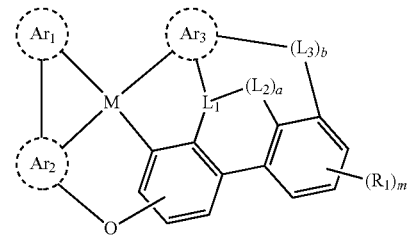

wherein, in Formula 1-6, wherein the variables are defined herein.

The first compound may be represented by either Formula 1-7a or Formula 1-7b:

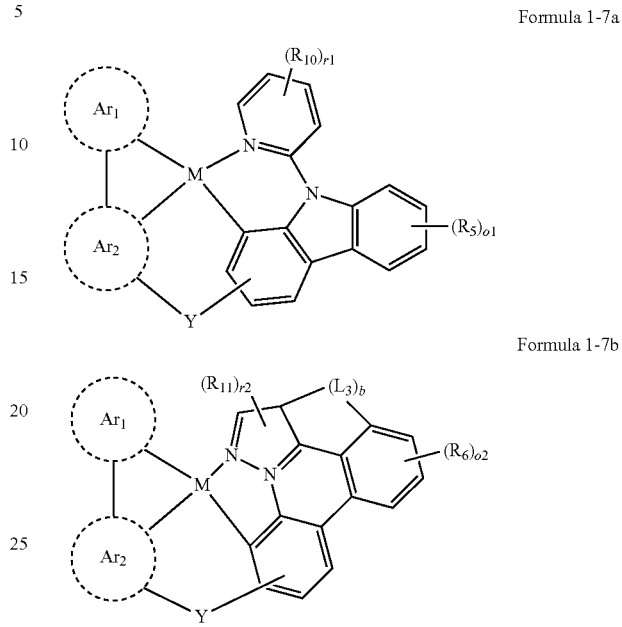

wherein, in Formula 1-7a and Formula 1-7b, wherein the variables are defined herein.

The organic layers may include a hole transport region, an emission layer, and an electron transport region, and the emission layer may include the first to third compounds.

The emission layer may be configured to emit phosphorescence.

The emission layer may include a host and a dopant, and the dopant may include the first compound.

The hole transport region may include a hole injection layer, a hole transport layer, an electron blocking layer, and a hole barrier reinforced layer, and the electron transport region may include an electron injection layer, an electron transport layer, a hole blocking layer, and an electron The first compound may include at least one compound represented by Compound Group 1, wherein the variables are defined herein.

The second compound may include at least one compound represented by Compound Group H1, wherein the variables are defined herein.

The third compound may include at least one compound represented by Compound Group H2, wherein the variables are defined herein.

According to another aspect of the invention, an organic electroluminescence device includes: a first electrode; a second electrode facing the first electrode; and a plurality of organic layers disposed between the first electrode and the second electrode, wherein at least one organic layer of the organic layers includes a first compound represented by Formula A or Formula B, a second compound represented by Formula 2, and a third compound represented by Formula 3:

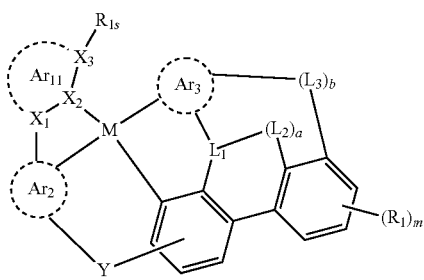

Formula A

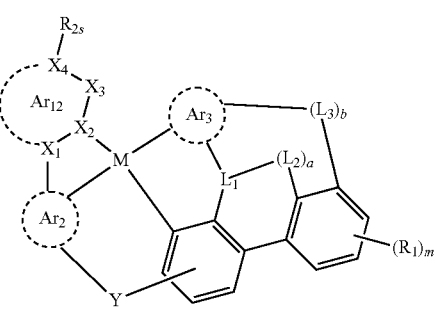

Formula B wherein, in Formula A and Formula B,

M is Pt, Au, Pd, Cu, or Ag, $Ar_{11}$, $Ar_{12}$, $Ar_2$, and $Ar_3$ are each, independently from one another, a substituted or unsubstituted aromatic hydrocarbon group of 6 to 30 ring-forming carbon atoms, or a substituted or unsubstituted aromatic heterocycle of 2 to 30 ring-forming carbon atoms, $X_1$, $X_2$, $X_3$, and $X_4$ are each, independently from one another, N or C, Y is O or S, $R_{1s}$ and $R_{2s}$ are each, independently from one another, an aryl group substituted with at least one of a hydrogen atom, a deuterium atom, a substituted or unsubstituted alkyl group, a cyano group, a substituted or unsubstituted aryl group, a substituted or unsubstituted alkyl group, and a substituted borazine group, $L_1$ is a direct linkage or N, $L_2$ is a direct linkage, $L_3$ is a substituted or unsubstituted alkylene group having 1 to 30 carbon atoms, a is 0 or 1, b is an integer of 0 to 2, $R_1$ is a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, and m is an integer of 0 to 4,

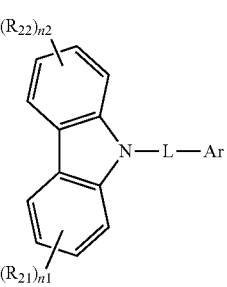

Formula 2 wherein, in Formula 2,

Ar is a substituted or unsubstituted silyl group, a substituted or unsubstituted aryl group of 6 to 30 ring-forming carbon atoms, or a substituted or unsubstituted heteroaryl group of 3 to 30 ring-forming carbon atoms, L is a direct linkage, a substituted or unsubstituted arylene group having 6 to 30 ring-forming carbon atoms, or a substituted or unsubstituted heteroarylene group having 3 to 30 ring-forming carbon atoms, $R_{21}$ and $R_{22}$ are each, independently from one another, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and n1 and n2 are each, independently from one another, an integer of 0 to 4, and

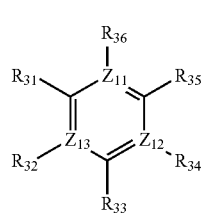

Formula 3 wherein, in Formula 3, $R_{31}$, $R_{32}$, $R_{33}$, $R_{34}$, $R_{35}$, and $R_{36}$ are each, independently from one another, a hydrogen atom, a deuterium atom, a cyano group, a substituted silyl group, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and $Z_{11}$, $Z_{12}$, and $Z_{13}$ are each, independently from one another, C or N.

The variables $R_{1s}$ and $R_{2s}$ may be, independently of one another, represented by any one of Formula S1 to Formula S3:

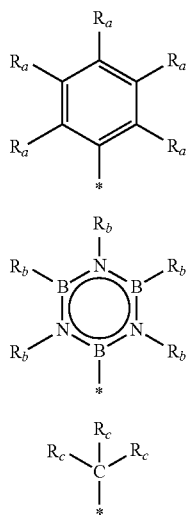

[S1]
[S2]
[S3]

wherein, in Formula S1 to Formula S3, wherein the variables are defined herein.

The variables $R_{1s}$ and $R_{2s}$ may include, independently of one another, at least one substituent represented by Group R, wherein the variables are defined herein.

According to a further aspect of the invention, an organometallic compound for an organic electroluminescence device is represented by Formula A or Formula B:

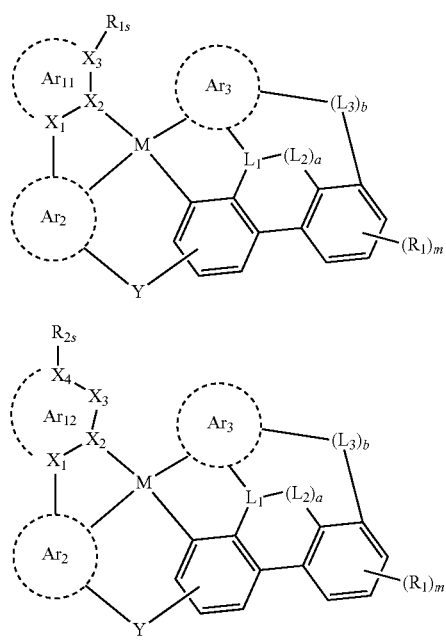

Formula A

Formula B wherein, in Formula A and Formula B,

M is Pt, Au, Pd, Cu, or Ag, $Ar_{11}$, $Ar_{12}$, $Ar_2$, and $Ar_3$ are each, independently from one another, a substituted or unsubstituted aromatic hydrocarbon group of 6 to 30 ring-forming carbon atoms, or a substituted or unsubstituted aromatic heterocycle of 2 to 30 ring-forming carbon atoms, $X_1$, $X_2$, $X_3$, and $X_4$ are each, independently from one another, N or C, Y is O or S, $R_{1s}$ and $R_{2s}$ are each, independently from one another, an aryl group substituted with at least one of a hydrogen atom, a deuterium atom, a substituted or unsubstituted alkyl group, a cyano group, a substituted or unsubstituted aryl group, a substituted or unsubstituted alkyl group, and a substituted borazine group, $L_1$ is a direct linkage or N, $L_2$ is a direct linkage, $L_3$ is a substituted or unsubstituted alkylene group having 1 to 30 carbon atoms, a is 0 or 1, b is an integer of 0 to 2, $R_1$ is a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, and m is an integer of 0 to 4.

The organometallic compound represented by Formula A or Formula B, independently from one another, may include at least one compound represented by Compound Group 1, wherein the compounds are defined herein.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
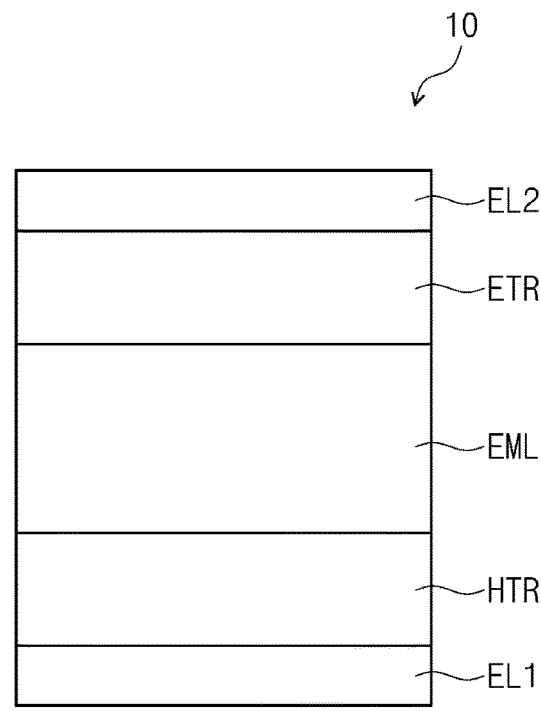
FIG. 1 is a cross-sectional view schematically illustrating an exemplary embodiment of an organic electroluminescence device constructed according to principles of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, plates, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, fixed numbers, integers, steps, processes, operations, elements, components, and/or groups thereof, but do not preclude the presence or addition of one or more other features, fixed numbers, integers, steps, processes, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

FIGS. 1 to 5 are cross-sectional views schematically illustrating exemplary embodiments of organic electroluminescence devices constructed according to principles of the invention. Referring to FIGS. 1 to 5, the organic electroluminescence devices 10, 20, 30, 40, and 50 may include a first electrode EL1, a hole transport region HTR, an emission layer EML, an electron transport region ETR, and a second electrode EL2 that are sequentially stacked.

The first electrode EL1 and the second electrode EL2 face each other, and a plurality of organic layers may be disposed between the first electrode EL1 and the second electrode EL2. The plurality of organic layers may include the hole transport region HTR, the emission layer EML, and the electron transport region ETR. The organic electroluminescence device 10 may include an organometallic compound (or a first compound), a first host (or a second compound), and a second host (or a third compound), which will be described below, in at least one layer among the plurality of organic layers.

Figure 2:
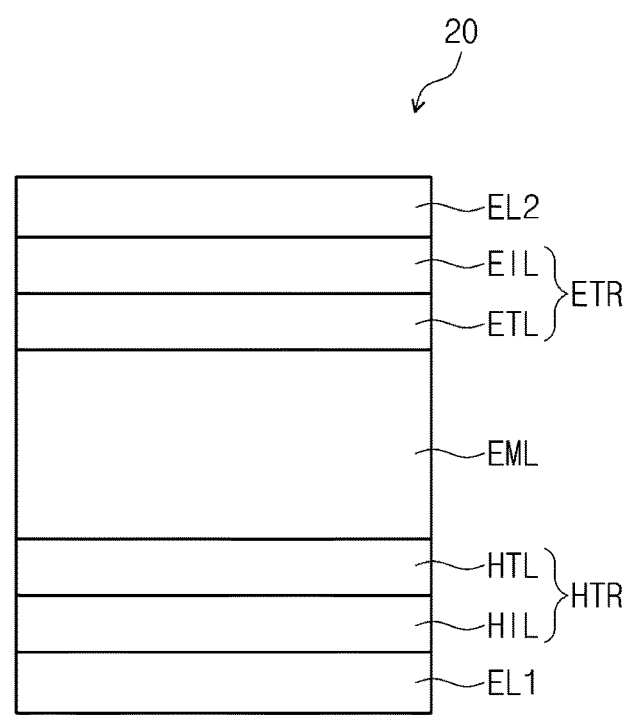
FIG. 2 is a cross-sectional view schematically illustrating an exemplary embodiment of an organic electroluminescence device constructed according to principles of the invention.
Figure 3:
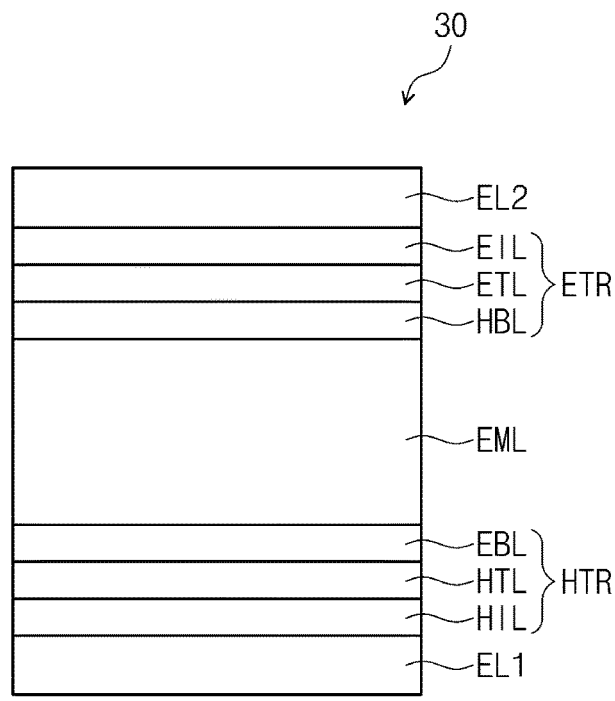
FIG. 3 is a cross-sectional view schematically illustrating an exemplary embodiment of an organic electroluminescence device constructed according to principles of the invention.
Figure 4:
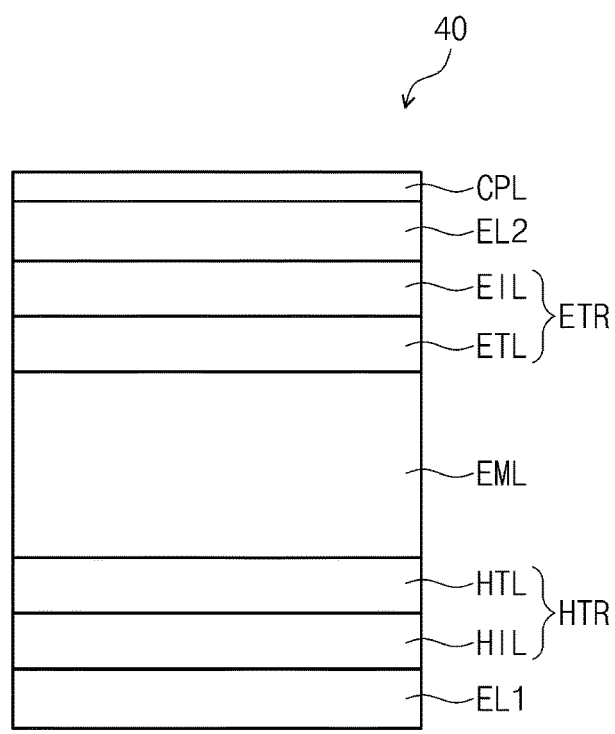
FIG. 4 is a cross-sectional view schematically illustrating an exemplary embodiment of an organic electroluminescence device constructed according to principles of the invention.
Figure 5:
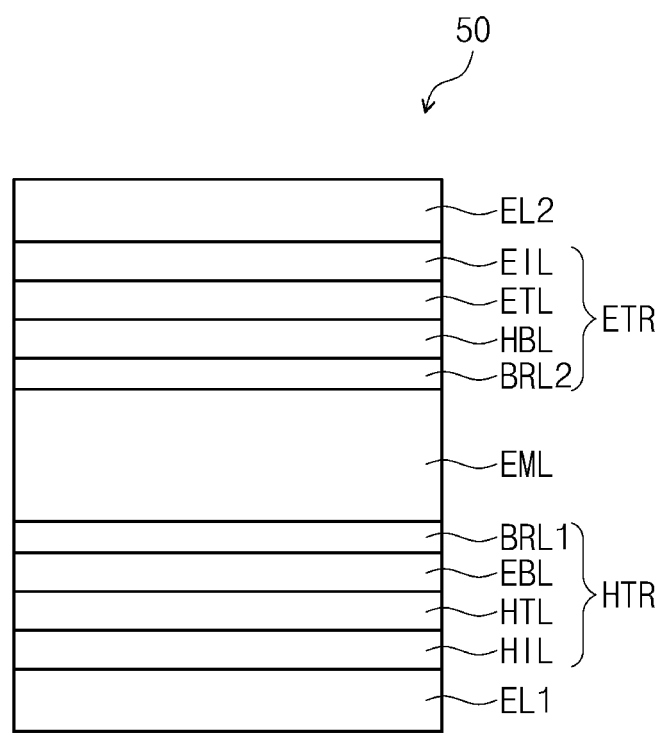
FIG. 5 is a cross-sectional view schematically illustrating an exemplary embodiment of an organic electroluminescence device constructed according to principles of the invention.

Compared to FIG. 1, FIG. 2 illustrates a cross-sectional view of an organic electroluminescence device 20, in which a hole transport region HTR includes a hole injection layer HIL and a hole transport layer HTL, and an electron transport region ETR includes an electron injection layer EIL and an electron transport layer ETL. In addition, compared to FIG. 1, FIG. 3 illustrates a cross-sectional view of an organic electroluminescence device 30, in which a hole transport region HTR includes a hole injection layer HIL, a hole transport layer HTL, and an electron blocking layer EBL, and an electron transport region ETR includes an electron injection layer EIL, an electron transport layer ETL, and a hole blocking layer HBL. Compared to FIG. 2, FIG. 4 illustrates a cross-sectional view of an organic electroluminescence device 40 including a capping layer CPL disposed on the second electrode EL2. Compared to FIG. 2, FIG. 5 illustrates a cross-sectional view of an organic electroluminescence device 50 including a hole barrier reinforced layer BRL1 disposed below the emission layer EML and an electron barrier reinforced layer BRL2 disposed above the emission layer EML.

The first electrode EL1 has conductivity. The first electrode EL1 may be formed of a metal alloy or a conductive compound. The first electrode EL1 may be an anode. In addition, the first electrode EL1 may be a pixel electrode. The first electrode EL1 may be a transmissive electrode, a transflective electrode, or a reflective electrode. When the first electrode EL1 is the transmissive electrode, the first electrode EL1 may include a transparent metal oxide, such as, an indium tin oxide (ITO), an indium zinc oxide (IZO), a zinc oxide (ZnO), and an indium tin zinc oxide (ITZO). When the first electrode EL1 is the transflective electrode or the reflective electrode, the first electrode EL1 may include Ag, Mg, Cu, Al, Pt, Pd, Au, Ni, Nd, Ir, Cr, Li, Ca, LiF/Ca, LiF/Al, Mo, Ti, a compound thereof or a mixture thereof (e.g., a mixture of Ag and Mg). Alternatively, the first electrode EL1 may have a multilayer structure including a reflective layer or a transflective layer formed of the above-described materials, and a transparent conductive layer formed of the ITO, IZO, ZnO, ITZO, etc. For example, the first electrode EL1 may have a three-layer structure of ITO/Ag/ITO, but the exemplary embodiments are not limited thereto. The thickness of the first electrode EL1 may be from about 1,000 Å to about 10,000 Å, for example, from about 1,000 Å to about 3,000 Å.

The hole transport region HTR is provided on the first electrode EL1. The hole transport region HTR may include at least one of a hole injection layer HIL, a hole transport layer HTL, a hole buffer layer, an electron blocking layer EBL, or a hole barrier reinforced layer BRL1. The thickness of the hole transport region HTR may be, for example, from about 50 Å to about 15,000 Å.

The hole transport region HTR may have a single layer formed of a single material, a single layer formed of a plurality of different materials, or a multilayer structure including a plurality of layers formed of a plurality of different materials.

For example, the hole transport region HTR may have a single layer structure of a hole injection layer HIL or a hole transport layer HTL, or a single layer structure formed of a hole injection material and a hole transport material. In addition, the hole transport region HTR may have a single layer structure formed of a plurality of different materials, or a structure in which a hole injection layer HIL/hole transport layer HTL, a hole injection layer HIL/hole transport layer HTL/hole buffer layer, a hole injection layer HIL/hole buffer layer, a hole transport layer HTL/hole buffer layer, or a hole barrier reinforced layer BRL1/hole injection layer HIL/hole transport layer HTL/electron blocking layer EBL are stacked in order from the first electrode EL1, but the exemplary embodiments are not limited thereto.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, for example, a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4"-[tris(3-methylphenyl)phenylamino]triphenylamine] (m-MTDATA), 4,4',4"-tris(N,N-diphenylamino)triphenylamine (TDATA), 4,4',4"-tris{N,-(2-naphthyl)-N-phenylamino)-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalene-1-yl)-N,N'-diphenyl-benzidine (NPD), triphenylamine-containing polyetherketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

The hole transport layer HTL may include, for example, carbazole derivatives such as N-phenyl carbazole and polyvinyl carbazole, fluorene derivatives, N,N'-bis(3-methylphenyl)-N,N-diphenyl-[1,1-biphenyl]-4,4'-diamine (TPD), triphenylamine derivatives such as 4,4',4''-tris(N-carbazolyl) triphenylamine (TCTA), N,N'-di(naphthalene-1-yl)-N,N'-diphenyl-benzidine (NPB), 4,4'-cyclohexylidene bis[N,N-bis(4-methylphenyl]benzenamine] (TAPC), 4,4'-bis[N,N-(3-tolyl)amino]-3,3'-dimethylbiphenyl (HMTPD), 1,3-Bis (N-carbazolyl)benzene (mCP), etc.

The thickness of the hole transport region HTR may be from about 50 Å to about 10,000 Å, for example, from about 100 Å to about 5,000 Å. The thickness of the hole injection region HIL may be, for example, from about 30 Å to about 1,000 Å, and the thickness of the hole transport layer HTL may be from about 30 Å to about 1,000 Å. For example, the thickness of the electron blocking layer EBL may be from about 10 Å to about 1,000 Å. If the thicknesses of the hole transport region HTR, the hole injection layer HIL, the hole transport layer HTL and the electron blocking layer EBL satisfy the above-described ranges, satisfactory hole transport properties may be achieved without a substantial increase in driving voltage.

The hole transport region HTR may further include, in addition to the above-described materials, a charge generating material to increase conductivity. The charge generating material may be dispersed uniformly or non-uniformly in the hole transport region HTR. The charge generating material may be, for example, a p-dopant. The p-dopant may be one of quinone derivatives, metal oxides, or cyano group-containing compounds, but the exemplary embodiments are not limited thereto. For example, non-limiting examples of the p-dopant may include quinone derivatives such as tetracyanoquinodimethane (TCNQ) and 2,3,5,6-tetrafluoro-7,7',8,8'-tetracyanoquinodimethane (F4-TCNQ), metal oxides such as tungsten oxide and molybdenum oxide, etc., but the exemplary embodiments are not limited thereto.

As described above, the hole transport region HTR may further include at least one of a hole buffer layer, an electron blocking layer EBL, or a hole barrier reinforced layer BRL1 in addition to the hole injection layer HIL and the hole transport layer HTL. The hole buffer layer may compensate a resonance distance according to the wavelength of light emitted from an emission layer EML and may increase light emission efficiency. Materials which may be included in the hole transport region HTR may be used as materials which may be included in the hole buffer layer. The electron blocking layer EBL is a layer that serves to prevent electrons from being injected from the electron transport region ETR to the hole transport region HTR. The hole barrier reinforced layer BRL1 may reduce an energy gap between the emission layer and the hole transport region HTR. In addition, the hole barrier reinforced layer BRL1 may have higher hole transfer ability than the electron blocking layer EBL. In some exemplary embodiments, the hole barrier reinforced layer BRL1 may include at least one among Compound 1-1 to Compound 1-22 of Compound Group H1, but the exemplary embodiments are not limited thereto. The emission layer EML is provided on the hole transport region HTR. The thickness of the emission layer EML may be, for example, from about 100 Å to about 1000 Å or from about 100 Å to about 300 Å. The emission layer EML may have a single layer formed of a single material, a single layer formed of a plurality of different materials, or a multilayer structure having a plurality of layers formed of a plurality of different materials.

The emission layer EML in the organic electroluminescence devices may include a polycyclic compound.

As used herein, the term "substituted or unsubstituted" may mean substituted or unsubstituted with at least one substituent selected from the group consisting of a deuterium atom, a halogen atom, a cyano group, a nitro group, an amine group, a silyl group, an oxy group, a thio group, a sulfinyl group, a sulfonyl group, a carbonyl group, a boron group, a phosphine oxide group, a phosphine sulfide group, an alkyl group, an alkenyl group, an alkoxy group, a hydrocarbon ring group, an aryl group, and a heterocyclic group. In addition, each of the substituents exemplified above may be substituted or unsubstituted. For example, a biphenyl group may be interpreted as an aryl group or a phenyl group substituted with a phenyl group.

As used herein, the phrase "bonded to an adjacent group to form a ring" may indicate that one is bonded to an adjacent group to form a substituted or unsubstituted hydrocarbon ring, or a substituted or unsubstituted heterocycle. The hydrocarbon ring includes an aliphatic hydrocarbon ring and an aromatic hydrocarbon ring. The heterocycle includes an aliphatic heterocycle and an aromatic heterocycle. The hydrocarbon ring and the heterocycle may be monocyclic or polycyclic. In addition, the rings formed by being bonded to each other may be connected to another ring to form a spiro structure.

As used herein, the phrase "bonded to an adjacent ring to form a ring" may indicate that adjacent two rings are bonded to form a substituted or unsubstituted hydrocarbon ring, or a substituted or unsubstituted heterocycle.

As used herein, the term "an adjacent group" may mean a substituent substituted for an atom which is directly connected to an atom substituted with a corresponding substituent, another substituent substituted for an atom which is substituted with a corresponding substituent, or a substituent sterically positioned at the nearest position to a corresponding substituent. For example, two methyl groups in 1,2-dimethylbenzene may be interpreted as "adjacent groups" to each other and two ethyl groups in 1,1-diethylcyclopentane may be interpreted as "adjacent groups" to each other.

As used herein, examples of the halogen atom may include a fluorine atom, a chlorine atom, a bromine atom, and an iodine atom.

As used herein, the alkyl group may be a linear, branched or cyclic type. The number of carbons in the alkyl group is 1 to 50, 1 to 30, 1 to 20, 1 to 10, or 1 to 6. Examples of the alkyl group may include, but are not limited to, methyl group, ethyl group, n-propyl group, isopropyl group, n-butyl group, s-butyl group, t-butyl group, i-butyl group, 2-ethylbutyl group, 3,3-dimethylbutyl group, n-pentyl group, i-pentyl group, neopentyl group, t-pentyl group, cyclopentyl group, 1-methylpentyl group, 3-methylpentyl group, 2-ethylpentyl group, 4-methyl-2-pentyl group, n-hexyl group, 1-methylhexyl group, 2-ethylhexyl group, 2-butylhexyl group, cyclohexyl group, 4-methylcyclohexyl group, 4-t-butylcyclohexyl group, n-heptyl group, 1-methylheptyl group, 2,2-dimethylheptyl group, 2-ethylheptyl group, 2-butylheptyl group, n-octyl group, t-octyl group, 2-ethyloctyl group, 2-butyloctyl group, 2-hexyloctyl group, 3,7-dimethyloctyl group, cyclooctyl group, n-nonyl group, n-decyl group, adamantyl group, 2-ethyldecyl group, 2-butyldecyl group, 2-hexyldecyl group, 2-octyldecyl group, n-undecyl group, n-dodecyl group, 2-ethyldodecyl group, 2-butyldodecyl group, 2-hexyldocecyl group, 2-octyldodecyl group, n-tridecyl group, n-tetradecyl group, n-pentadecyl group, n-hexadecyl group, 2-ethylhexadecyl group, 2-butylhexadecyl group, 2-hexylhexadecyl group, 2-octylhexadecyl group, n-heptadecyl group, n-octadecyl group, n-nonadecyl group, n-eicosyl group, 2-ethyleicosyl group, 2-butyleicosyl group, 2-hexyleicosyl group, 2-octyleicosyl group, n-henicosyl group, n-docosyl group, n-tricosyl group, n-tetracosyl group, n-pentacosyl group, n-hexacosyl group, n-heptacosyl group, n-octacosyl group, n-nonacosyl group, n-triacontyl group, etc.

As used herein, a hydrocarbon ring group may be an any functional group or substituent derived from an aliphatic hydrocarbon ring, or an any functional group or substituent derived from an aromatic hydrocarbon ring. The number of ring-forming carbon atoms in the hydrocarbon ring group may be 5 to 60, 5 to 30, or 5 to 20.

As used herein, an aryl group means any functional group or substituent derived from an aromatic hydrocarbon ring. The aryl group may be a monocyclic aryl group or a polycyclic aryl group. The number of ring-forming carbon atoms in the aryl group may be 6 to 30, 6 to 20, or 6 to 15. Examples of the aryl group may include phenyl, naphthyl, fluorene, anthracene, phenanthryl, biphenyl, terphenyl, quaterphenyl, quinqphenyl, sexiphenyl, triphenylenyl, pyrenyl, benzofluoranthenyl, chrysenyl, etc., but the exemplary embodiments are not limited thereto.

As used herein, the heterocyclic group refers to any functional group or substituent derived from a ring including at least one of B, O, N, P, Si, or Se as a heteroatom. The heterocyclic group includes an aliphatic heterocyclic group and an aromatic heterocyclic group. The aromatic heterocyclic group may be a heteroaryl group. The aliphatic heterocycle and the aromatic heterocycle may be monocyclic or polycyclic.

When the heterocyclic group contains two or more hetero atoms, the two or more hetero atoms may be the same as or different from each other. The heterocyclic group may be a monocyclic heterocyclic group or a polycyclic heterocyclic group, and includes a heteroaryl group. The number of ring-forming carbon atoms in the heterocyclic group may be 2 to 30, 2 to 20, or 2 to 10.

The number of carbons for forming a ring of the aliphatic heterocyclic group may be 2 to 30, 2 to 20, or 2 to 10. Examples of the aliphatic heterocyclic group may include, but are not limited to, oxirane group, thiirane group, pyrrolidine group, piperidine group, tetrahydrofuran group, tetrahydrothiophene group, thiane group, tetrahydropyran group, 1,4-dioxane group, etc.

As used herein, the heteroaryl group may include at least one of B, O, N, P, Si, or S as a heteroatom. When the heteroaryl group contains two or more heteroatoms, the two or more heteroatoms may be the same as or different from each other. The heteroaryl group may be a monocyclic heteroaryl group or a polycyclic heteroaryl group. The number of ring-forming carbon atoms in the heteroaryl group may be 2 to 30, 2 to 20, or 2 to 10. Examples of the heteroaryl group may include thiophene, furan, pyrrole, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidyl, pyrido pyrazinyl, pyrazino pyrazinyl, isoquinoline, indole, carbazole, N-arylcarbazole, N-heteroarylcarbazole, N-alkylcarbazole, benzoxazole, benzoimidazole, benzothiazole, benzocarbazole, benzothiophene, dibenzothiophenyl, thienothiophene, benzofuranyl, phenanthroline, thiazolyl, isooxazolyl, oxadiazolyl, thiadiazolyl, phenothiazolyl, phenothiazinyl, dibenzosilole, dibenzofuranyl, etc., but are not limited thereto.

As used herein, the silyl group includes an alkyl silyl group and an aryl silyl group. Examples of the silyl group may include, but are not limited to, trimethylsilyl, triethylsilyl, t-butyldimethylsilyl, vinyldimethylsilyl, propyldimethylsilyl, triphenylsilyl, diphenylsilyl, phenylsilyl, etc.

As used herein, the alkyl group in the alkylamine group is the same as examples of the alkyl group described above.

As used herein, the aryl group in the arylamine group is the same as examples of the aryl group described above.

As used herein, the direct linkage may mean a single bond.

As used herein "  " or " ——*" means the position to be linked.

As used herein, the term "atom" may mean an element or its corresponding radical bonded to one or more other atoms.

The terms "hydrogen" and "deuterium" refer to their respective atoms and corresponding radicals, and the terms "—F, —Cl, —Br, and —I" are radicals of, respectively, fluorine, chlorine, bromine, and iodine.

As used herein, a substituent for a monovalent group, e.g., alkyl, may also be, independently, a substituent for a corresponding divalent group, e.g., alkylene.

The emission layer EML of the organic electroluminescence device may include the first compound represented by Formula 1 below, the second compound represented by Formula 2 below, and the third compound represented by Formula 3 below.

The first compound is the organometallic compound represented by Formula 1 below:

Formula 1

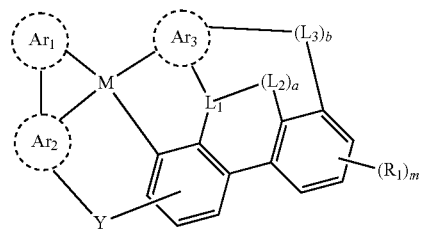

In Formula 1 above, M may be a transition metal. Specifically, M may be Pt, Au, Pd, Cu, or Ag. For example, M may be Pt.

In Formula 1, Y is O or S. In particular, Y may be O.

In Formula 1, $Ar_1$, $Ar_2$, and $Ar_3$ may be each independently a substituted or unsubstituted aromatic hydrocarbon ring having 6 to 30 ring-forming carbon atoms, or a substituted or unsubstituted aromatic heterocycle having 3 to 30 ring-forming carbon atoms.

Specifically, $Ar_1$ may be a substituted or unsubstituted aromatic heterocycle having 2 to 30 ring-forming carbon atoms. For example, $Ar_1$ may be a substituted or unsubstituted aromatic heterocycle having 5 ring-forming carbon atoms and containing a nitrogen atom. $Ar_1$ may be a substituted of unsubstituted benzimidazole ring, or a substituted of unsubstituted pyrazole ring. In some exemplary embodiments, $Ar_1$ may be

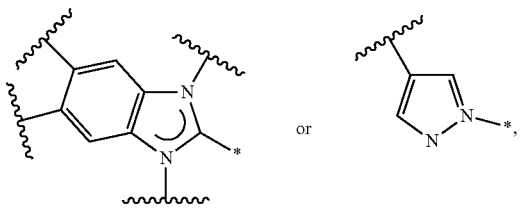

In particular, $Ar_1$ includes an aryl group substituted with at least one of a hydrogen atom, a deuterium atom, a substituted or unsubstituted alkyl group, a cyano group, or a substituted or unsubstituted aryl group, a substituted or unsubstituted alkyl group, or a substituted borazine group, as described further below.

Specifically, $Ar_2$ may be a substituted or unsubstituted aromatic hydrocarbon ring having 6 ring-forming carbon atoms or a substituted or unsubstituted aromatic heterocycle having 6 ring-forming carbon atoms. For example, $Ar_2$ may be a substituted or unsubstituted benzene ring. Alternatively, $Ar_1$ may be a substituted or unsubstituted borazine group, for example, 1,3,5,2,4,6-triazatriborinane.

Specifically, $Ar_3$ may be a substituted or unsubstituted aromatic heterocycle having 2 to 30 ring-forming carbon atoms. For example, $Ar_3$ may be an aromatic heterocycle having 5 or 6 ring-forming carbon atoms and containing a nitrogen atom. For example, $Ar_3$ may be a substituted or unsubstituted imidazole, or a substituted or unsubstituted pyridine.

In Formula 1, $L_1$ is a direct linkage or N.

In Formula 1, $L_2$ is a direct linkage.

In Formula 1, $L_3$ is a substituted or unsubstituted alkyl group having 1 to 30 carbon atoms.

In Formula 1, a is 0 or 1, and b is an integer of 0 to 2.

Specifically, in some exemplary embodiments, when $L_1$ is a direct linkage, a may be 0, and b may be 1 or 2. In some exemplary embodiments, when $L_1$ is N, a may be 1, and b may be 2.

In Formula 1, $R_1$ may be a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, $R_1$ is a direct linkage, and may be directly bonded to $Ar_3$ to form a ring. Specifically, when $L_1$ is a direct linkage and a is 0, $R_1$ may be directly bonded to $Ar_3$ to form a ring.

In Formula 1, m is an integer of 0 to 4. For example, m may be 0 or 1. The case where m is 0 may be the same as the case where m is 1 and $R_1$ is a hydrogen atom.

In some exemplary embodiments, the organometallic compound represented by Formula 1 above may be represented by Formula 1-1a or Formula 1-1b below:

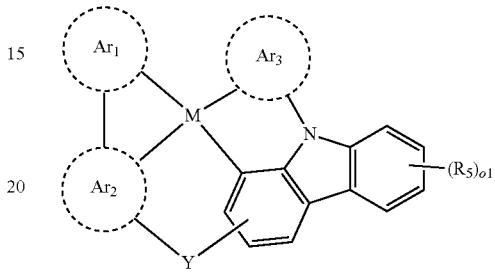

Formula 1-1a

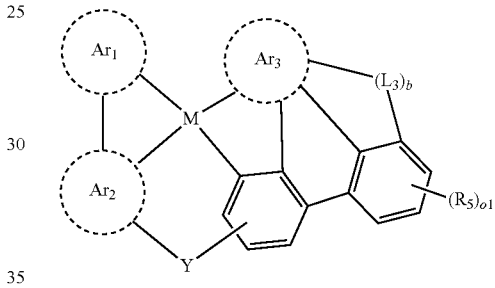

Formula 1-1b

Formula 1-1a above is the specified case where $L_1$ is N, a is 1, and b is 0 in Formula 1 above.

Formula 1-1b above is the specified case where $L_1$ is a direct linkage and a is 0 in Formula 1 above. In addition, Formula 1-1b above is the specified case where m is 1 or more, one of $R_1$ is a direct linkage, and the $R_1$ which is a direct linkage is bonded to an adjacent group to form a ring. For example, the $R_1$ may form a ring by bonding with $Ar_3$ in Formula 1 above, and the remaining $R_1$s is indicated by $R_6$. Thus, o2 may be same with m−1.

In Formula 1-1a and Formula 1-1b above, $R_5$ and $R_6$ may be each independently a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, each of $R_5$ and $R_6$ may be a hydrogen atom.

In Formula 1-1a and Formula 1-1b above, o1 is an integer of 0 to 4. For example, o1 may be 0 or 1. The case where o1 is 0 may be the same as the case where o1 is 1 and $R_5$ is a hydrogen atom.

In Formula 1-1a and Formula 1-1b above, o2 is an integer of 0 to 3. For example, o2 may be 0 or 1. The case where o2 is 0 may be the same as the case where o2 is 1 and $R_6$ is a hydrogen atom.

In Formula 1-1a and Formula 1-1b above, those described in Formula 1 may be equally applied to M, $Ar_1$ to $Ar_3$, Y, and $L_3$.

In some exemplary embodiments, the organometallic compound represented by Formula 1 above may be represented by Formula 1-2a or 1-2b below:

Formula 1-2a

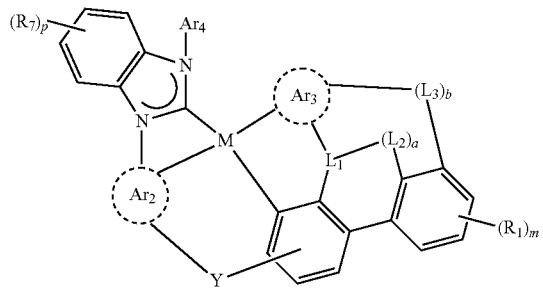

Formula 1-2b

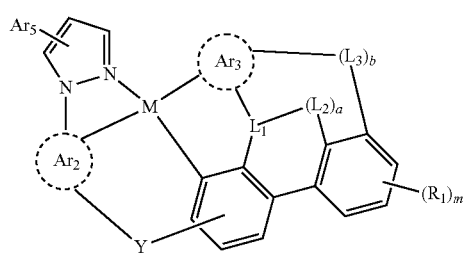

Formula 1-2a and Formula 1-2b above are the specified cases where $Ar_1$ is a substituted or unsubstituted aromatic heterocycle having 5 ring-forming carbon atoms in Formula 1 above. Specifically, $Ar_1$ may be a substituted or unsubstituted aromatic heterocycle containing a nitrogen atom as a heteroatom.

In Formula 1-2a above, $R_7$ may be a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, $R_7$ may be a hydrogen group. However, the exemplary embodiments are not limited thereto.

In Formula 1-2a above, p is an integer of 0 to 4. For example, p may be 0 or 1. The case where p is 0 may be the same as the case where p is 1 and $R_7$ is a hydrogen atom.

In Formula 1-2a and Formula 1-2b above, $Ar_4$ and $Ar_5$ may be each independently represented by any one among Formula S1 to Formula S3 below:

S1

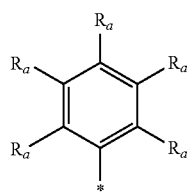

S2

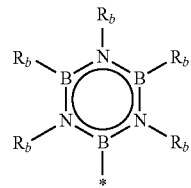

S3

In Formula S1 to Formula S3 above, $R_a$, $R_b$, and $R_c$ may be each independently a hydrogen atom, a deuterium atom, a substituted or unsubstituted alkyl group having 1 to 30 carbon atoms, a cyano group, and a substituted or unsubstituted aryl group having 6 to 30 ring-forming carbon atoms, or may be bonded to an adjacent group to form a ring.

For example, $R_a$ may be a hydrogen atom, a deuterium atom, a methyl group, a substituted or unsubstituted isopropyl group, a substituted or unsubstituted t-butyl group, or a substituted or unsubstituted phenyl group. Specifically, $R_a$ may be an unsubstituted methyl group, an isopropyl group substituted with deuterium, a t-butyl group substituted with deuterium, or a phenyl group substituted with deuterium. However, the exemplary embodiments are not limited thereto. For example, $R_b$ may be a methyl group. However, the exemplary embodiments are not limited thereto.

For example, $R_c$ may be a substituted or unsubstituted alkyl group having 1 to 30 carbon atoms. Specifically, $R_c$ may be a substituted or unsubstituted methyl group. For example, $R_c$ may be a methyl group substituted with deuterium. However, the exemplary embodiments are not limited thereto.

In Formula 1-2a and Formula 1-2b above, those described in Formula 1 may be equally applied to M, Y, $Ar_2$, $Ar_3$, $L_1$ to $L_3$, a, b, $R_1$, and m.

In some exemplary embodiments, the organometallic compound represented by Formula 1 above may be represented by Formula 1-3a or Formula 1-3b below:

Formula 1-3a

Formula 1-3b

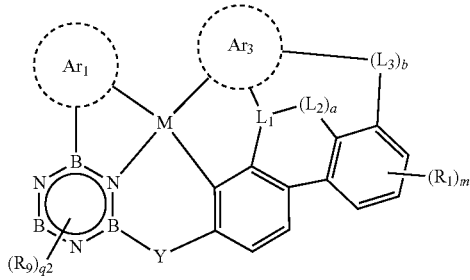

Formula 1-3a and Formula 1-3b above are the cases where $Ar_3$ is specified in Formula 1 above. Specifically, Formula 1-3a is the specified case where $Ar_2$ is a substituted or unsubstituted benzene ring in Formula 1. Formula 1-3b is the specified case where $Ar_2$ is a substituted or unsubstituted borazine group in Formula 1.

In Formula 1-3a and Formula 1-3b, $R_8$ and $R_9$ may be each independently a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, $R_8$ and $R_9$ may be each independently a hydrogen atom, a substituted or unsubstituted cycloalkyl group, or a substituted or unsubstituted t-butyl group. However, the exemplary embodiments are not limited thereto.

In Formula 1-3a and Formula 1-3b, q1 and q2 are each independently an integer of 0 to 3. For example, q1 and q2 may be each independently 0 or 1.

In Formula 1-3a and Formula 1-3b above, those described in Formula 1 may be equally applied to M, Y, $Ar_1$ to $Ar_3$, $L_1$ to $L_3$, a, b, $R_1$, and m.

In some exemplary embodiments, the organometallic compound represented by Formula 1 above may be represented by Formula 1-4a or Formula 1-4b below:

Formula 1-4a

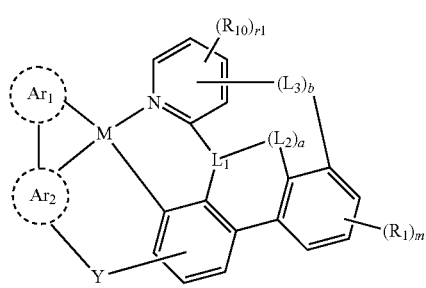

Formula 1-4b

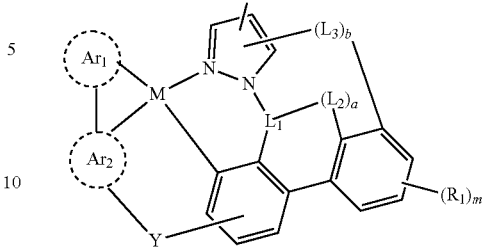

Formula 1-4a and Formula 1-4b above are the cases where $Ar_3$ is specified in Formula 1 above. Specifically, Formula 1-4a is the specified case where $Ar_3$ is a substituted or unsubstituted aromatic heterocycle having 6 ring-forming carbon atoms in Formula 1. Formula 1-4b is the specified case where $Ar_3$ is a substituted or unsubstituted aromatic heterocycle having 5 ring-forming carbon atoms in Formula 1.

In Formula 1-4a and Formula 1-4b, $R_{10}$ and $R_{11}$ may be each independently a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, $R_{10}$ may be a t-butyl group, a substituted or unsubstituted phenyl group, or a substituted or unsubstituted borazine group. For example, $R_{11}$ may be a substituted or unsubstituted t-butyl group, a substituted or unsubstituted phenyl group, or a substituted or unsubstituted borazine group. However, the exemplary embodiments are not limited thereto.

In Formula 1-4a and Formula 1-4b, r1 is an integer of 0 to 3. For example, r1 may be 0 or 1.

In Formula 1-4a and Formula 1-4b, r2 is an integer of 0 to 2.

In Formula 1-4a and Formula 1-4b, those described in Formula 1 may be equally applied to M, Y, $Ar_1$, $Ar_2$, $L_1$ to $L_3$, a, b, $R_1$, and m.

In some exemplary embodiments, the organometallic compound represented by Formula 1 above may be represented by Formula 1-5 below:

Formula 1-5

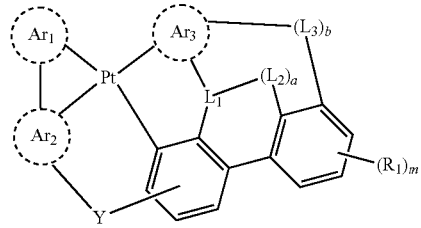

Formula 1-5 above is the specified case where M is Pt in Formula 1 above. However, the exemplary embodiments are not limited thereto.

In Formula 5, those described in Formula 1 may be equally applied to Y, $Ar_1$ to $Ar_3$, $L_1$ to $L_3$, a, b, $R_1$, and m.

In some exemplary embodiments, the organometallic compound represented by Formula 1 above may be represented by Formula 1-6 below:

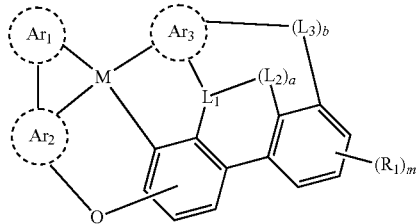

Formula 1-6

Formula 1-6 above is the specified case where Y is 0 in Formula 1 above. However, the exemplary embodiments are not limited thereto.

In Formula 1-6, those described in Formula 1 may be equally applied to M, $Ar_1$ to $Ar_3$, $L_1$ to $L_3$, a, b, $R_1$, and m.

In some exemplary embodiments, the organometallic compound represented by Formula 1 above may be represented by Formula 1-7a or Formula 1-7b below:

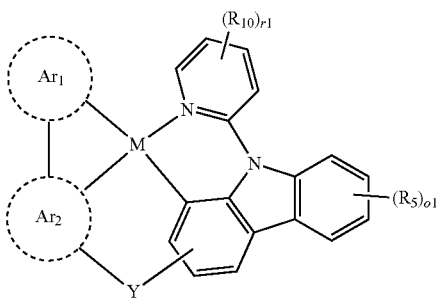

Formula 1-7a

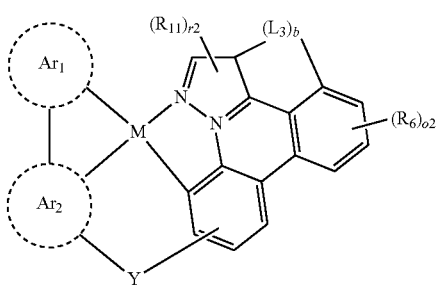

Formula 1-7b

Formula 1-7a and Formula 1-b above are the cases where $Ar_3$, $L_1$, $L_2$, a, and b are specified in Formula 1 above. Specifically, Formula 1-7a is the specified case where $Ar_3$ is a substituted or unsubstituted aromatic heterocycle having 6 ring-forming carbon atoms, $L_1$ is N, a is 1, $L_2$ is a direct linkage, and b is 0 in Formula 1.

Specifically, Formula 1-7b is the specified case where $Ar_3$ is a substituted or unsubstituted aromatic heterocycle having 5 ring-forming carbon atoms, $L_1$ is a direct linkage, and a is 0 in Formula 1.

In Formula 1-7a and Formula 1-7b, those described in Formula 1, Formula 1-1a, Formula 1-1b, Formula 1-4a, and Formula 1-4b may be equally applied to M, Y, $Ar_1$, $Ar_2$, $L_3$, b, $R_1$, $R_5$, $R_6$, $R_{10}$, $R_{11}$, r1, r2, o1, and o2.

The first compound is the organometallic compound represented by Formula A or Formula B below:

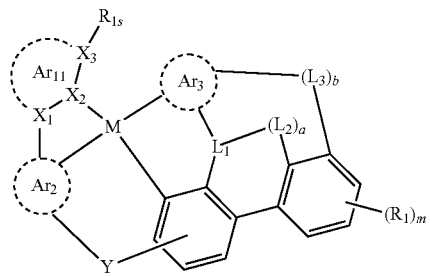

Formula A

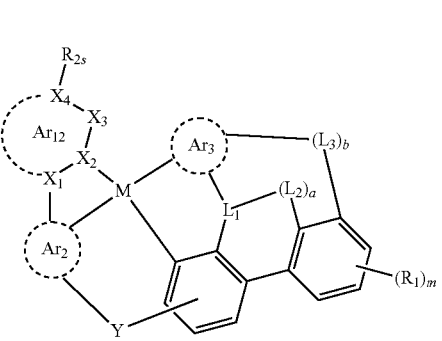

Formula B

Formula A above is that a substituent of $Ar_1$ described in Formula 1 is expressed as $R_{1s}$. Formula B is that a substituent of $Ar_1$ described in Formula 1 is expressed as $R_{2s}$.

In Formula A and Formula B, $Ar_{11}$ and $Ar_{12}$ are each independently a substituted or unsubstituted aromatic hydrocarbon group of 6 to 30 ring-forming carbon atoms, or a substituted or unsubstituted aromatic heterocycle of 2 to 30 ring-forming carbon atoms. Specifically, $Ar_{11}$ and $Ar_{12}$ may be each independently a substituted or unsubstituted aromatic heterocycle of 2 to 30 ring-forming carbon atoms.

For example, $Ar_{11}$ and $Ar_{12}$ may be each independently a substituted or unsubstituted aromatic heterocycle having 5 ring-forming carbon atoms.

In Formula A and Formula B, $X_1$, $X_2$, $X_3$, and $X_4$ are each independently N or C. For example, $X_1$ may be N. $X_2$ may be N or C. $X_3$ may be N or C. $X_4$ may be C. However, the exemplary embodiments are not limited thereto.

In Formula A and Formula B, $R_{1s}$ and $R_{2s}$ are each independently an aryl group substituted with at least one of a hydrogen atom, a deuterium atom, a substituted or unsubstituted alkyl group, a cyano group, or a substituted or unsubstituted aryl group, a substituted or unsubstituted alkyl group, or a substituted borazine group. For example, $R_{1s}$ and $R_{2s}$ may be represented by any one among Formula S1 to Formula S3 below:

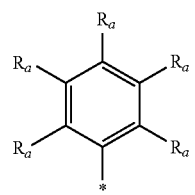

S1

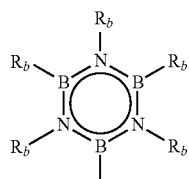
S2

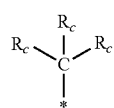
S3

In Formula S1 to Formula S3 above, $R_a$, $R_b$, and $R_c$ may be each independently a hydrogen atom, a deuterium atom, a substituted or unsubstituted alkyl group having 1 to 30 carbon atoms, a cyano group, and a substituted or unsubstituted aryl group having 6 to 30 ring-forming carbon atoms, or may be bonded to an adjacent group to form a ring.

For example, $R_a$ may be a hydrogen atom, a deuterium atom, a methyl group, a substituted or unsubstituted isopropyl group, a substituted or unsubstituted t-butyl group, or a substituted or unsubstituted phenyl group. Specifically, $R_a$ may be an isopropyl group substituted with deuterium, a t-butyl group substituted with deuterium, or a phenyl group substituted with deuterium. However, the exemplary embodiments are not limited thereto.

For example, $R_b$ may be a methyl group. However, the exemplary embodiments are not limited thereto.

For example, $R_c$ may be a substituted or unsubstituted alkyl group having 1 to 30 carbon atoms. Specifically, $R_c$ may be a substituted or unsubstituted methyl group. For example, $R_c$ may be a methyl group substituted with deuterium. However, the exemplary embodiments are not limited thereto.

The organometallic compound of some exemplary embodiments includes a substituent, such as $R_{1s}$ and $R_{2s}$, although not wanting to be bound by theory, causing a steric hindrance so that intermolecular interaction may be reduced and the stability of molecule may be increased.

In some exemplary embodiments, $R_{1s}$ and $R_{2s}$ each may include at least one among the substituents represented by Group R below:

Group R

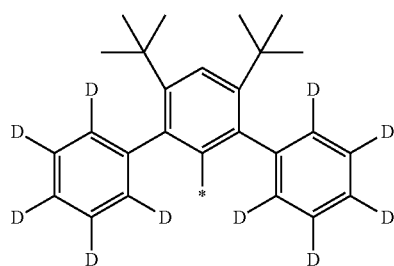
RS1

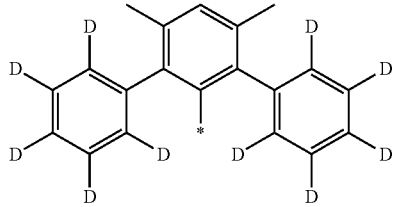
RS2

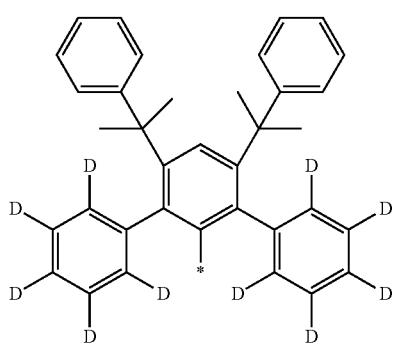
RS3

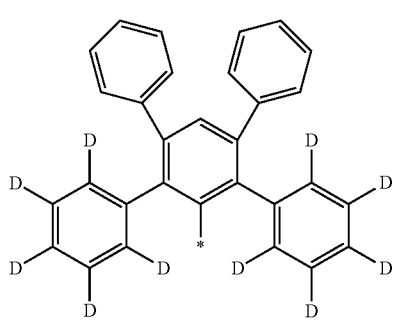
RS4

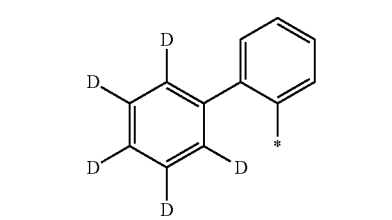
RS5

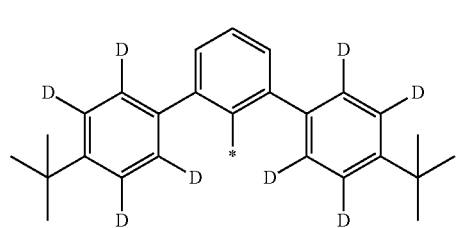
RS6

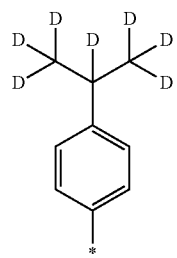
RS7

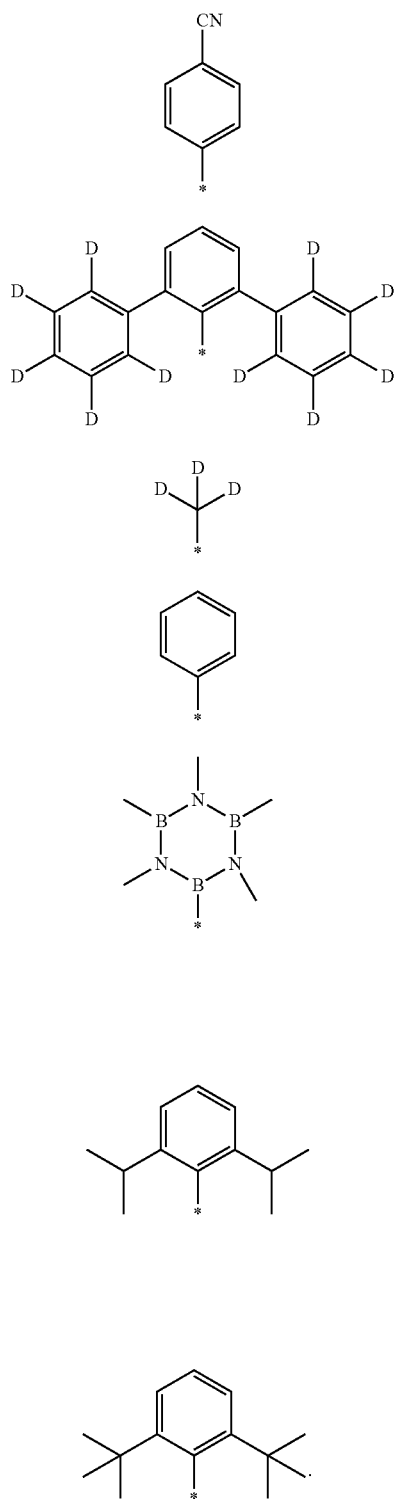
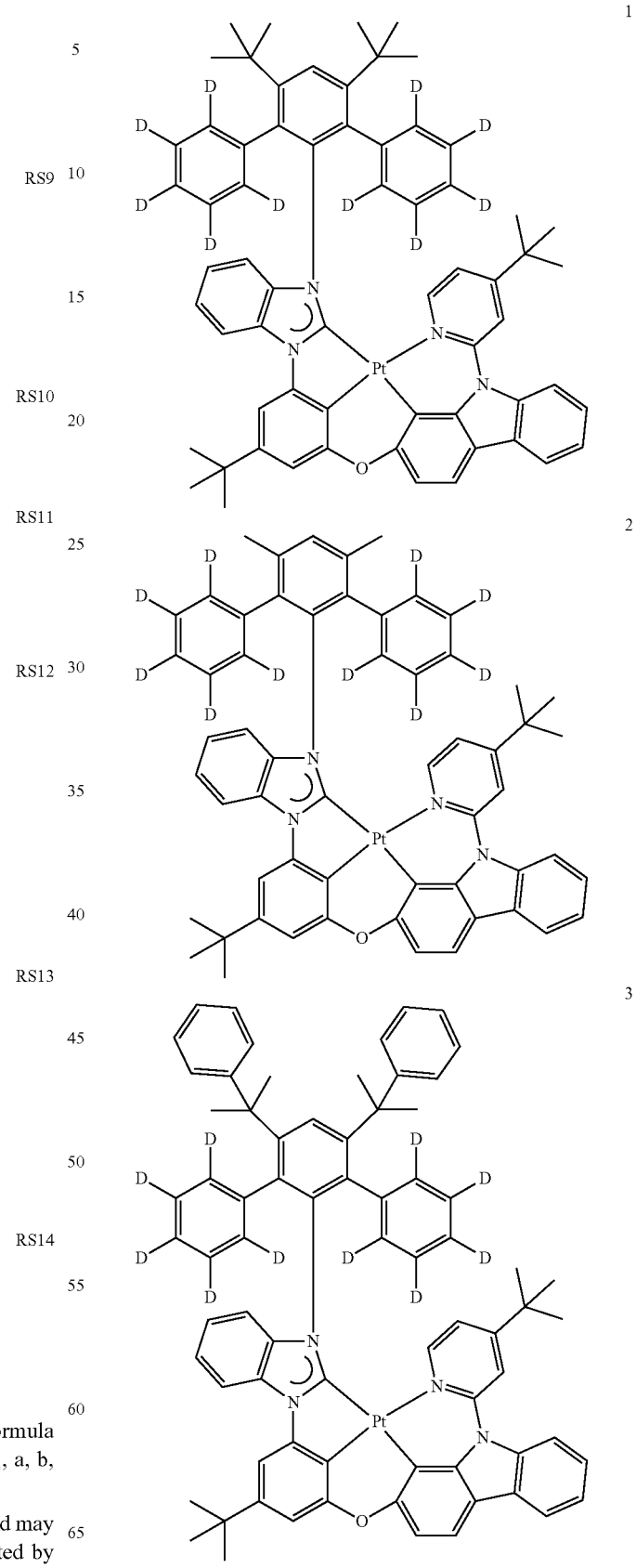
Compound Group 1
In Formula A and Formula B, those described in Formula 1 may be equally applied to M, Y, $Ar_2$, $Ar_3$, $L_1$ to $L_3$, a, b, $R_1$, and m.
In some exemplary embodiments, the first compound may include at least one among the compounds represented by Compound Group 1 below:

31
-continued
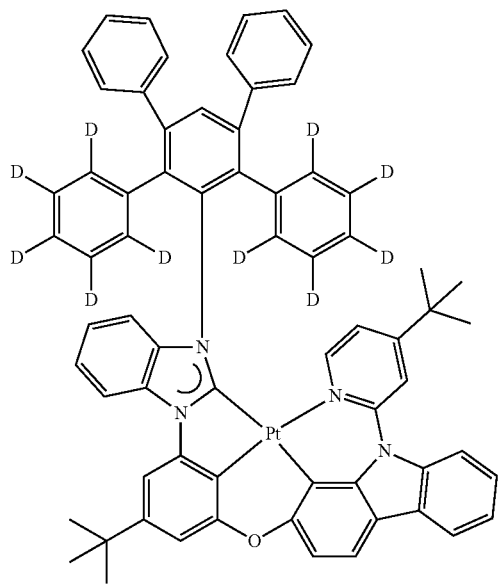
4
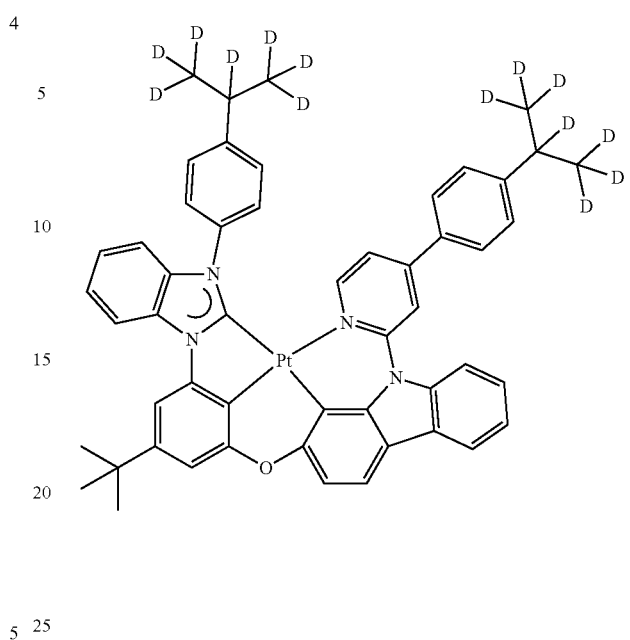
5
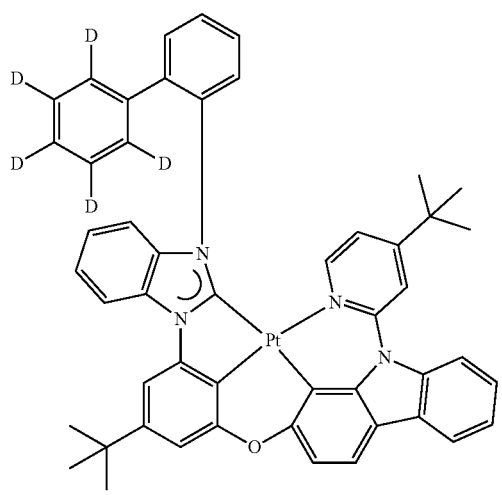
32
-continued
7
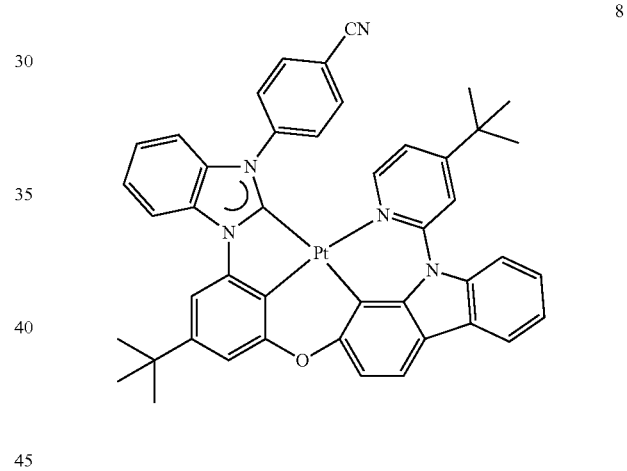
8
6
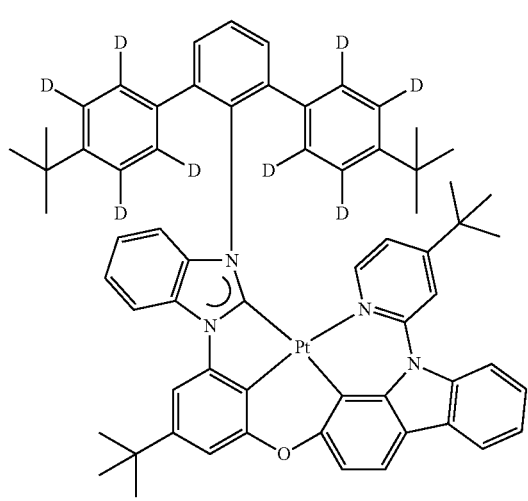
9
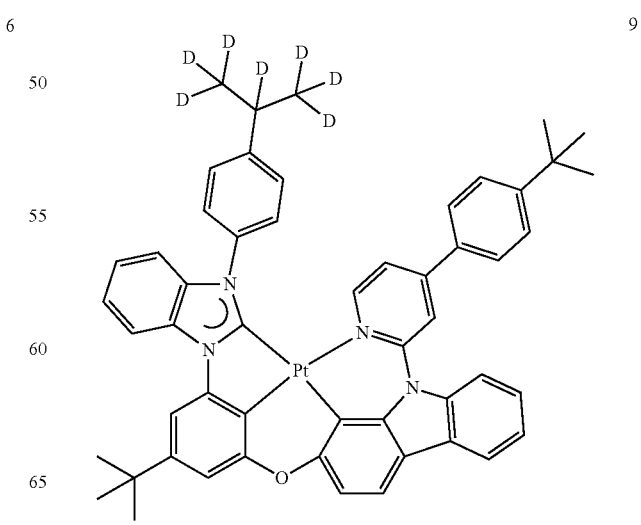

10
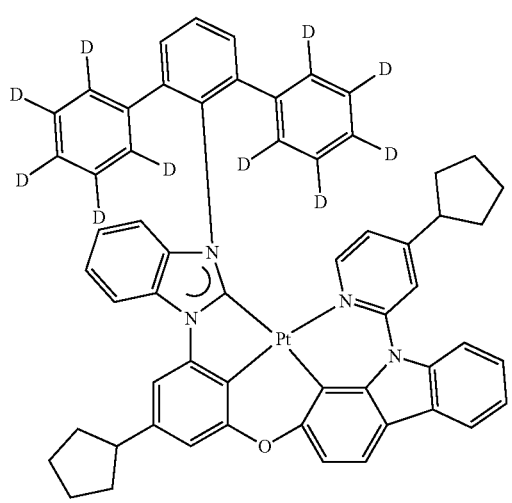
11
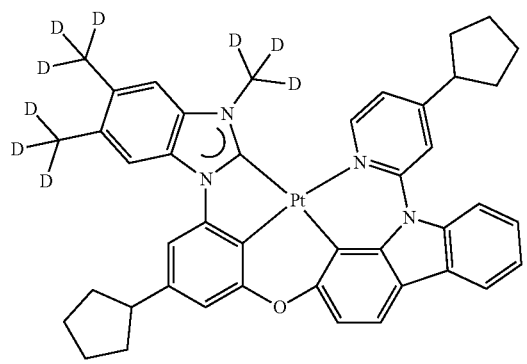
12
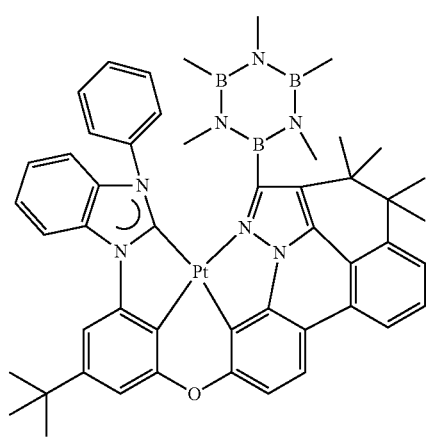
13
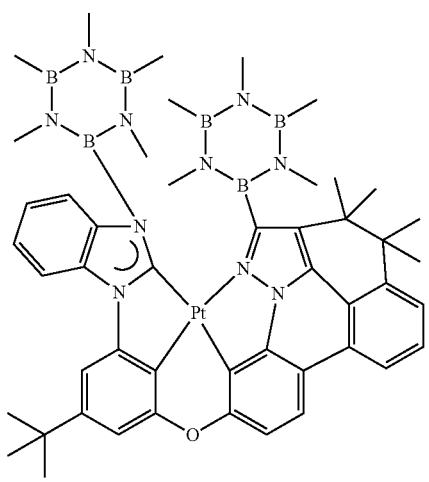
14
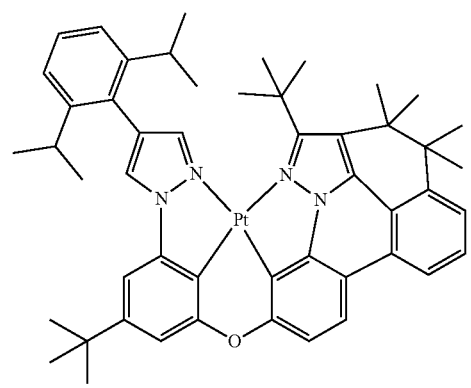
15
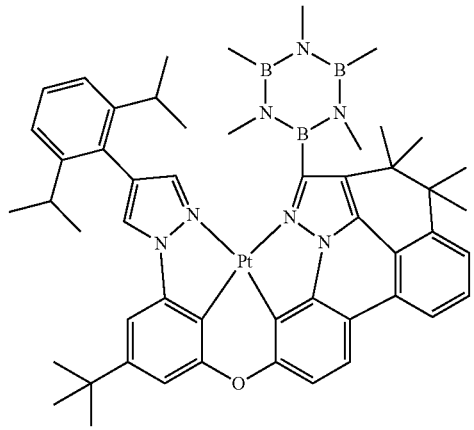

-continued

16
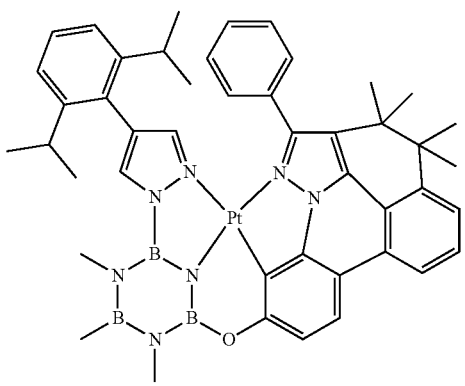

17
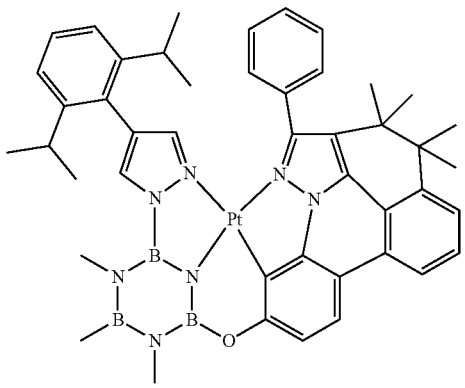

18
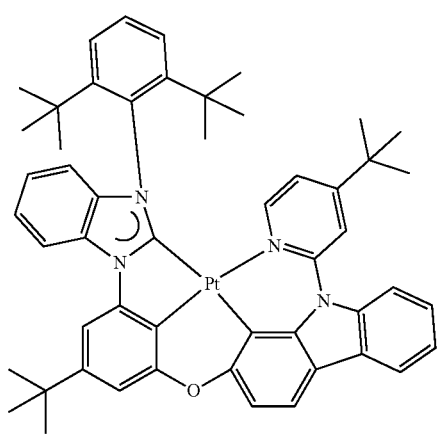

-continued

19
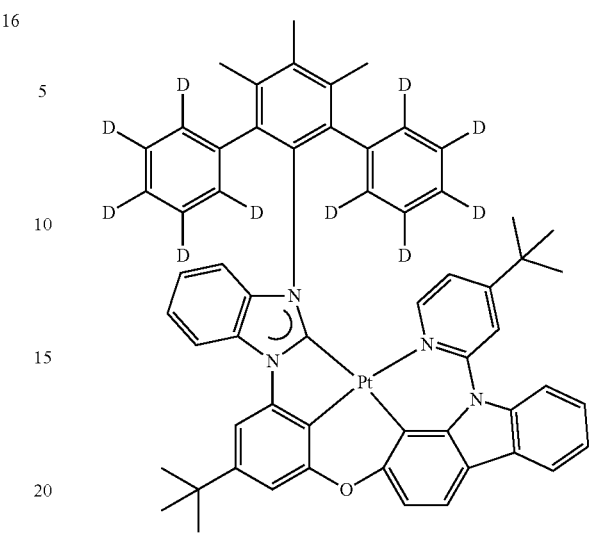

In the organic electroluminescence device illustrated in FIGS. 1 to 5, the emission layer EML may include a host and a dopant, and the emission layer EML may include the first compound, the second compound, and the third compound.

The first compound may be the organometallic compound. The organometallic compound may be a phosphorescence dopant. The emission layer EML may emit phosphorescence.

The second compound and the third compound may be hosts.

In some exemplary embodiments, the second compound may be represented by Formula 2 below:

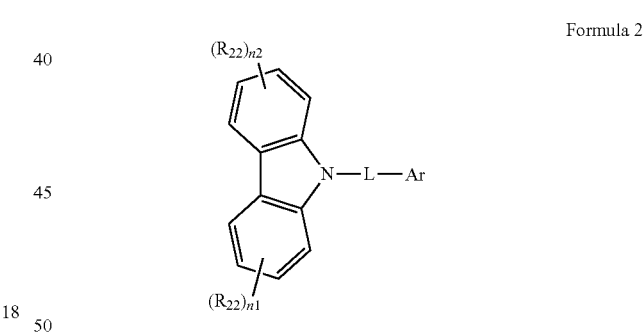

Formula 2

In Formula 2 above, Ar is a substituted or unsubstituted silyl group, a substituted or unsubstituted aryl group of 6 to 30 ring-forming carbon atoms, or a substituted or unsubstituted heteroaryl group of 3 to 30 ring-forming carbon atoms. For example, Ar may be an arylsilyl group, a substituted or unsubstituted phenyl group, a substituted or unsubstituted anthracene group, a substituted or unsubstituted triphenylene group, a substituted or unsubstituted fluorene group, a substituted or unsubstituted carbazole group, a substituted or unsubstituted dibenzofuran group, or a substituted or unsubstituted dibenzothiophene group. However, the exemplary embodiments are not limited thereto.

In Formula 2, L is a direct linkage, a substituted or unsubstituted arylene group having 6 to 30 ring-forming carbon atoms, or a substituted or unsubstituted heteroarylene group having 3 to 30 ring-forming carbon atoms. For example, L is a phenylene group, a biphenylene group, a divalent anthracene group. However, the exemplary embodiments are not limited thereto.

In Formula 2 above, $R_{21}$ and $R_{22}$ may be each independently a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, $R_{21}$ and $R_{22}$ may be each independently a substituted or unsubstituted phenyl group, or a substituted or unsubstituted carbazole group, In Formula 2 above, n1 and n2 are each independently an integer of 0 to 4.

In some exemplary embodiments, the second compound represented by Formula 2 may include at least one among the compounds represented by Compound Group H1 below:

Compound Group H1

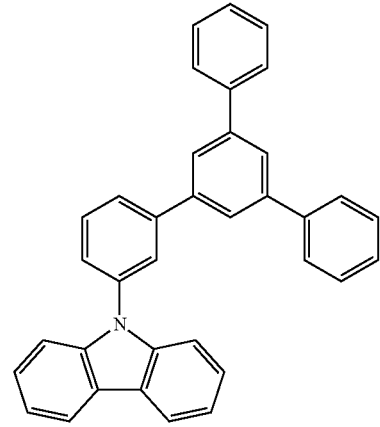

1-1

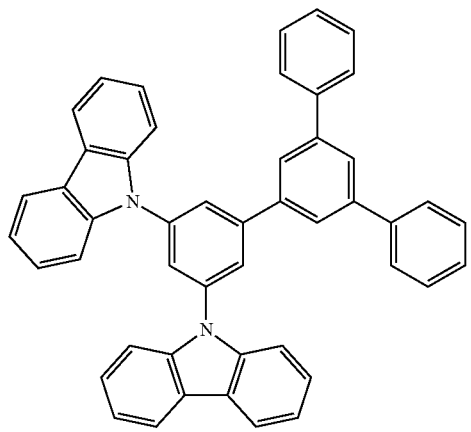

1-2

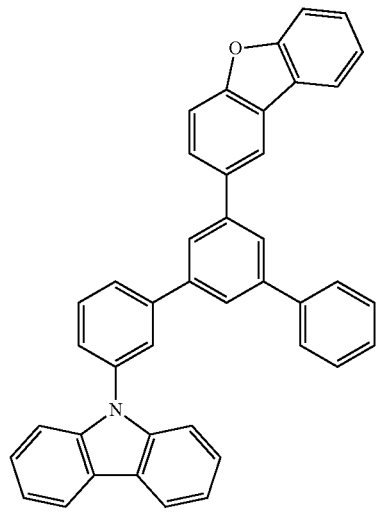

1-3

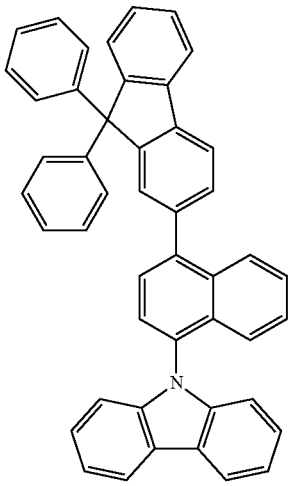

1-4

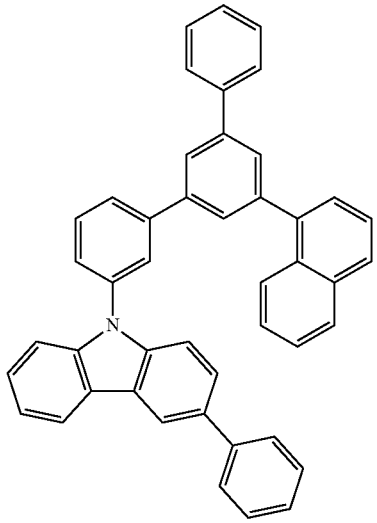

1-5

1-6
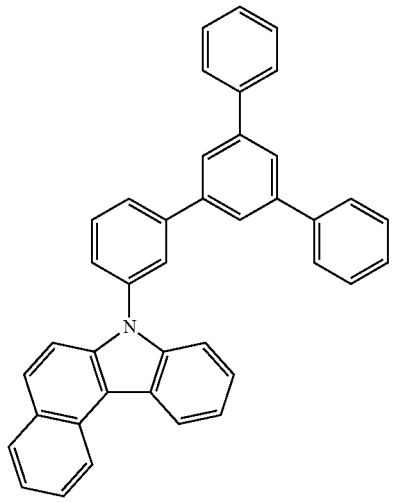
1-7
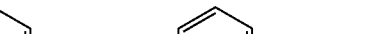
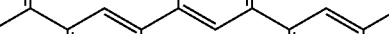
1-8
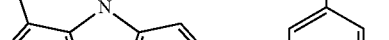
1-9
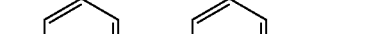
1-10
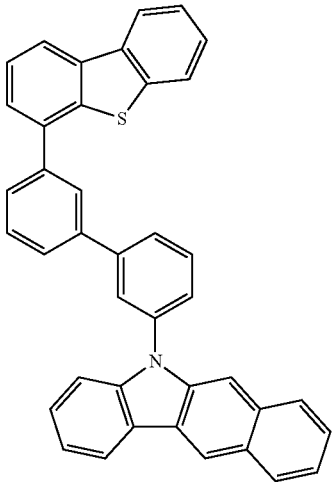
1-11
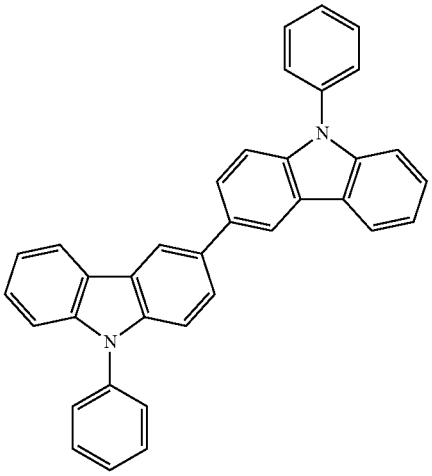
1-12
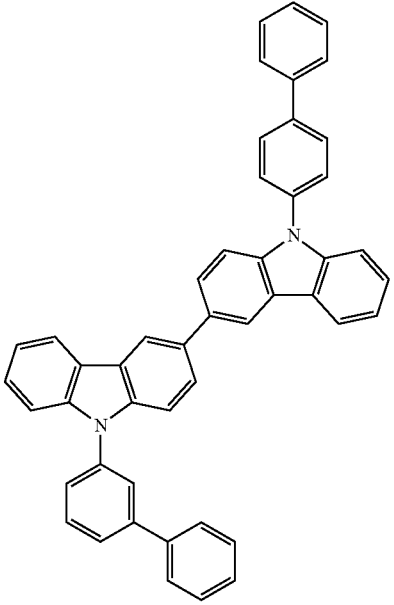

1-13
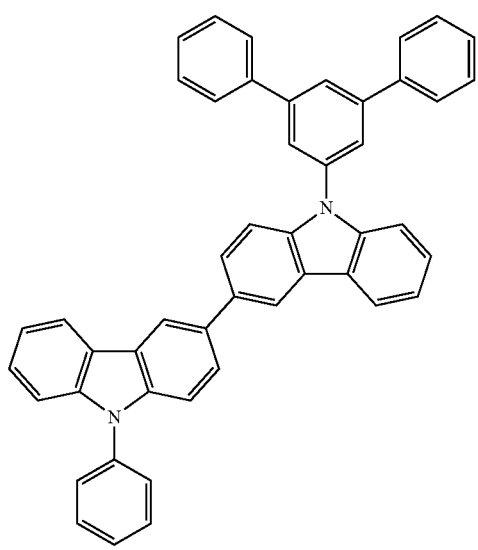
1-14
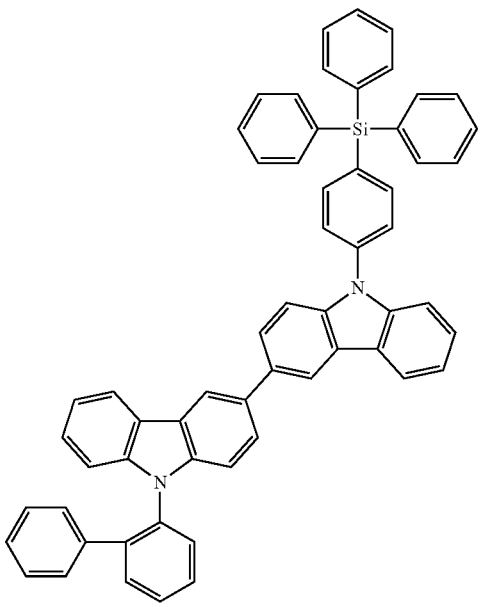
1-15
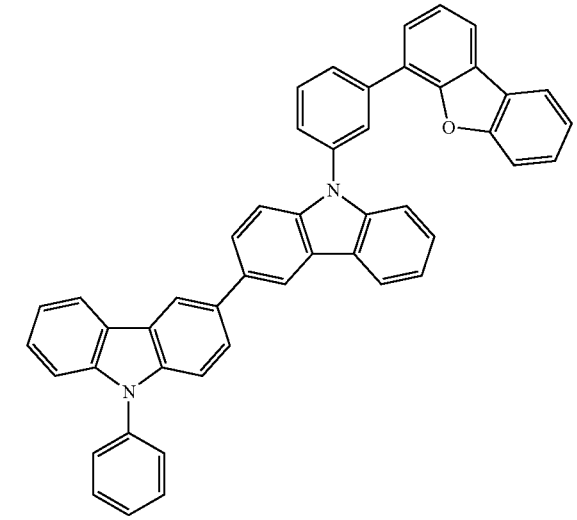
1-16
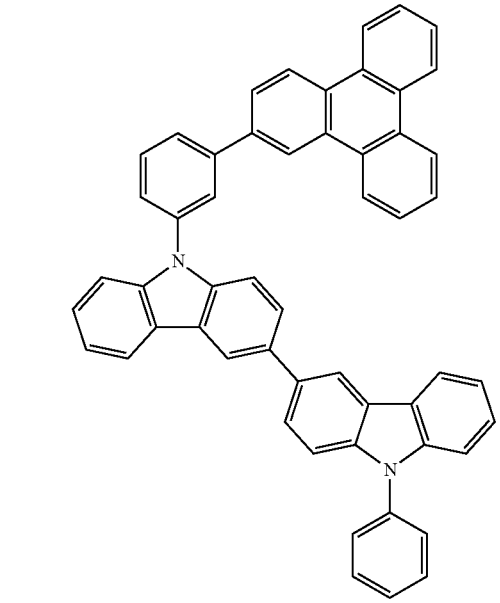
1-17
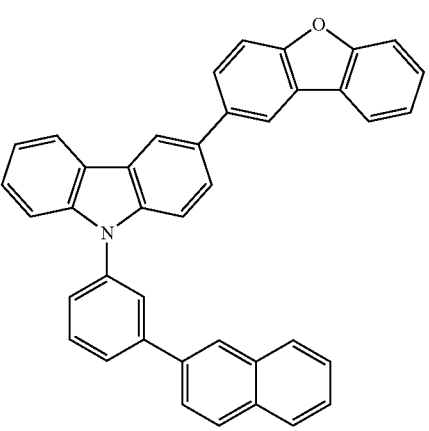

1-18

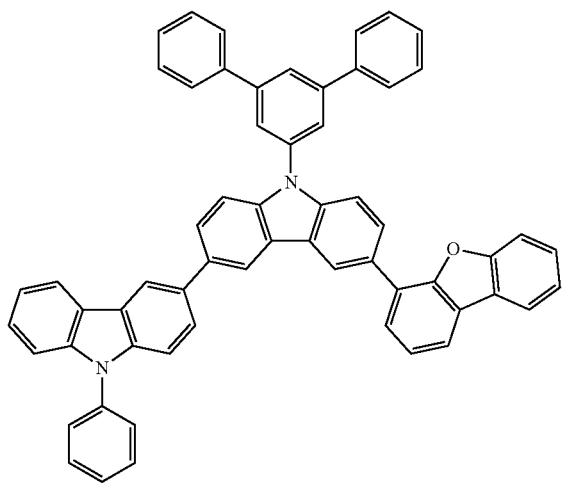

1-19

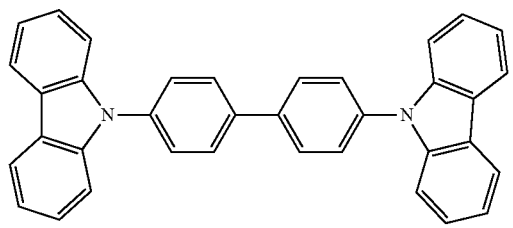

1-20

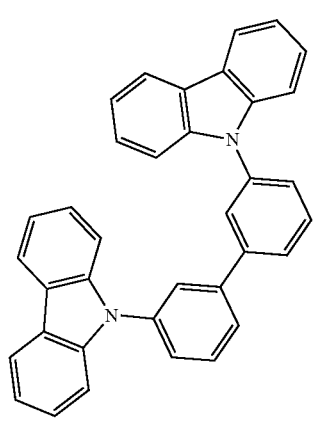

1-21

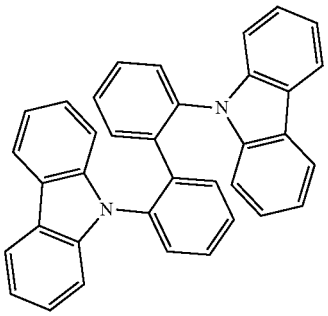

1-22

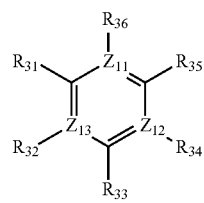

In some exemplary embodiments, the third compound may be represented by Formula 3 below:

Formula 3

$$\begin{array}{c} R_{36} \\ R_{31}\!-\!Z_{11}\!-\!R_{35} \\ R_{32}\!-\!Z_{13}\!-\!Z_{12}\!-\!R_{34} \\ R_{33} \end{array}$$

In Formula 3 above, $R_{31}$, $R_{32}$, $R_{33}$, $R_{34}$, $R_{35}$, and $R_{36}$ may be each independently a hydrogen atom, a deuterium atom, a cyano group, a substituted silyl group, a substituted or unsubstituted aryl group having 6 to 30 ring-forming carbon atoms, or a substituted or unsubstituted heteroaryl group having 3 to 30 ring-forming carbon atoms, or may be bonded to an adjacent group to form a ring. For example, $R_{31}$, $R_{32}$, $R_{33}$, $R_{34}$, $R_{35}$, and $R_{36}$ may be each independently a hydrogen atom, a methyl group, a substituted or unsubstituted phenyl group, or a substituted or unsubstituted carbazole group.

In Formula 3 above, $Z_{11}$, $Z_{12}$, and $Z_{13}$ are each independently C or N.

In some exemplary embodiments, the third compound represented by Formula 3 may include at least one among the compounds represented by Compound Group H2 below:
Compound Group H2
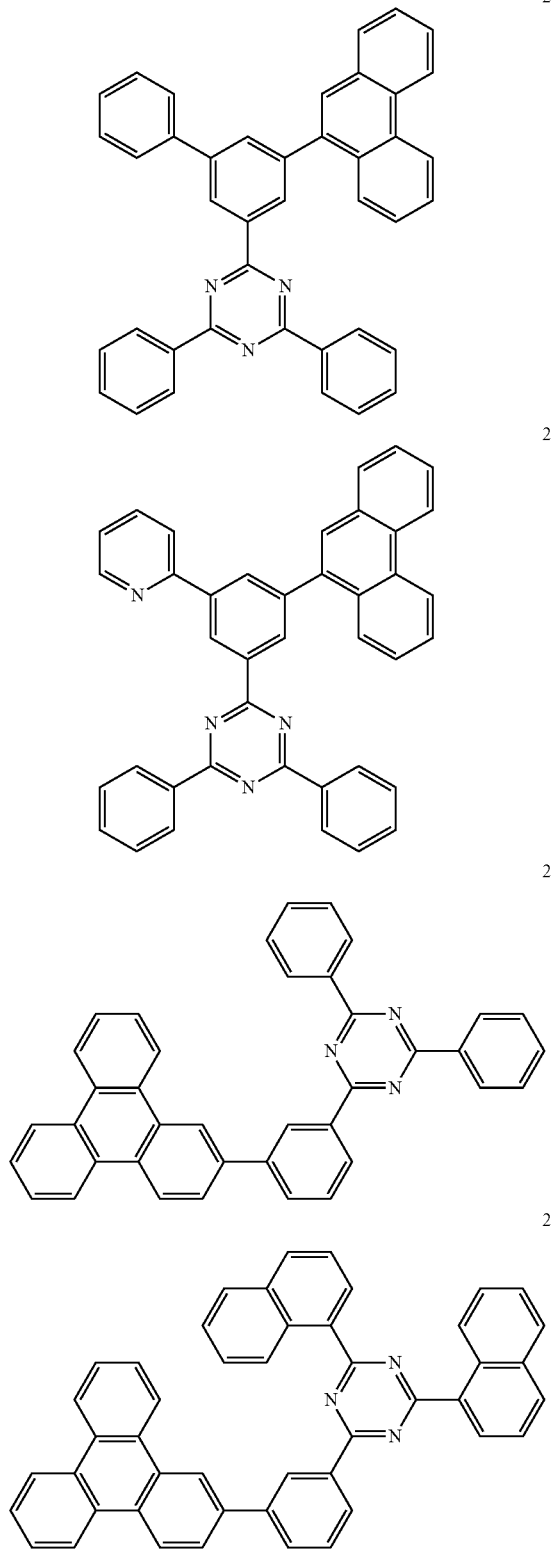
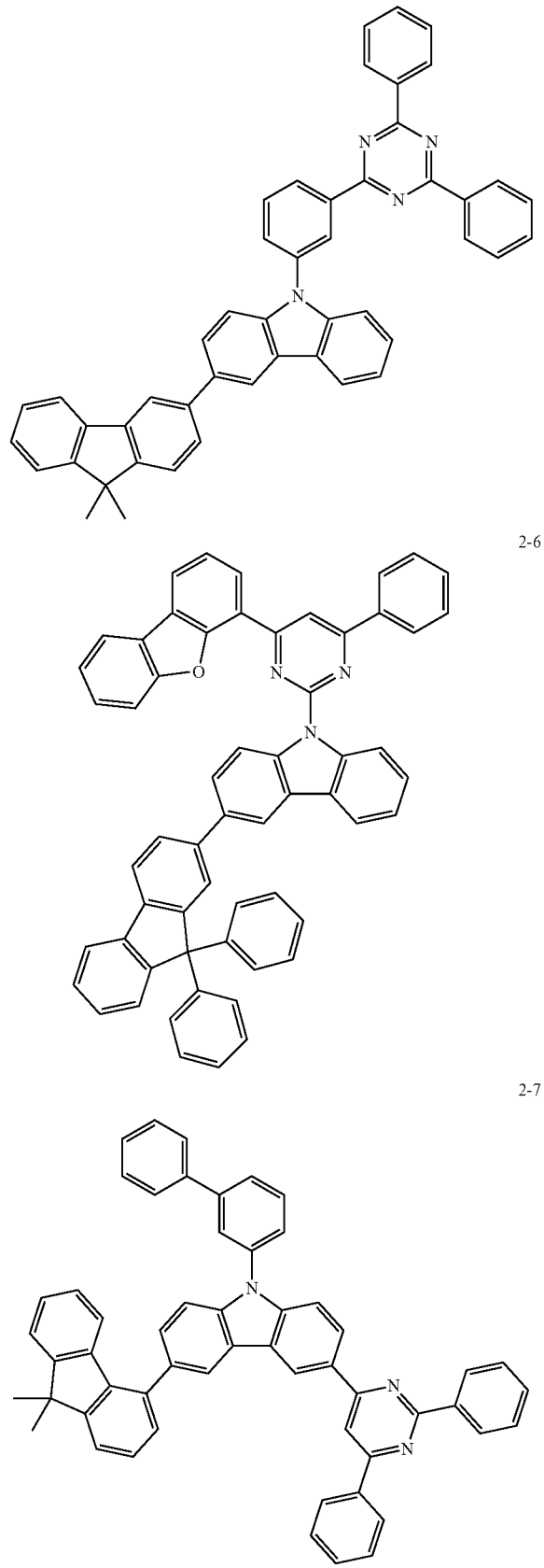

2-8
2-9
2-10
2-11
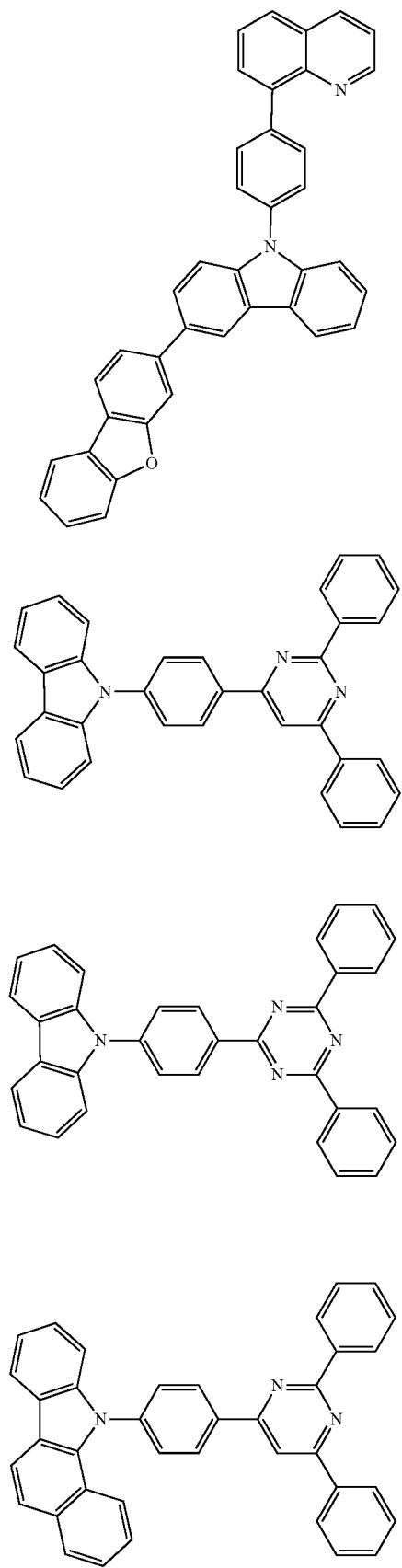
2-12
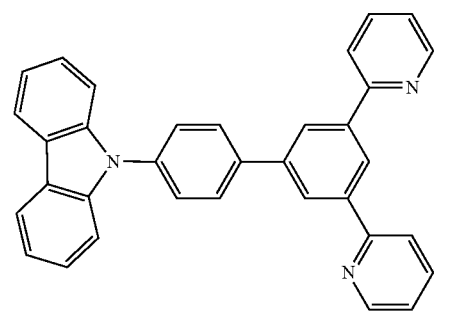
2-13
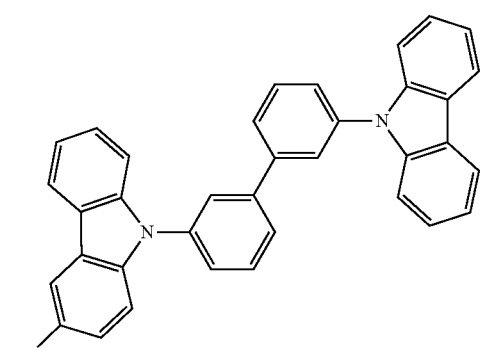
2-14
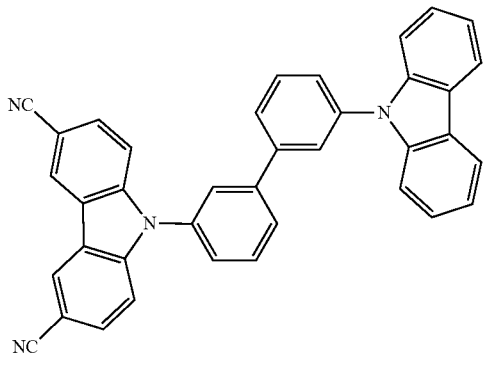
2-15
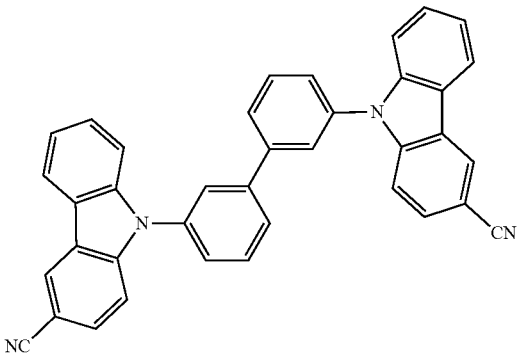

-continued
2-16
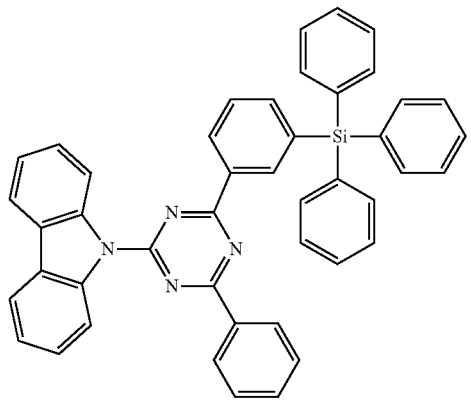
2-17
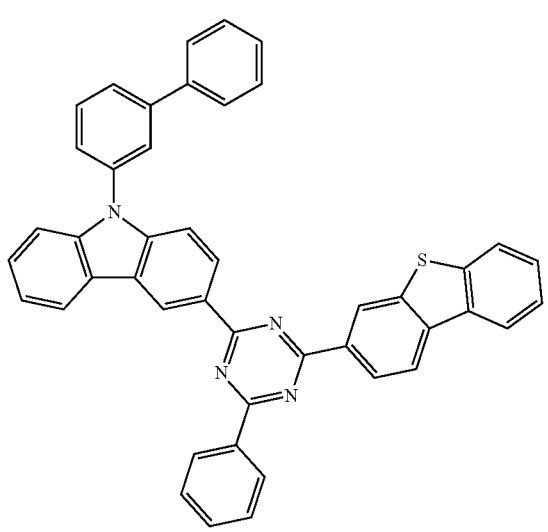
2-18
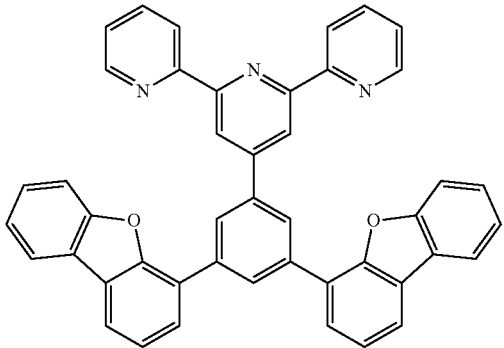
-continued
2-19
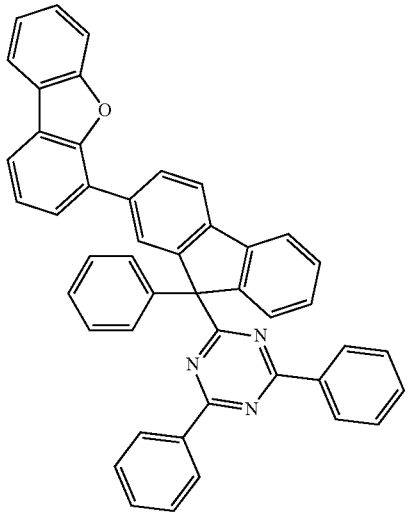
2-20
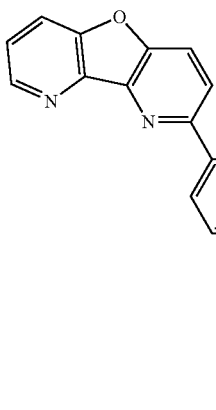
2-21
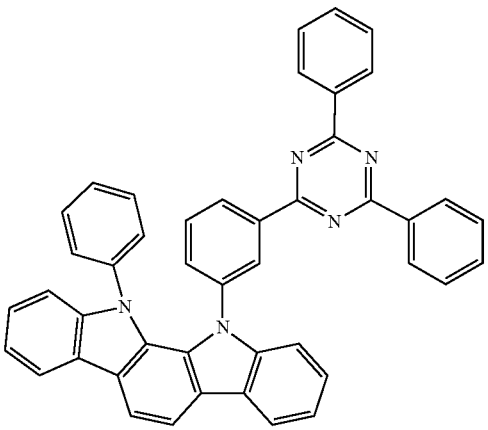

-continued
2-22
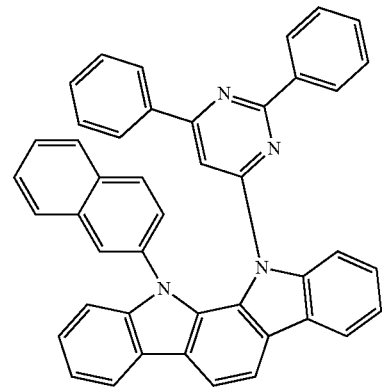
2-23
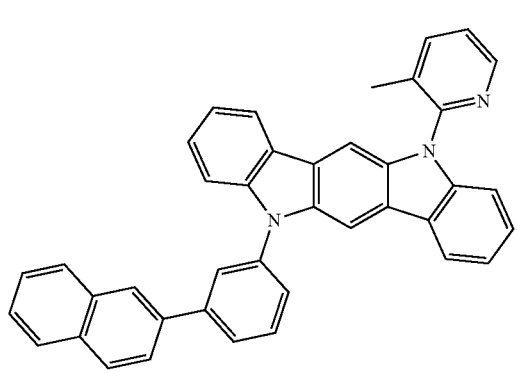
2-24
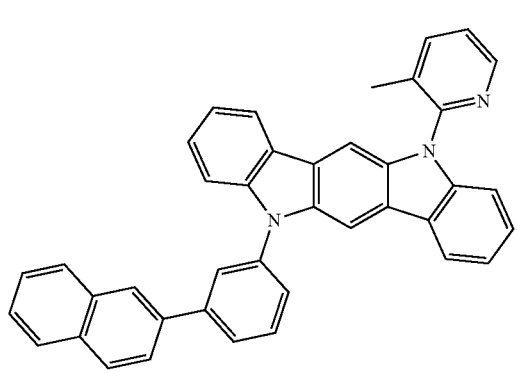
-continued
2-25
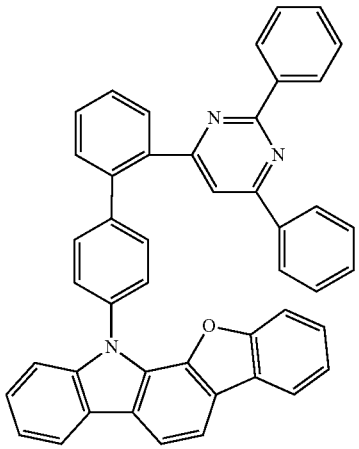
2-26
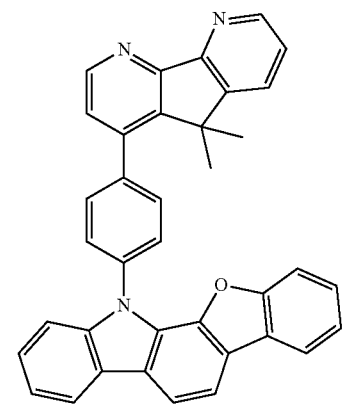
2-27
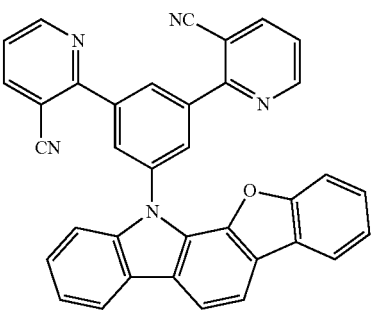
2-28
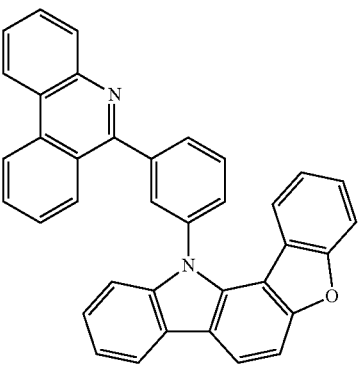

-continued 2-29

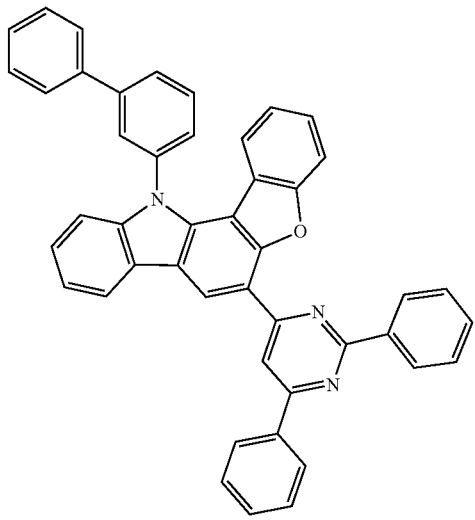

Compound Group F

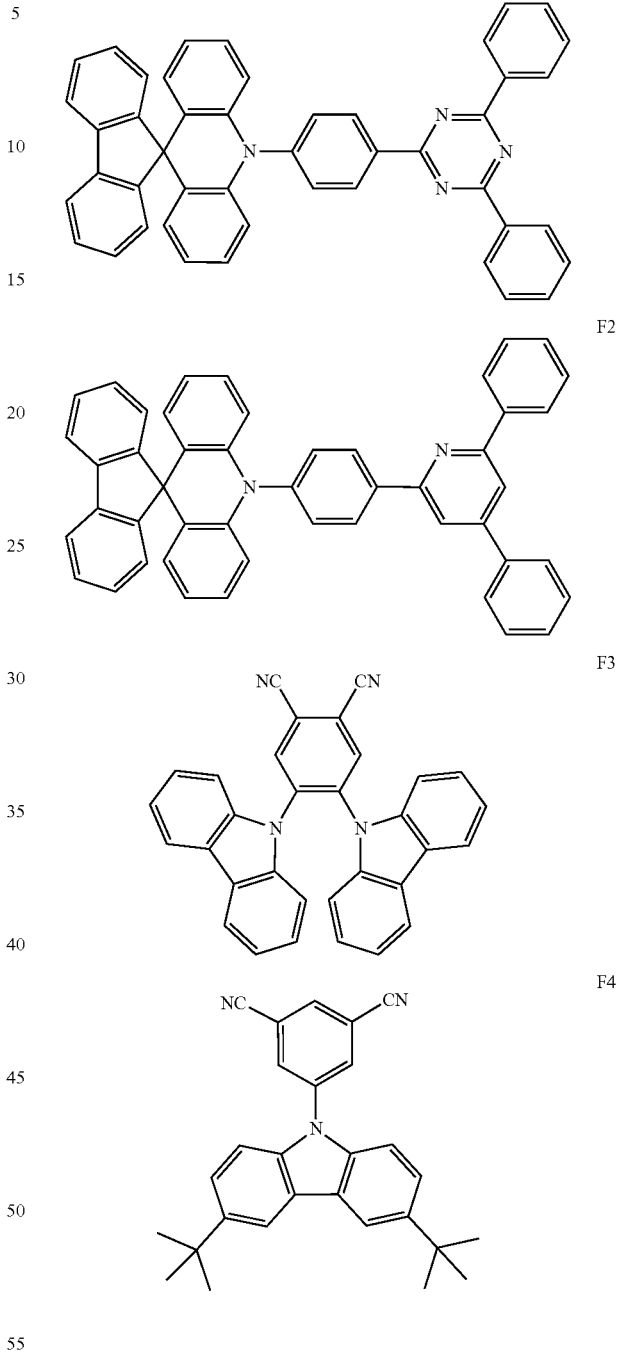

The organic electroluminescence device according to some exemplary embodiments includes the first compound as a dopant material and both the second compound and the third compound as a host material.

The emission layer EML may include one or two or more of the organometallic compounds of Compound Group 1 as described above. The emission layer EML may further include a known material in addition to the organometallic compound as described above.

The emission layer EML in the organic electroluminescence device may further include a known dopant material in addition to the organometallic compound as described above. In some exemplary embodiments, the emission layer EML may further include, as dopant materials, styryl derivatives (e.g., 1, 4-bis[2-(3-N-ethylcarbazoryl)vinyl]benzene (BCzVB), 4-(di-p-tolylamino)-4'-[(di-p-tolylamino)styryl] stilbene (DPAVB), and N-(4-((E)-2-(6-((E)-4-(diphenylamino)styryl)naphthalen-2-yl)vinyl)phenyl)-N-phenylbenzenamine (N-BDAVBi), perylene and the derivatives thereof (e.g., 2,5,8,11-tetra-t-butylperylene (TBP)), pyrene and the derivatives thereof (e.g., 1-dipyrene, 1,4-dipyrenylbenzene, 1,4-bis(N,N-diphenylamino)pyrene), etc.

The emission layer EML in the organic electroluminescence device may further include a known fluorescence material in addition to the organometallic compound as described above. For example, the fluorescence dopant compound of Compound Group F below may be included.

F6
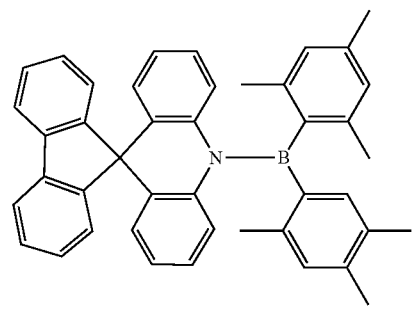
F7
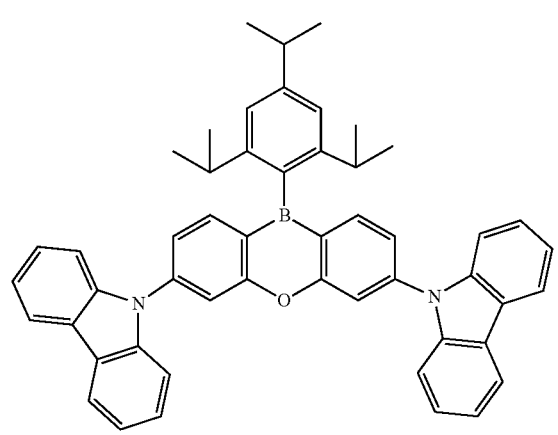
F8
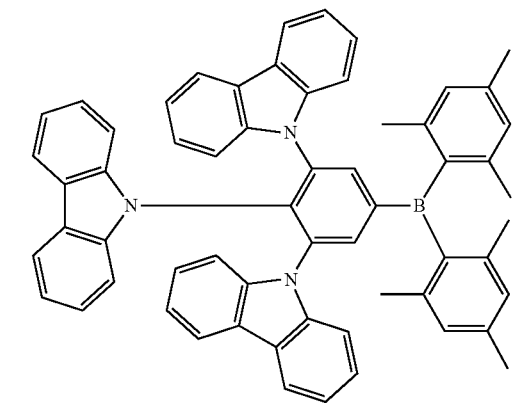
F9
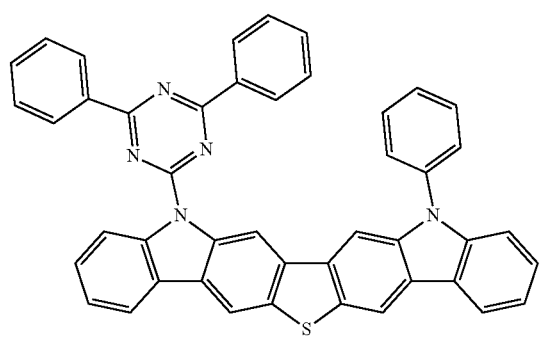
F10
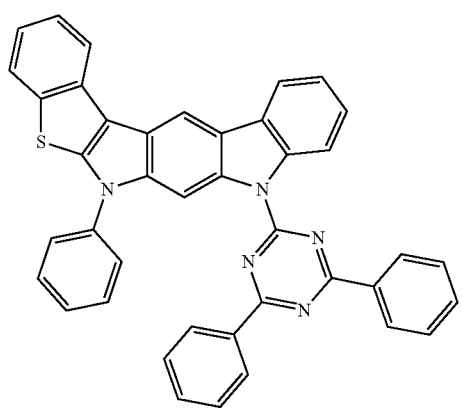
F11
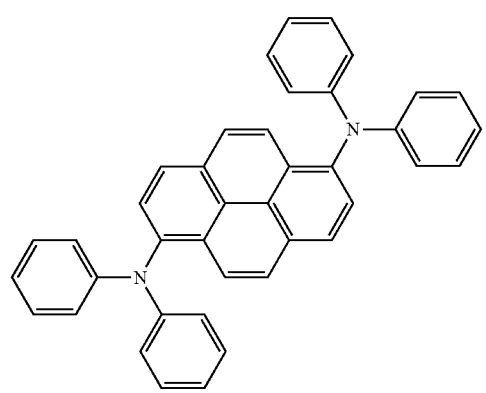
F12
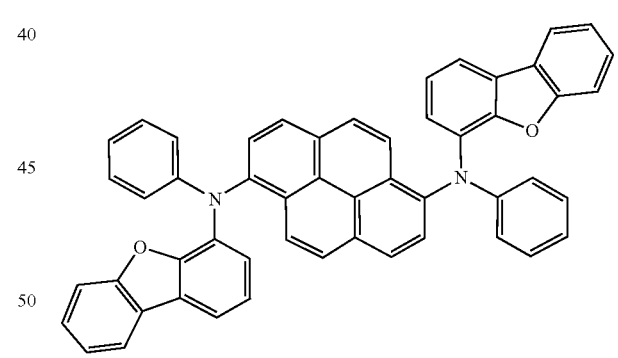
F13
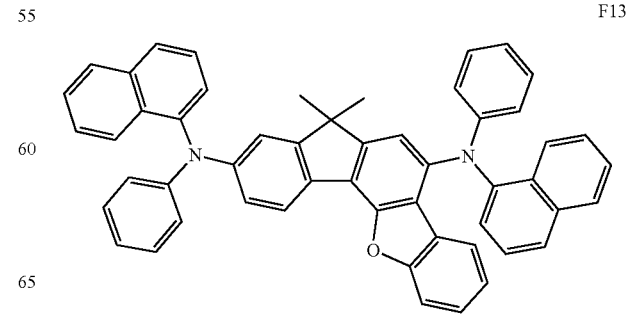

-continued
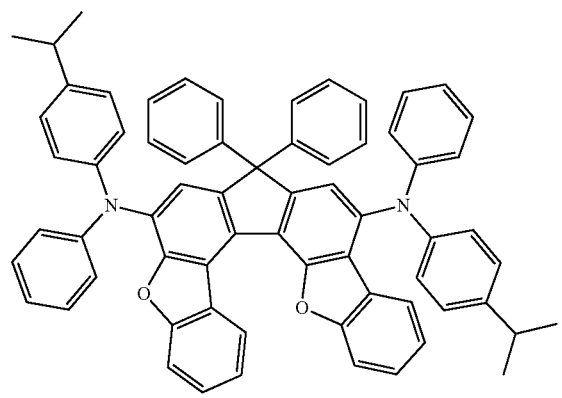
F14
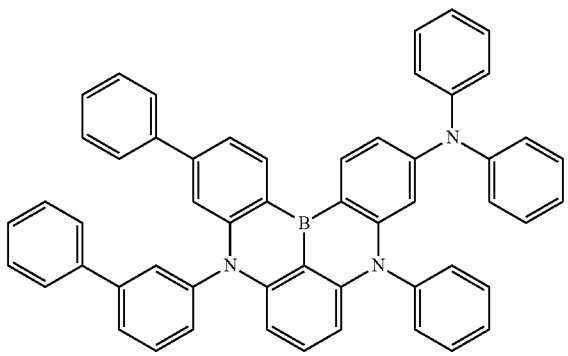
F18
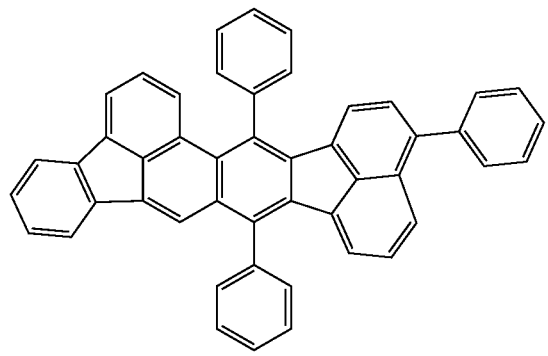
F15
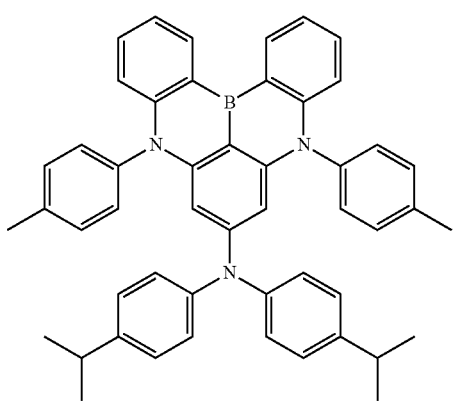
F19
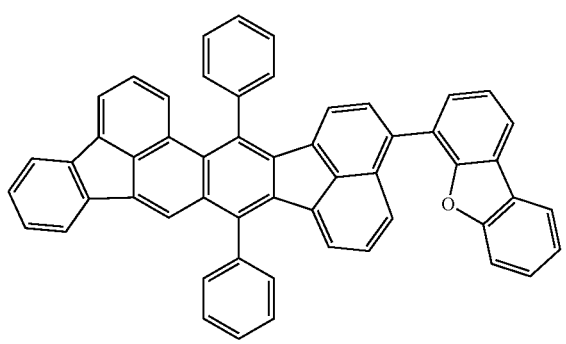
F16
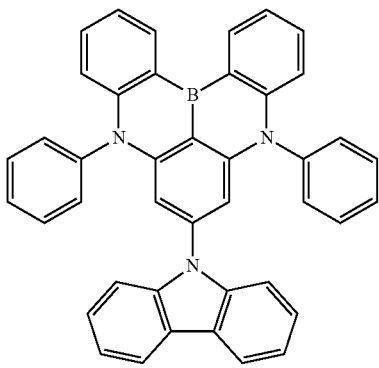
F20
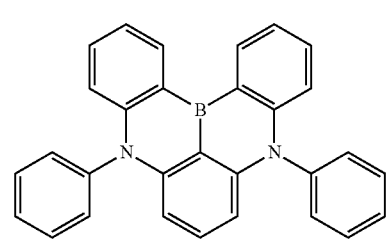
F17
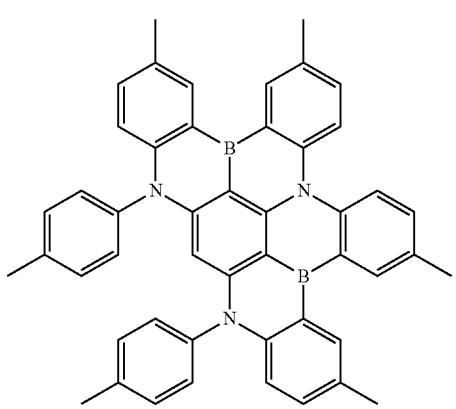
F21

-continued

F22

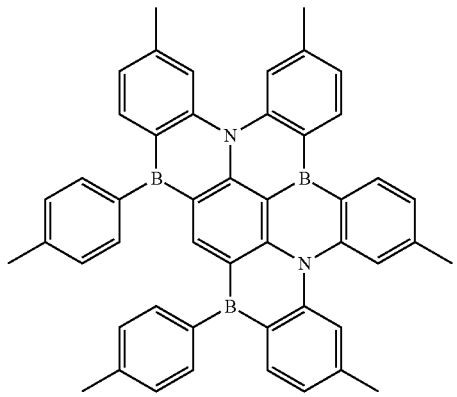

The emission layer EML may employ a general material known in the art as a host material without limitation. For example, the emission layer EML may include at least one of bis[2-(diphenylphosphino)phenyl] ether oxide (DPEPO), 1,3-bis(carbazol-9-yl)benzene (mCP), 2,8-bis(diphenylphosphoryl)dibenzo[b,d]furan (PPF), 4,4',4''-tris(carbazol-9-yl)-triphenylamine (TcTa), or 1,3,5-tris(N-phenylbenzimidazol-2-yl)benzene) (TPBi). However, the exemplary embodiments are not limited thereto, for example, tris(8-hydroxyquinolino)aluminum ($Alq_3$), 4,4'-bis(N-carbazolyl)-1,1'-biphenyl (CBP), poly(n-vinylcabazole) (PVK), 9,10-di(naphthalene-2-yl)anthracene (ADN), 4,4',4''-tris(carbazol-9-yl)-triphenylamine (TcTa), 1,3,5-tris(N-phenylbenzimidazole-2-yl)benzene (TPBi), 3-tert-butyl-9,10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenylcyclotriphosphazene (CP1), 1,4-bis(triphenylsilyl)benzene (UGH2), hexaphenylcyclotrisiloxane ($DPSiO_3$), octaphenylcyclotetra siloxane ($DPSiO_4$), 2,8-bis(diphenylphosphoryl)dibenzofuran (PPF), etc. may be further included as a host material.

In the organic electroluminescence device illustrated in FIGS. 1 to 5, the electron transport region ETR is provided on the emission layer EML. The electron transport region ETR may include at least one of an electron barrier reinforced layer BRL2, a hole blocking layer HBL, an electron transport layer ETL, or an electron injection layer EIL, but the exemplary embodiments are not limited thereto.

The electron transport region ETR may have a single layer formed of a single material, a single layer formed of a plurality of different materials, or a multilayer structure including a plurality of layers formed of a plurality of different materials.

For example, the electron transport region ETR may have a single layer structure of an electron injection layer EIL or an electron transport layer ETL, and may have a single layer structure formed of an electron injection material and an electron transport material. In addition, the electron transport region ETR may have a single layer structure formed of a plurality of different materials, or may have a structure in which an electron transport layer ETL/electron injection layer EIL, a hole blocking layer HBL/electron transport layer ETL/electron injection layer EIL, or an electron barrier reinforced layer BRL2/hole blocking layer HBL/electron transport layer ETL/an electron injection layer EIL are stacked in order from the emission layer EML, but the exemplary embodiments are not limited thereto. The thickness of the electron transport region ETR may be, for example, from about 1,000 Å to about 1,500 Å.

The electron transport region ETR may be formed using various methods such as a vacuum deposition method, a spin coating method, a cast method, a Langmuir-Blodgett (LB) method, an inkjet printing method, a laser printing method, a laser induced thermal imaging (LITI) method, etc.

When the electron transport region ETR includes the electron transport layer ETL, the electron transport region ETR may include an anthracene-based compound. However, the exemplary embodiments are not limited thereto, and the electron transport region may include, for example, tris(8-hydroxyquinolinato)aluminum ($Alq_3$), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,O8)-(1,1'-biphenyl-4-olato) aluminum (BAlq), berylliumbis(benzoquinolin-10-olate ($Bebq_2$), 9,10-di(naphthalene-2-yl)anthracene (ADN), or a mixture thereof. The thickness of the electron transport layers ETL may be from about 100 Å to about 1,000 Å, for example, from about 150 Å to about 500 Å. If the thickness of the electron transport layers ETL satisfies the above-described range, satisfactory electron transport characteristics may be obtained without a substantial increase in driving voltage.

If the electron transport region ETR includes the electron injection layer EIL, the electron transport region ETR may be formed using metal halides such as LiF, NaCl, CsF, RbCl, and RbI, lanthanum metals such as Yb, metal oxides such as $Li_2O$ and BaO, Lithium quinolate (Liq), etc., but the exemplary embodiments are not limited thereto. The electron injection layer EIL may also be formed of a mixture material of an electron transport material and an insulating organometallic salt. The organometallic salt may be a material having an energy band gap of about 4 eV or more. Specifically, the organometallic salt may include, for example, metal acetates, metal benzoates, metal acetoacetates, metal acetylacetonates or metal stearates. The thickness of the electron injection layers EIL may be from about 1 Å to about 100 Å, and from about 3 Å to about 90 Å. If the thickness of the electron injection layers EIL satisfies the above-described range, satisfactory electron injection properties may be obtained without a substantial increase in driving voltage.

The electron transport region ETR may include a hole blocking layer HBL as described above. The hole blocking layer HBL may include, for example, at least one of 2,9-dimethyl-4,7-diphenyl-1,10-phenanthroline (BCP), or 4,7- diphenyl-1,10-phenanthroline (Bphen), but the exemplary embodiments are not limited thereto.

In addition, the electron transport region ETR may include an electron barrier reinforced layer BRL2. The electron barrier reinforced layer BRL2 may reduce an energy gap between the emission layer and the electron transport region ETR. In addition, the electron barrier reinforced layer BRL2 may have higher electron mobility than the hole blocking layer HBL. In some exemplary embodiments, the electron barrier reinforced layer BRL2 may include at least one among Compound 2-1 to Compound 2-29 of Compound Group H2, but the exemplary embodiments are not limited thereto.

The second electrode EL2 is provided on the electron transport region ETR. The second electrode EL2 may be a common electrode or a negative electrode. The second electrode EL2 may be a transmissive electrode, a transflective electrode, or a reflective electrode. When the second electrode EL2 is the transmissive electrode, the second electrode EL2 may be formed of transparent metal oxides, for example, the ITO, IZO, ZnO, ITZO, etc.

When the second electrode EL2 is the transflective electrode or the reflective electrode, the second electrode EL2 may include Ag, Mg, Cu, Al, Pt, Pd, Au, Ni, Nd, Ir, Cr, Li, Ca, LiF/Ca, LiF/Al, Mo, Ti, or a compound thereof or a mixture thereof (for example, a mixture of Ag and Mg). Alternatively, the first electrode EL1 may have a multilayer structure including a reflective layer or a transflective layer formed of the above-described materials, and a transparent conductive layer formed of the ITO, IZO, ZnO, ITZO, etc.

The second electrode EL2 may be connected with an auxiliary electrode. When the second electrode EL2 is connected to the auxiliary electrode, the resistance of the second electrode EL2 may decrease.

A capping layer (CPL) may be further disposed on the second electrode EL2 of the organic electroluminescence device of some exemplary embodiments. The capping layer (CPL) may include a multilayer or a single layer.

The capping layer CPL may be an organic layer or an inorganic layer. For example, when the capping layer CPL includes an inorganic material, the inorganic material may include an alkaline metal compound such as LiF, an alkaline earth metal compound such as $MgF_2$, SiON, a $SiN_x$, a $SiO_y$, etc.

For example, when the capping layer CPL includes an organic material, the organic material may include 2,2'-Dimethyl-N,N'-di-[(1-naphthyl)-N,N'-diphenyl]-1,1'-biphenyl-4,4'-diamine (α-NPD), NPB, TPD, m-MTDATA, $Alq_3$, copper(II) phthalocyanine (CuPc), N4,N4,N4',N4'-tetra(biphenyl-4-yl)biphenyl-4,4'-diamine (TPD15), 4,4',4''-tris(carbazol sol-9-yl)triphenylamine (TCTA), etc., or an epoxy resin, or acrylate such as methacrylate. However, the exemplary embodiments are not limited thereto, and the organic material may also include Compounds P1 to P5 below.

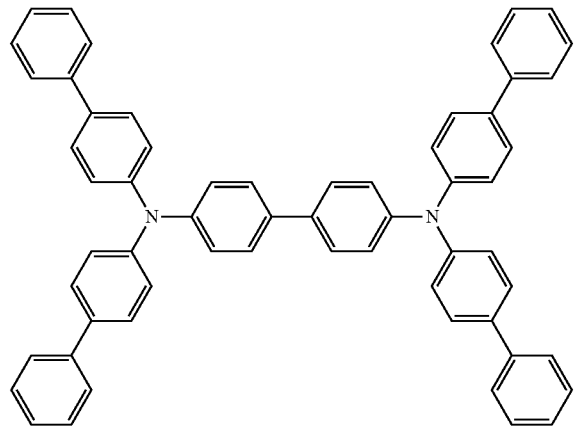

P1

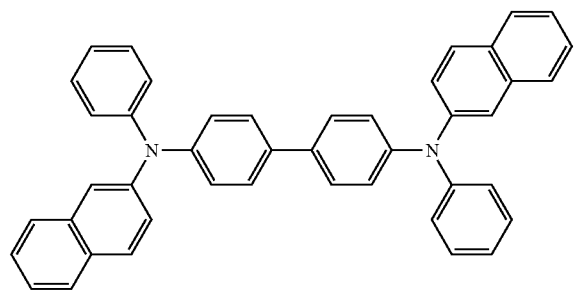

P2

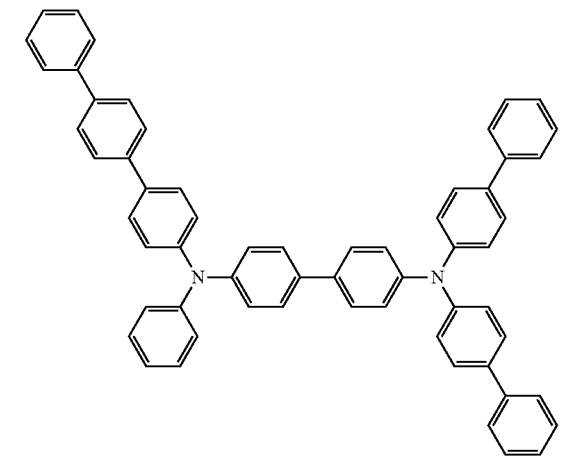

P3

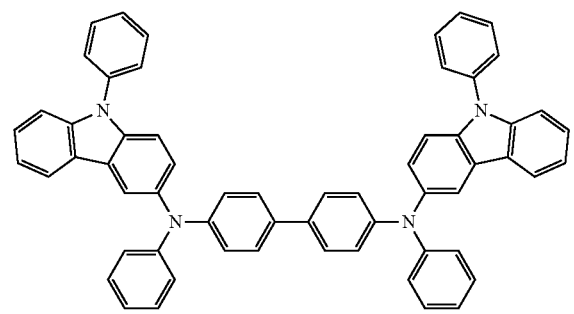

P4

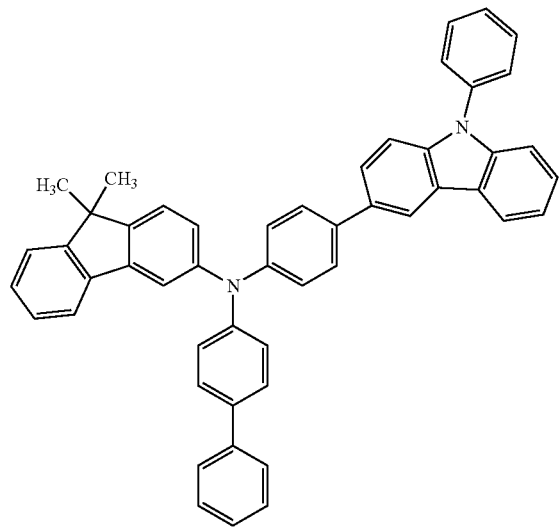

P5

The organic electroluminescence device may also include the above-described organometallic compound in at least one organic layer disposed between the first electrode EL1 and the second electrode EL2, or the capping layer CPL disposed on the second electrode EL2.

The organic electroluminescence device constructed according to the principles and exemplary embodiments of the invention includes a substituent, although not wanting to be bound by theory, causing a steric hindrance so that intermolecular interaction may be reduced and the stability of molecule may be increased. When the organometallic compound made according to the principles and exemplary embodiments of the invention is used in the emission u) layer, the organic electroluminescence device may exhibit improved device life time and low drive voltage characteristics.

Hereinafter, with reference to Examples and Comparative Examples, an organometallic compound made according to some exemplary embodiments, an organic electroluminescence device of some exemplary embodiments, and an organometallic compound used therein will be described in detail. In addition, Examples shown below are illustrated only for the understanding of the invention, and the scope of the invention is not limited thereto.

EXAMPLES

1. Synthesis of Organometallic Compound

An organometallic compound according to an exemplary embodiment may be synthesized, for example, as follows. However, exemplary embodiments of synthetic methods of the organometallic compound are not limited thereto.

Synthetic Example 1: Synthesis of Compound 1

Reaction Scheme 1

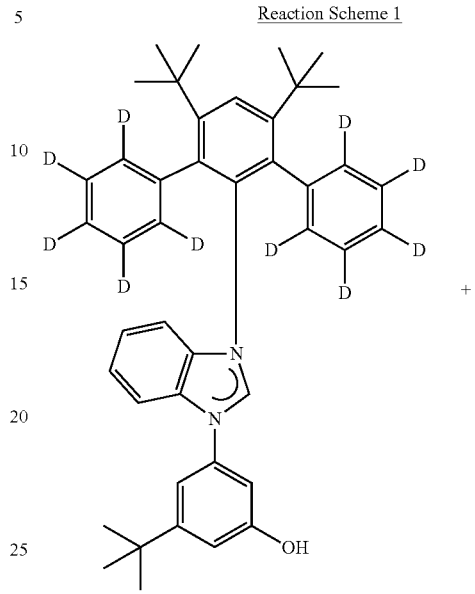

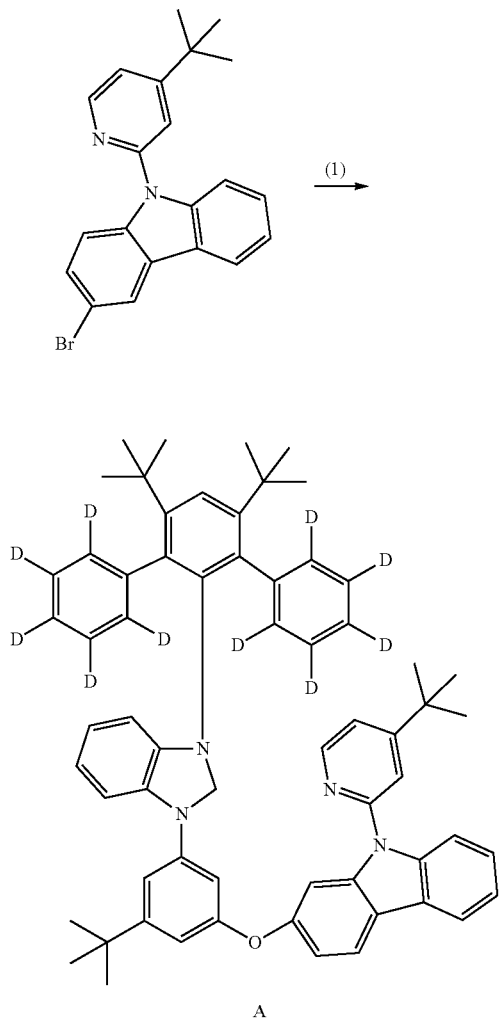

A

-continued

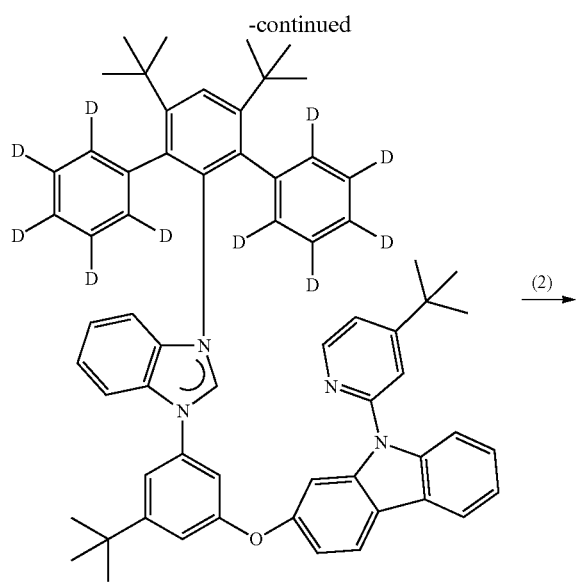

(2) →

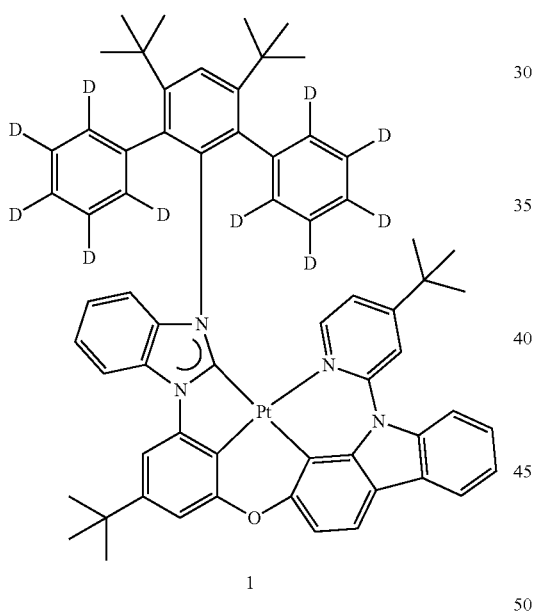

1

(1) Synthesis of Intermediate A 3-(tert-butyl)-5-(3-(4',6'-di-tert-butyl-[1,1': 3',1''-terphenyl]-2'-yl-2,2'',3,3'',4,4'',5,5'',6,6''-d10)-2,3-dihydro-1H-benzo[d]imidazol-1-yl)phenol (1 eq), 3-bromo-9-(4-(tert-butyl)pyridin-2-yl)-9H-carbazole (1 eq), iodo-copper (0.1 equivalent (eq)), potassium phosphate (2.0 eq), and L-proline (0.1 eq) were added to 100 mL of a dimethyl formamide solvent, heated to 120° C., and stirred for 12 hours. The reactant was extracted with dichloromethane and distilled water. The organic layer was washed three times with distilled water, dried with magnesium sulfate, filtered, and concentrated under reduced pressure. The concentrated solution was separated by column chromatography to obtain Intermediate A in 68% yield.

HRMS for $C_{64}H_{56}D_{10}N_4O$ [M]+: calculated (calcd): 917, found: 916

(2) Synthesis of Compound 1

Synthesized Intermediate A above, sodium acetate (3.0 eq), and dichloro(1,5-cyclooctadiene)platinum(II) (Pt(COD)Cl$_2$) (1.1 eq) were suspended in a 1,4-dioxane solvent. The reaction mixture was heated to 120° C. and stirred for 12 hours. After the reaction was completed, the solvent was removed under reduced pressure. The resultant was purified by column chromatography to obtain Compound 1 in 40% yield.

HRMS for $C_{64}H_{53}D_{10}N_4OPt$ [M]+: calcd: 1109, found: 1108

Elemental Analysis for calcd: C, 69.29; H, 6.63; N, 5.05; O, 1.44; Pt, 17.58

Synthetic Example 2: Synthesis of Compound 2

Reaction Scheme 2

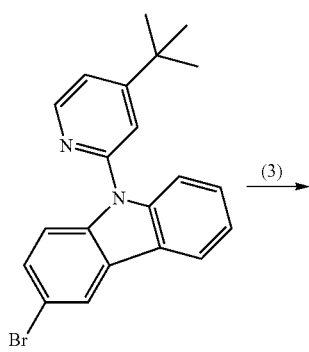

(3) →

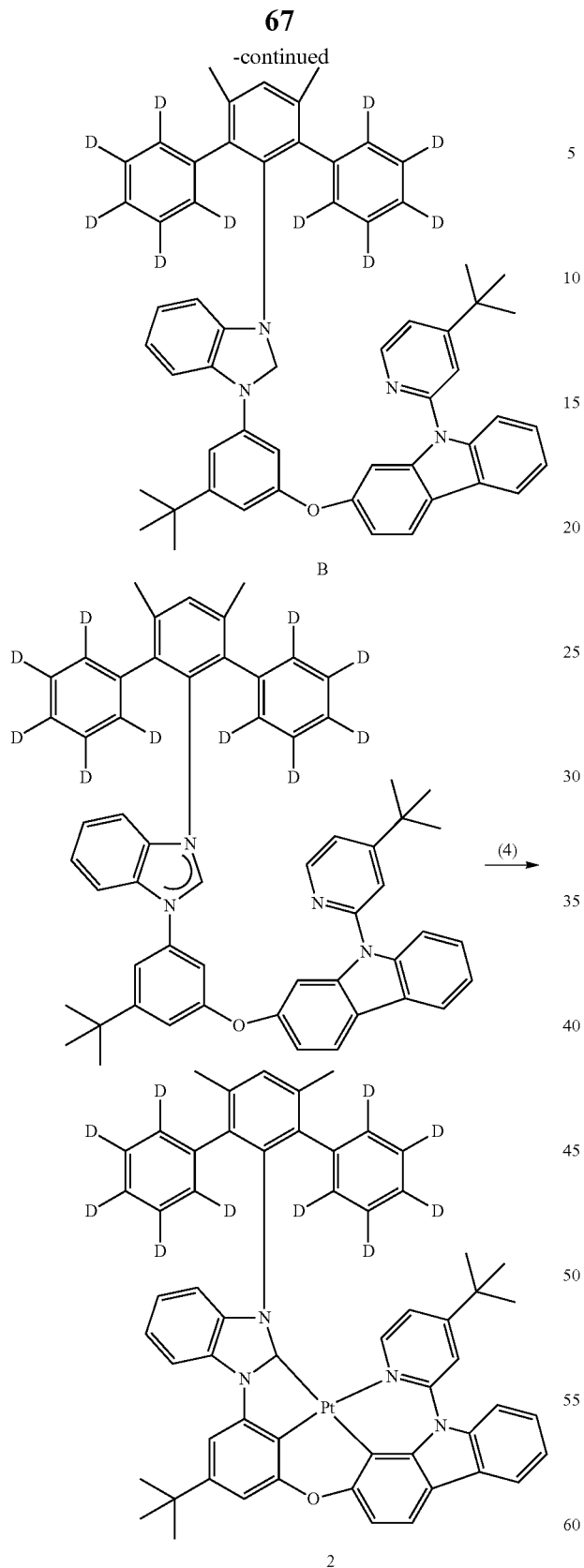

B

2

(3) Synthesis of Intermediate B

Intermediate B was synthesized in the same manner as in the synthesis of Intermediate A, except that 3-(tert-butyl)-5-(3-(4',6'-dimethyl-[1,1':3',1''-terphenyl]-2'-yl-2,2'',3,3'',4,4'',5,5'',6,6''-d10)-2,3-dihydro-1H-benzo[d]imidazol-1-yl)phenol was used instead of 3-(tert-butyl)-5-(3-(4',6'-di-tert-butyl-[1,1': 3',1''-terphenyl]-2'-yl-2,2'',3,3'',4,4'',5,5'',6,6''-d10)-2,3-dihydro-1H-benzo[d]imidazol-1-yl)phenol in the synthesis of Intermediate A.

HRMS for $C_{58}H_{44}D_{10}N_4O$ [M]+: calcd: 833, found: 832

(4) Synthesis of Compound 2

Synthesized Intermediate B above, sodium acetate (3.0 eq), and dichloro(1,5-cyclooctadiene)platinum(II) (Pt(COD)Cl$_2$) (1.1 eq) were suspended in a 1,4-dioxane solvent. The reaction mixture was heated to 120° C. and stirred for 12 hours. After the reaction was completed, the solvent was removed under reduced pressure. The resultant was purified by column chromatography to obtain Compound 2 in 37% yield.

HRMS for $C_{58}H_{41}D_{10}N_4OPt$ [M]+: calcd: 1025, found: 1024

Elemental Analysis for calcd: C, 67.95; H, 6.00; N, 5.46; O, 1.56; Pt, 19.03

Synthetic Example 3: Synthesis of Compound 6

Reaction Scheme 3

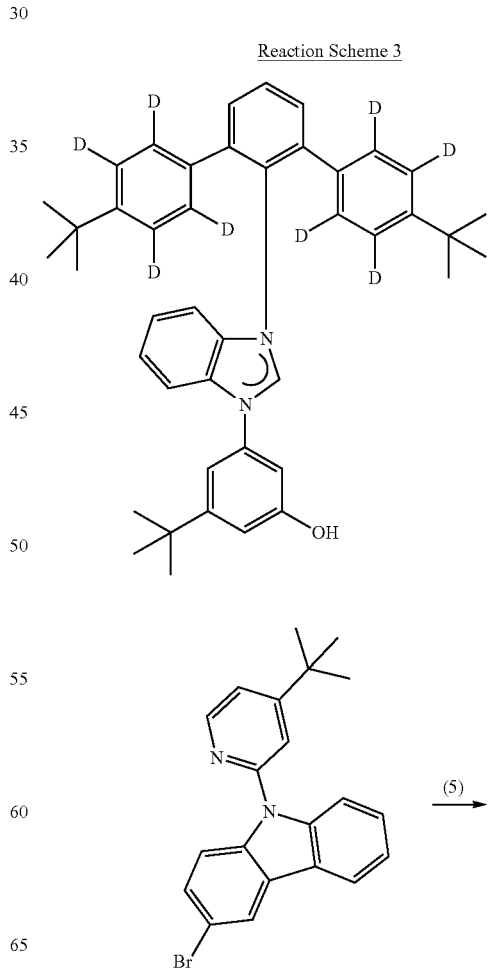

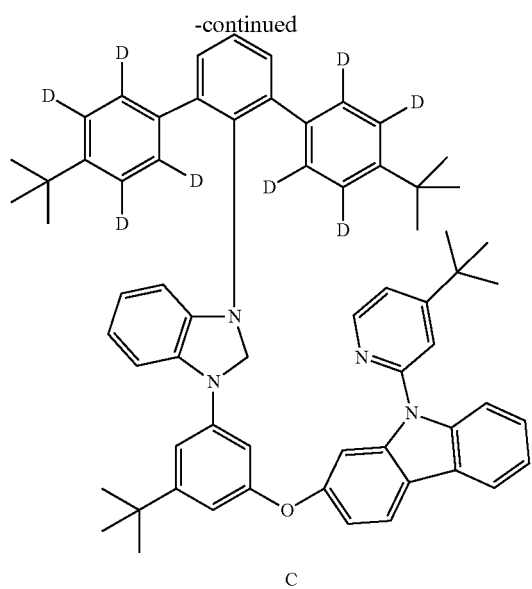

C

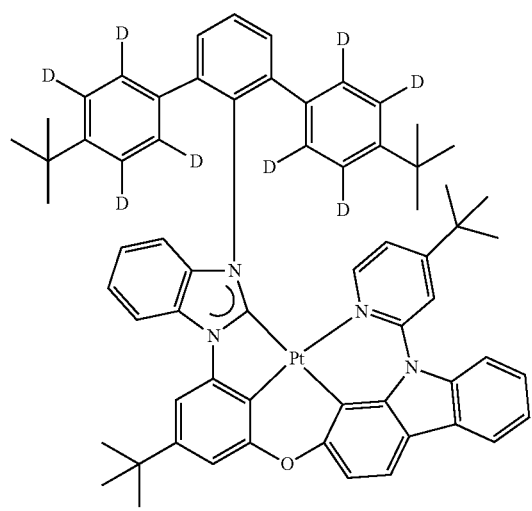

6

(5) Synthesis of Intermediate C

Intermediate C was synthesized in the same manner as in the synthesis of Intermediate A, except that 3-(tert-butyl)-5-(3-(4,4''-di-tert-butyl-[1,1': 3',1''-terphenyl]-2'-yl-2,2'',3,3'',5,5'',6,6''-d8)-2,3-dihydro-1H-benzo[d]imidazol-1-yl) phenol was used instead of 3-(tert-butyl)-5-(3-(4',6'-di-tert-butyl-[1,1': 3',1''-terphenyl]-2'-yl-2,2'',3,3'',4,4'',5,5'',6,6''-d10)-2,3-dihydro-1H-benzo[d]imidazol-1-yl)phenol in the synthesis of Intermediate A.

HRMS for $C_{64}H_{58}D_8N_4O$ [M]+: calcd: 915, found: 914

(6) Synthesis of Compound 6

Synthesized Intermediate B above, sodium acetate (3.0 eq), and dichloro(1,5-cyclooctadiene)platinum(II) (Pt(COD)Cl$_2$) (1.1 eq) were suspended in a 1,4-dioxane solvent. The reaction mixture was heated to 120° C. and stirred for 12 hours. After the reaction was completed, the solvent was removed under reduced pressure. The resultant was purified by column chromatography to obtain Compound 6 in 41% yield.

HRMS for $C_{64}H_{55}D_8N_4OPt$ [M]+: calcd: 1107, found: 1106

Elemental Analysis for calcd: C, 69.42; H, 6.46; N, 5.06; O, 1.44; Pt, 17.62

Synthetic Example 4: Synthesis of Compound 1-3

Reaction Scheme 4

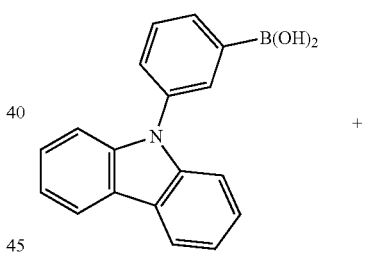

+

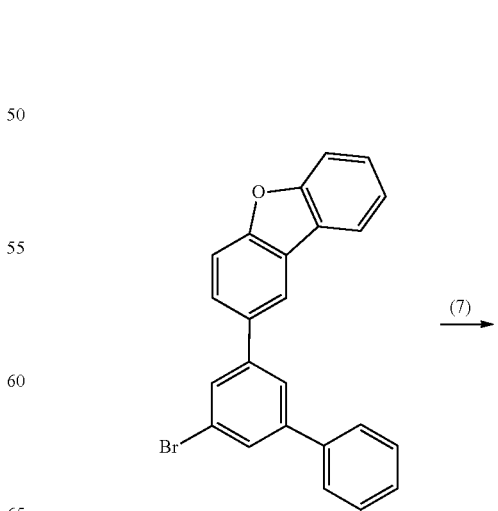

71

-continued

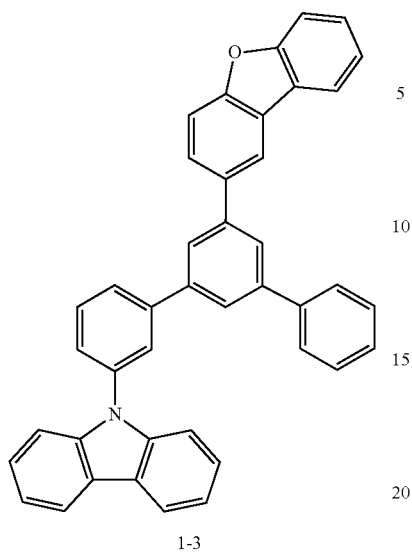

1-3

(7) Synthesis of Compound 1-3

Pd(dba)$_3$ (0.03 eq), (t-Bu)$_3$P (0.06 eq), and toluene (0.1M 1 eq) were added to the flask in which 2-(5-bromo-[1,1'-biphenyl]-3-yl)dibenzo[b,d]furan (1 eq) and (3-(9H-carbazol-9-yl)phenyl)boronic acid (1.2 eq) were put, and then refluxed and stirred for 8 hours. The reaction mixture was cooled to room temperature, extracted with methylene chloride, and washed with distilled water. The reaction mixture was dried with MgSO$_4$, distilled under reduced pressure, and the residues were separated by column chromatography to obtain Compound 1-3 (yield 81.7%).

HRMS for C$_{42}$H$_{27}$NO [M]+: calcd: 561, found: 560

Elemental Analysis for calcd: C, 89.81; H, 4.85; N, 2.49; O, 2.85

Synthetic Example 5: Synthesis of Compound 2-13

72

-continued

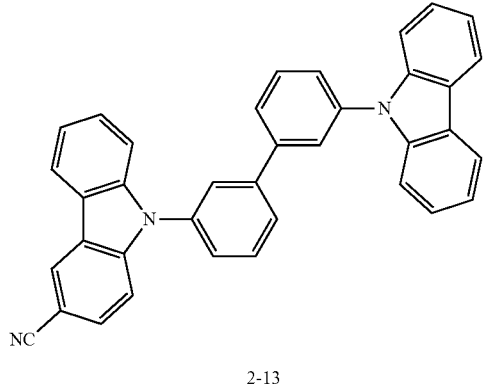

2-13

(8) Synthesis of Compound 2-13

9-(3'-bromo-[1,1'-biphenyl]-3-yl)-9H-carbazole (1 eq) and 9H-carbazole-3-carbonitrile (1.2 eq) were dissolved in 500 mL of toluene. Pd(dba)$_3$ (0.03 eq), (t-Bu)$_3$P (0.06 eq), and toluene (0.1M 1 eq) were added thereto and refluxed and stirred for 8 hours. The reaction mixture was cooled to room temperature, extracted with methylene chloride, and washed with distilled water. The reaction mixture was dried with MgSO$_4$, distilled under reduced pressure, and the residues were separated by column chromatography to obtain Compound 2-13 (yield 81.7%).

HRMS for C$_{37}$H$_{23}$N$_3$ [M]+: calcd: 509, found: 508

Elemental Analysis for calcd: C, 87.20; H, 4.55; N, 8.25

Synthetic Example 6: Synthesis of Compound 2-16

Reaction Scheme 6

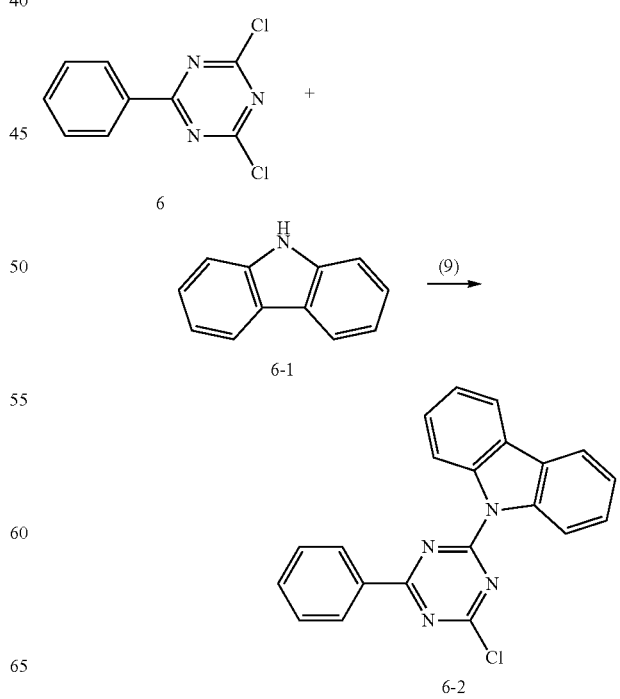

Reaction Scheme 5

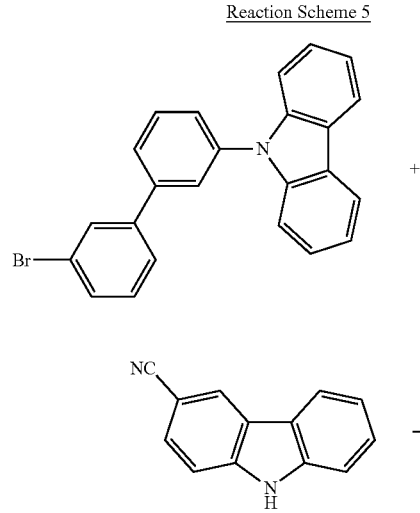

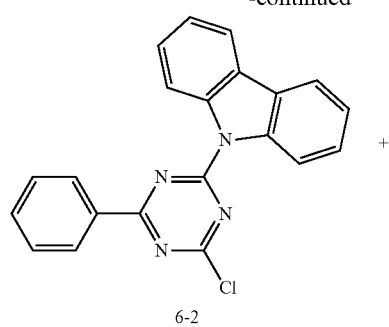

6-2

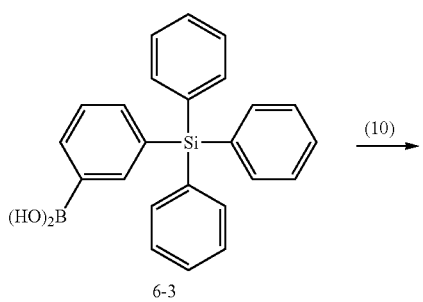

6-3

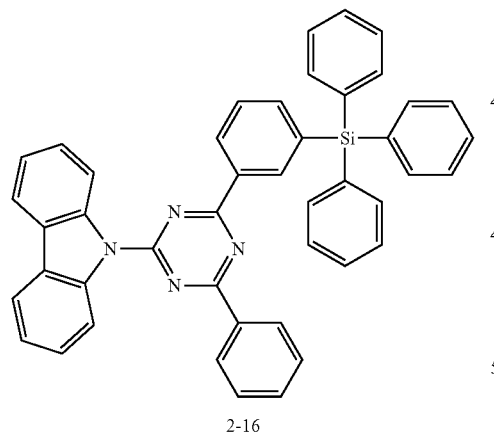

2-16

(9) Synthesis of Intermediate 6-2

Pd(dba)₃ (0.03 eq), (t-Bu)₃P (0.06 eq), and toluene (0.1M 1 eq) were added to the flask in which 9H-carbazole (1 eq) and 2,4-dichloro-6-phenyl-1,3,5-triazine (0.9 eq) were put, and then refluxed and stirred for 8 hours. The reaction mixture was cooled to room temperature, extracted with methylene chloride, and washed with distilled water. The reaction mixture was dried with MgSO₄, distilled under reduced pressure, and the residues were separated by column chromatography to obtain Intermediate Compound 6-2 (yield 88.44%).

HRMS for $C_{21}H_{13}ClN_4$ [M]+: calcd: 356, found: 355

(10) Synthesis of Compound 2-16

9-(4-chloro-6-phenyl-1,3,5-triazin-2-yl)-9H-carbazole (1 eq) and (3-(triphenylsilyl)phenyl)boronic acid (1.2 eq) were dissolved in 500 mL of toluene. Pd(PPh₃)₄ (0.02 eq) was added thereto. Further, 400 mL of Toluene and 70 mL of 2M K₂CO₃ saturated solution were added thereto and refluxed and stirred for 5 hours. After the reaction was completed, the resultant was washed and extracted with 400 mL of methylene chloride and 150 mL of distilled water, the solvent was removed, and the resulting solid was purified by column chromatography to obtain desired Compound 2-16 (yield 77.6%).

HRMS for $C_{45}H_{32}N_4Si$ [M]+: calcd: 656, found: 656

Elemental Analysis for calcd: C, 82.28; H, 4.91; N, 8.53; Si, 4.28

2. Calculation of Energy Level of Organometallic Compound

The first compound, the second compound (or the first host), and the third compound (or the second host) used in each of the emission layers of the light emitting devices of Examples and Comparative Examples are listed in Table 1.

TABLE 1

|  | Emission layer | | |
| --- | --- | --- | --- |
|  | First compound | Second compound | Third compound |
| Example 1 | 1 | 1-3 | 2-16 |
| Example 2 | 2 | 1-3 | 2-16 |
| Example 3 | 6 | 1-3 | 2-16 |
| Example 4 | 1 | 1-3 | 2-13 |
| Comparative Example 1 | C1 | 1-3 | 2-16 |

Example First Compound

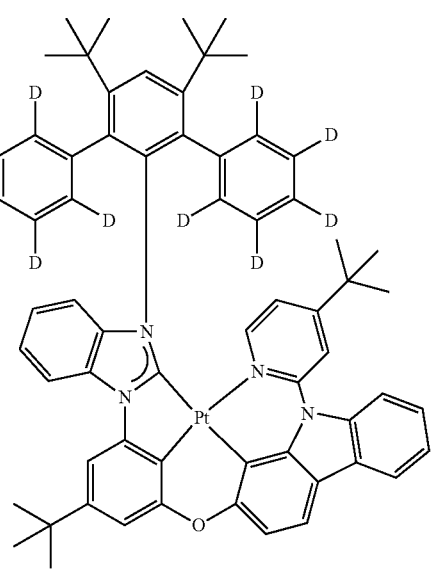

1

-continued
2
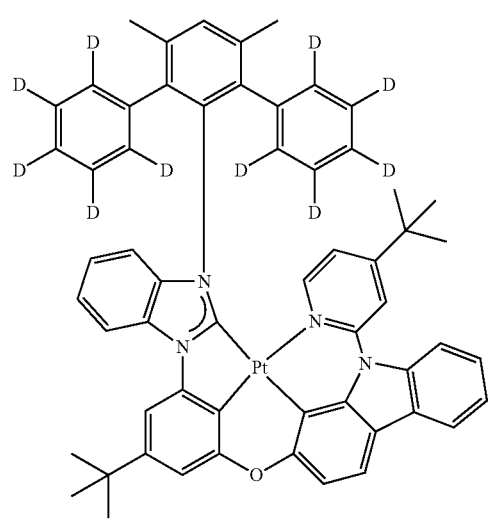
Example Second Compound
1-3
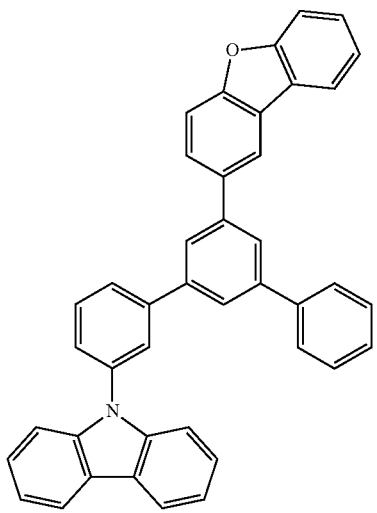
Example Third Compound
2-13
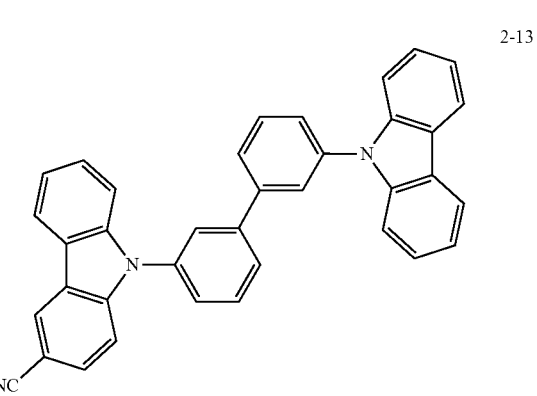
6
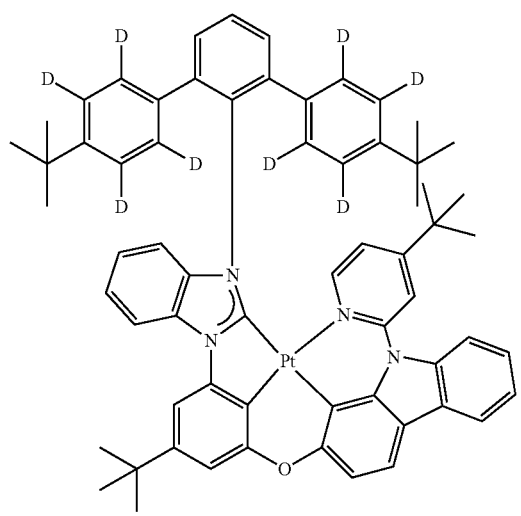
2-16
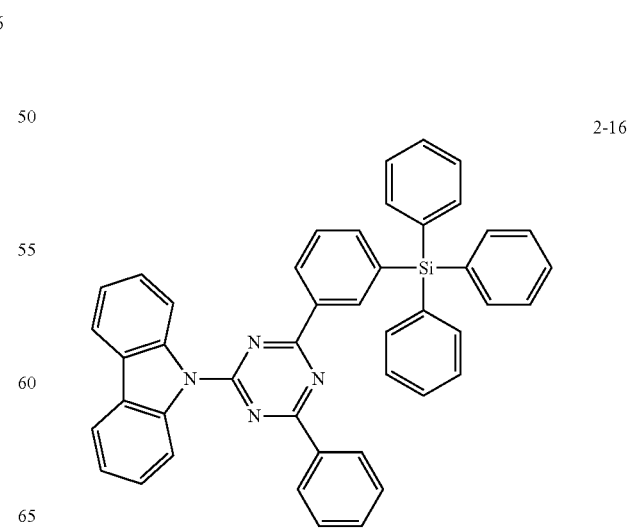

Comparative Example First Compound

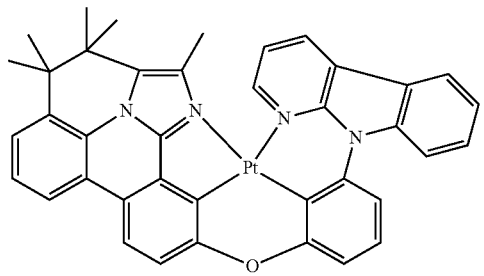

C1

TABLE 2

| Compounds | $^3$MLCT (ratio) | T1 energy level (kcal/mol) |
|---|---|---|
| Compound 1 | 11.2% | 2.70 |
| Compound 2 | 1.0% | 2.69 |
| Compound 6 | 12.0% | 2.66 |
| Comparative Example Compound C1 | 10.3% | 2.61 |

Table 2 above shows MLCT ratio values and T1 energy levels of Example and Comparative Example Compounds. As used herein, the term "MLCT ratio" refers to triplet Metal to Ligand Charge Transfer ($^3$MLCT) ratio, which shows a relative ratio on the basis of the case where 100% charge is transferred from a metal atom to a ligand. Referring to the results of Table 2, the MLCT values of Compounds 1, 2, and 6 which are Example Compounds are 11% or more, which are higher than 10.3% of the MLCT value of Comparative Compound C1. Therefore, the organometallic compound made according to some exemplary embodiments of the invention may exhibit a high MLCT ratio, thereby making a contribution to the improvement of efficiency of the organic electroluminescence device when the organometallic compound is used as an emission layer material.

In addition, the T1 energy levels of Example Compounds 1, 2, and 6 are 2.66 kcal/mol or more, which are higher than 2.61 kcal/mol of the Ti energy level of Comparative Example Compound C1.

Thus, Example Compounds include a substituent, although not wanting to be bound by theory, causing a steric hindrance to reduce intermolecular interaction, and have higher the bonding force between a metal and a ligand and the stability of molecule than those of Comparative Example Compounds, and it was discovered that when Example Compounds are applied to a light emitting device, device life time may be increased.

3. Manufacture and Evaluation of Organic Electroluminescence Device Including

Organometallic Compound

Manufacture of Organic Electroluminescence Device

The organic electroluminescence device constructed according to the principles and some exemplary embodiments of the invention including the organometallic compound in the emission layer was manufactured as follows.

An ITO having a thickness of about 1,500 Å was patterned on a glass substrate, washed with ultrapure water, and UV ozone-treated for about 10 minutes. Then, Compound HT1 was deposited on the glass substrate to a thickness of about 115 Å, and Compound 3 was deposited on the glass substrate to a thickness of about 500 Å to form a hole transport region. Next, when forming an emission layer, an organometallic compound of an Example or Comparative Example, a first host, and a second host were co-deposited in a ratio of 7:3:1 to form a 300 Å-thick layer. That is, each of the emission layers formed by co-depositing was deposited by mixing Compound 1, Compound 1-3 and Compound 2-16 in Example 1, by mixing Compound 2, Compound 1-3 and Compound 2-16 in Example 2, by mixing Compound 6, Compound 1-3 and Compound 2-16 in Example 3, and by mixing Compound 1, Compound 1-3 and Compound 2-13 in Example 4. The emission layer formed by co-depositing was deposited by mixing Compound C1, Compound 1-3, and Compound 2-16 in Comparative Example.

After the formation of the emission layer, Compound ET1 was used to form a 500 Å-thick layer. Then, Compound ET2 and Liq were co-deposited in a ratio of 1:1 to form a 200 Å-thick layer, and a 20 Å-thick layer was formed with Liq to form an electron transport region. Then, magnesium and aluminum were co-deposited in a ratio of 1:9 to form a 100 Å-thick second electrode.

In the Examples, the hole transport region, the emission layer, the electron transport region, and the second electrode were formed using a vacuum deposition apparatus.

Compound Used in Light Emitting Device

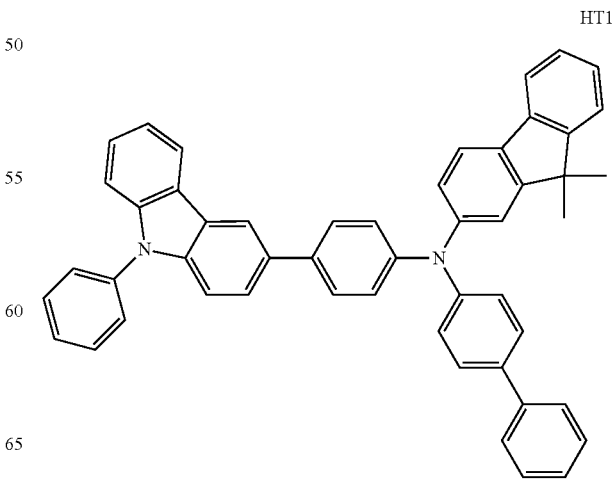

HT1

-continued

ET1

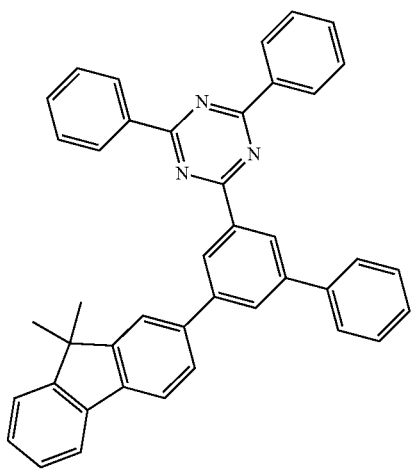

ET2

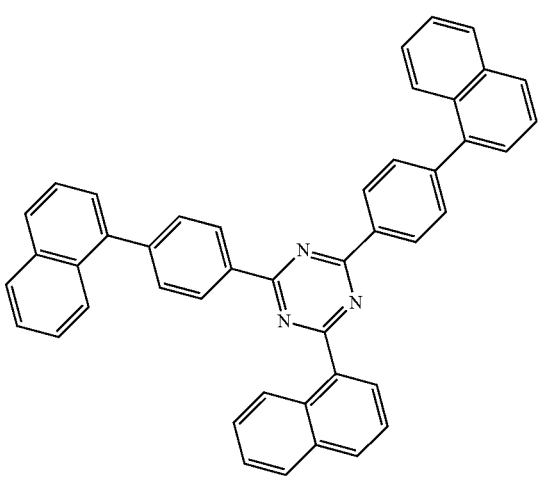

Evaluation of Organic Electroluminescence Device Characteristics

Evaluation results of the organic electroluminescence device of Examples 1 to 4 and Comparative Example 1 are listed in Table 3.

TABLE 3

| Device characteristics | Drive voltage (V) | Life time (%) |
|---|---|---|
| Example 1 | 4.3 | 130 |
| Example 2 | 4.3 | 136 |
| Example 3 | 4.4 | 133 |
| Example 4 | 4.2 | 125 |
| Comparative Example 1 | 4.5 | 100 |

Life time and drive voltage of the manufactured organic electroluminescence devices are listed in Table 3 for comparison. The life times of the devices in Examples 1 to 4 are described when the life time of the device in Comparative Example 1 is considered 100%. Referring to the results of Table 3, the organic electroluminescence devices in Examples 1 to 4 have significantly and unexpectedly lower drive voltage and significantly and unexpectedly increased life times compared to the organic electroluminescence device in Comparative Example 1.

Referring to the evaluation results of Example Compounds and Examples of the organic electroluminescence devices, although not wanting to be bound by theory, the organometallic compound according to some exemplary embodiments includes a substituent causing a steric hindrance so that intermolecular interaction may be reduced and the stability of molecule may be increased. In addition, when the organometallic compound of some exemplary embodiments is applied to the emission layer, the exciton quenching mechanism is suppressed in the emission layer, and thus significantly and unexpectedly high efficiency and significantly and unexpectedly long life time characteristics of the light emitting device may be improved.

The organic electroluminescence devices constructed according to the principles of and exemplary implementations of the invention may have low drive voltage and increased life time characteristics. The organometallic compound may be applied to an emission layer of the organic electroluminescence device to contribute to a decrease in drive voltage and an increase in life time of the organic electroluminescence device.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. An organic electroluminescence device comprising:
a first electrode;
a second electrode facing the first electrode; and
a plurality of organic layers disposed between the first electrode and the second electrode,
wherein at least one organic layer of the plurality of organic layers comprises a first compound represented by Formula 1, a second compound represented by Formula 2, and a third compound represented by Formula 3:

Formula 1

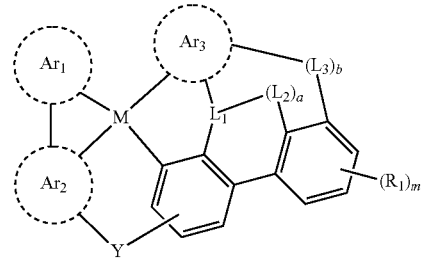

wherein, in Formula 1,
M is Pt, Au, Pd, Cu, or Ag,
Y is O or S,
$Ar_1$, $Ar_2$, and $Ar_3$ are each, independently from one another, a substituted or unsubstituted aromatic hydrocarbon group of 6 to 30 ring-forming carbon atoms, or a substituted or unsubstituted aromatic heterocycle of 2 to 30 ring-forming carbon atoms, and $Ar_1$ comprises, as a substituent, an aryl group substituted with at least one of a hydrogen atom, a deuterium atom, a substituted or unsubstituted alkyl group, a cyano group, a substituted or unsubstituted aryl group, a substituted or unsubstituted alkyl group, and a substituted borazine group, $L_1$ is a direct linkage or N, $L_2$ is a direct linkage, $L_3$ is a substituted or unsubstituted alkylene group having 1 to 30 carbon atoms, a is 0 or 1, b is an integer of 0 to 2, $R_1$ is a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, and m is an integer of 0 to 4,

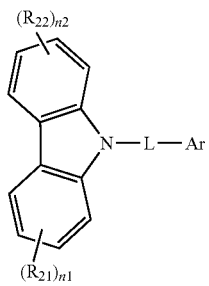

Formula 2 wherein, in Formula 2,

Ar is a substituted or unsubstituted silyl group, a substituted or unsubstituted aryl group of 6 to 30 ring-forming carbon atoms, or a substituted or unsubstituted heteroaryl group of 3 to 30 ring-forming carbon atoms, L is a direct linkage, a substituted or unsubstituted arylene group having 6 to 30 ring-forming carbon atoms, or a substituted or unsubstituted heteroarylene group having 3 to 30 ring-forming carbon atoms, $R_{21}$ and $R_{22}$ are each, independently from one another, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and n1 and n2 are each, independently from one another, an integer of 0 to 4,

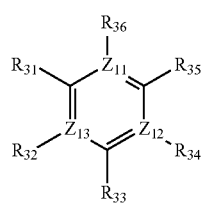

Formula 3 wherein, in Formula 3, $R_{31}$, $R_{32}$, $R_{33}$, $R_{34}$, $R_{35}$, and $R_{36}$ are each, independently from one another, a hydrogen atom, a deuterium atom, a cyano group, a substituted silyl group, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and $Z_{11}$, $Z_{12}$, and $Z_{13}$ are each, independently from one another, C or N.

2. The organic electroluminescence device of claim 1, wherein the first compound is represented by Formula 1-1a or Formula 1-1b:

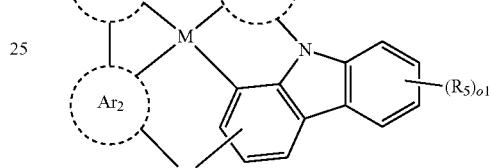

Formula 1-1a

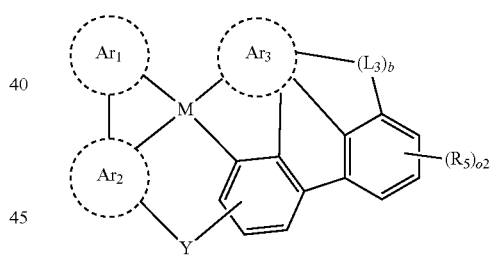

Formula 1-1b wherein, in Formula 1-1a and Formula 1-1b, $R_5$ and $R_6$ are each, independently from one another, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, o1 is an integer of 0 to 4, o2 is an integer of 0 to 3, and in Formula 1-1a and Formula 1-1b, M, $Ar_1$ to $Ar_3$, Y, $L_3$, and b have, independently from one another, the same meanings as defined in Formula 1.

3. The organic electroluminescence device of claim 1, wherein the first compound is represented by Formula 1-2a or Formula 1-2b:

Formula 1-2a

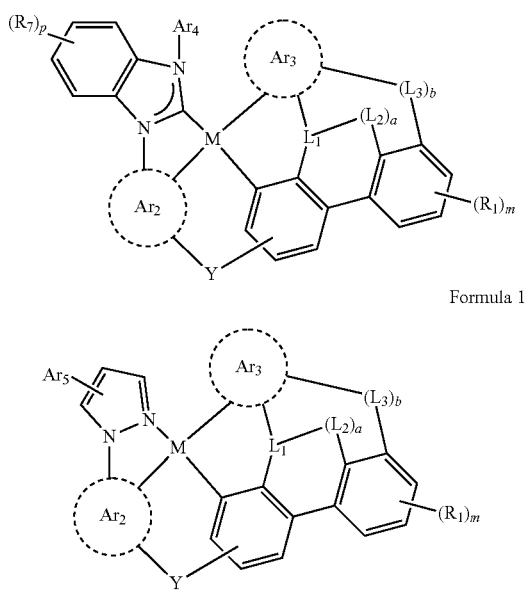

Formula 1-2b wherein, in Formula 1-2a and 1-2b,

R$_7$ is a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, p is an integer of 0 to 4, Ar$_4$ and Ar$_5$ are each, independently from one another, represented by Formula S1 to Formula S3:

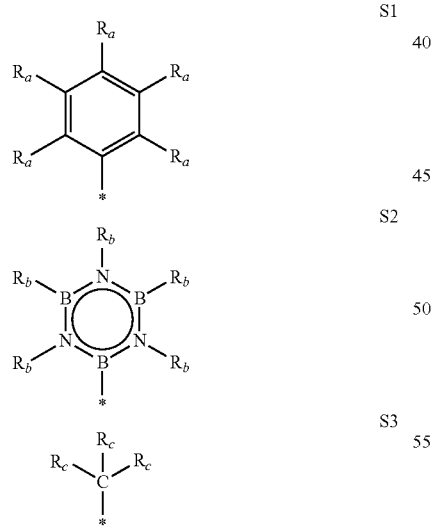

wherein, in Formula S1 to Formula S3,

R$_a$, R$_b$, and R$_c$ are each, independently from one another, a hydrogen atom, a deuterium atom, a substituted or unsubstituted alkyl group having 1 to 30 carbon atoms, a cyano group, and a substituted or unsubstituted aryl group having 6 to 30 ring-forming carbon atoms, or are bonded to an adjacent group to form a ring, and in Formulae 1-2a and 1-2b, M, Y, Ar$_2$, Ar$_3$, L$_1$ to L$_3$, a, b, R$_1$, and m have, independently from one another, the same meanings as defined in Formula 1.

4. The organic electroluminescence device of claim 1, wherein the first compound is represented by Formula 1-3a or Formula 1-3b:

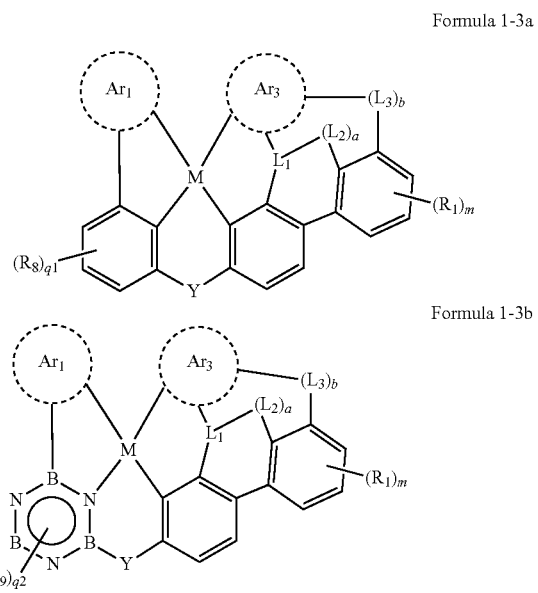

wherein, in Formula 1-3a and Formula 1-3b,

R$_8$ and R$_9$ are each, independently from one another, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, q1 and q2 are each, independently from one another, an integer of 0 to 3, and in Formulae 1-3a and 1-3b, M, Y, Ar$_1$ to Ar$_3$, L$_1$ to L$_3$, a, b, R$_1$, and m have, independently from one another, the same meanings as defined in Formula 1.

5. The organic electroluminescence device of claim 1, wherein the first compound is represented by Formula 1-4a or Formula 1-4b:

Formula 1-4a

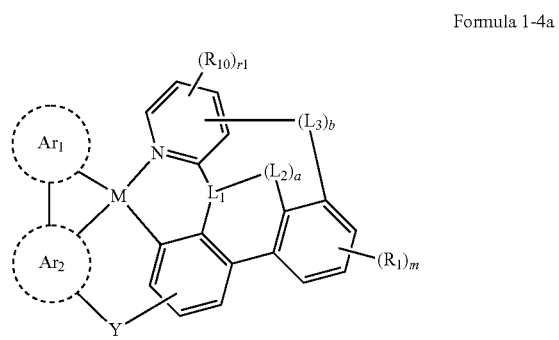

-continued

Formula 1-4b

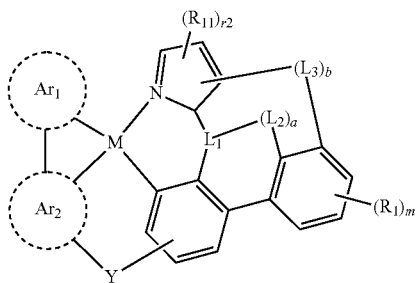

wherein, in Formula 1-4a and Formula 1-4b,
$R_{10}$ and $R_{11}$ are each, independently from one another, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring,
r1 is an integer of 0 to 3,
r2 is an integer of 0 to 2, and
in Formulae 1-4a and 1-4b, M, Y, $Ar_1$, $Ar_2$, $L_1$ to $L_3$, a, b, $R_1$, and m have, independently from one another, the same meanings as defined in Formula 1.

6. The organic electroluminescence device of claim 1, wherein the first compound is represented by Formula 1-5:

Formula 1-5

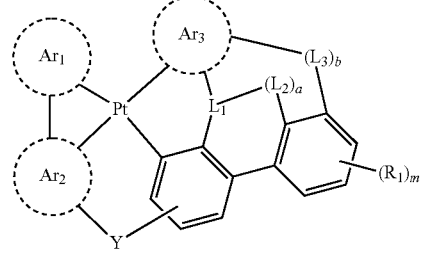

wherein, in Formula 1-5,
Y, $Ar_1$ to $Ar_3$, $L_1$ to $L_3$, a, b, $R_1$, and m have, independently from one another, the same meanings as defined in Formula 1.

7. The organic electroluminescence device of claim 1, wherein the first compound is represented by Formula 1-6:

Formula 1-6

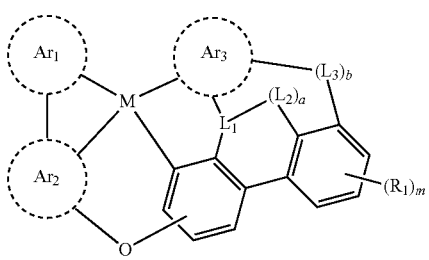

wherein, in Formula 1-6,
M, $Ar_1$ to $Ar_3$, $L_1$ to $L_3$, a, b, $R_1$, and m have, independently from one another, the same meanings as defined in Formula 1.

8. The organic electroluminescence device of claim 1, wherein the first compound is represented by either Formula 1-7a or Formula 1-7b:

Formula 1-7a

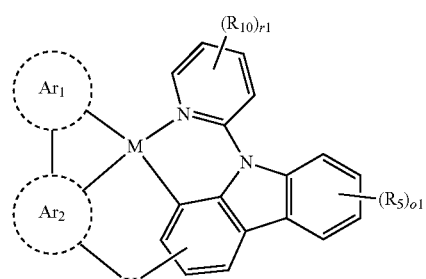

Formula 1-7b

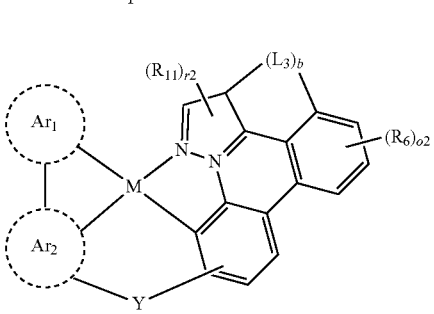

wherein, in Formula 1-7a and Formula 1-7b,
$R_5$ and $R_6$ are each, independently from one another, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring,
o1 is an integer of 0 to 4,
o2 is an integer of 0 to 3, and
$R_{10}$ and $R_{11}$ are each, independently from one another, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring,
r1 is an integer of 0 to 3,
r2 is an integer of 0 to 2, and
in Formula 1-7a and Formula 1-7b, M, $Ar_1$, $Ar_2$, Y, $L_3$, and b have, independently from one another, the same meanings as defined in Formula 1.

9. The organic electroluminescence device of claim 1, wherein the organic layers comprise a hole transport region, an emission layer, and an electron transport region, and the emission layer comprises the first to third compounds.

10. The organic electroluminescence device of claim 9, wherein the emission layer is configured to emit phosphorescence.

11. The organic electroluminescence device of claim 9, wherein the emission layer comprises a host and a dopant, and the dopant comprises the first compound.

12. The organic electroluminescence device of claim 9, wherein the hole transport region comprises a hole injection layer, a hole transport layer, an electron blocking layer, and a hole barrier reinforced layer, and the electron transport region comprises an electron injection layer, an electron transport layer, a hole blocking layer, and an electron barrier reinforced layer.

13. The organic electroluminescence device of claim 1, wherein the first compound comprises at least one compound represented by Compound Group 1:

Compound Group 1

1
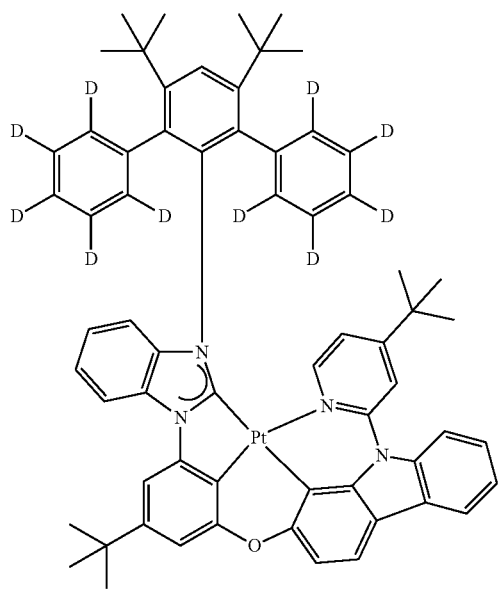

-continued

3
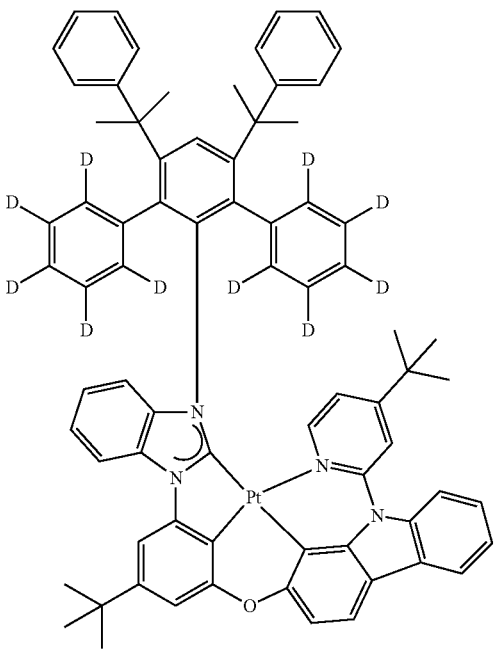

2
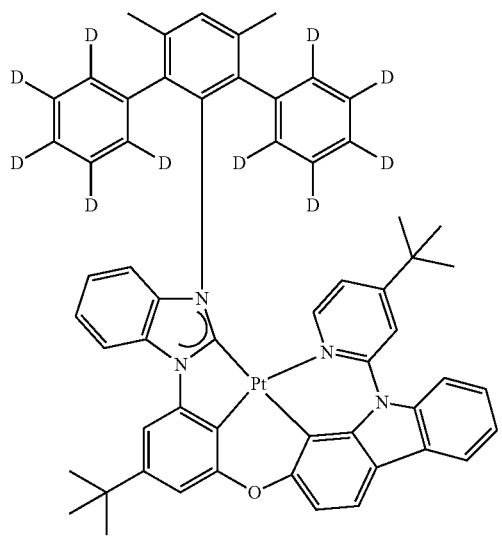

4
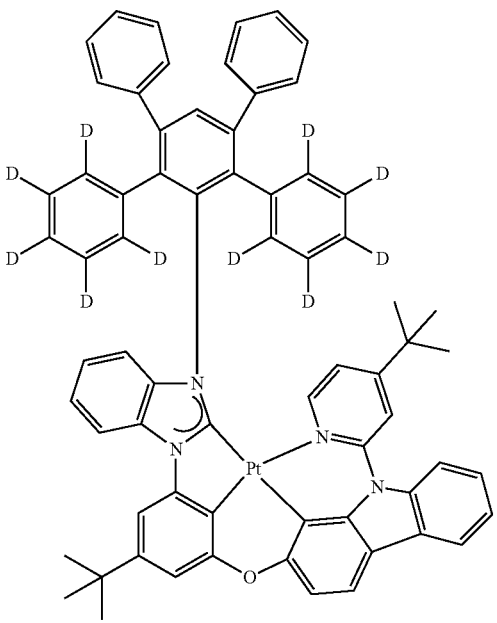

5
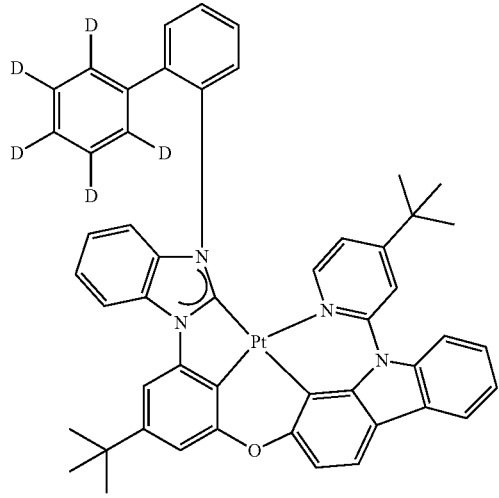
6
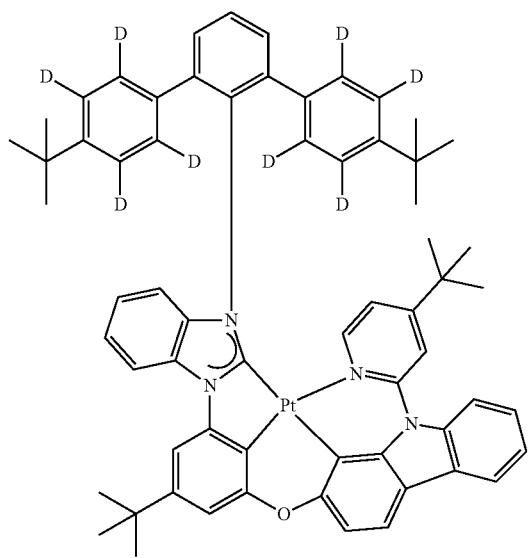
7
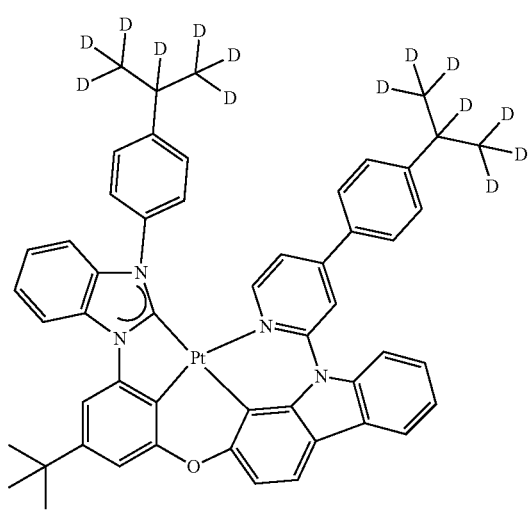
8
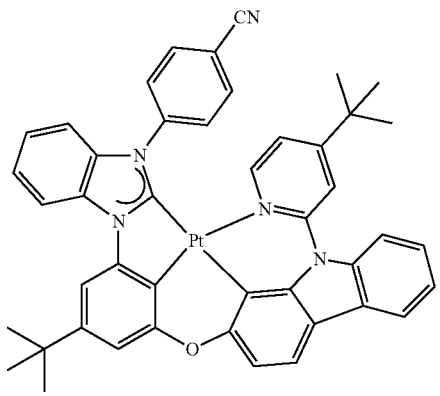
9
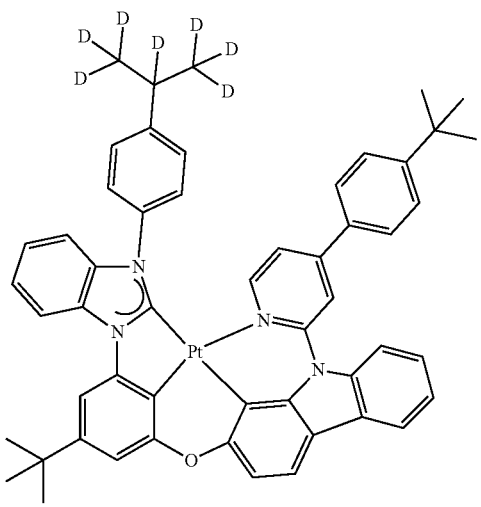
10
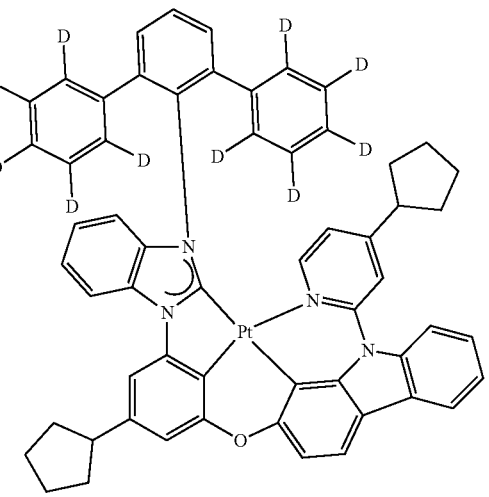

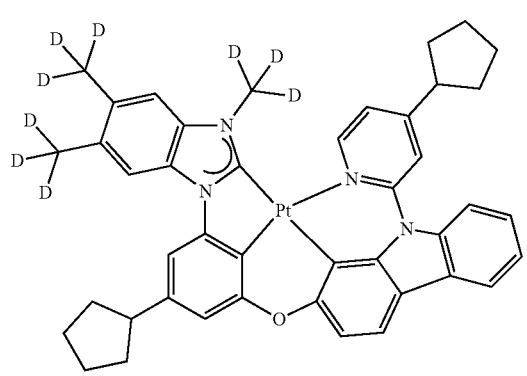
11
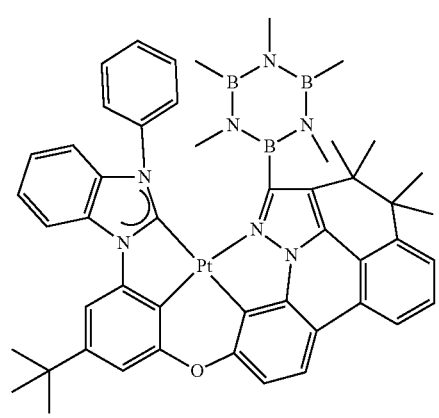
12
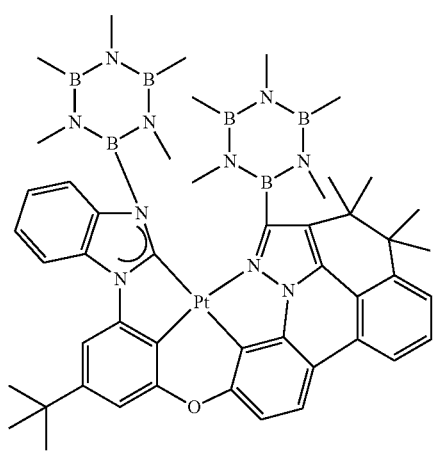
13
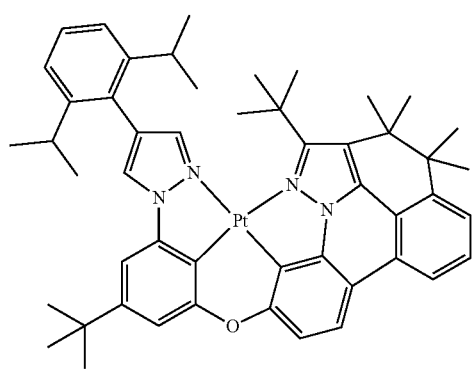
14
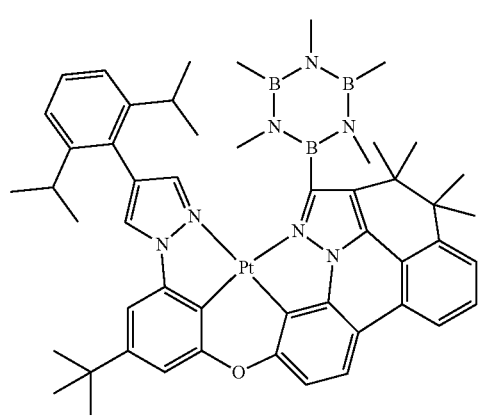
15
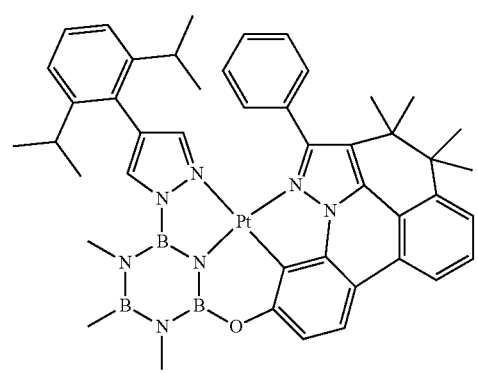
16
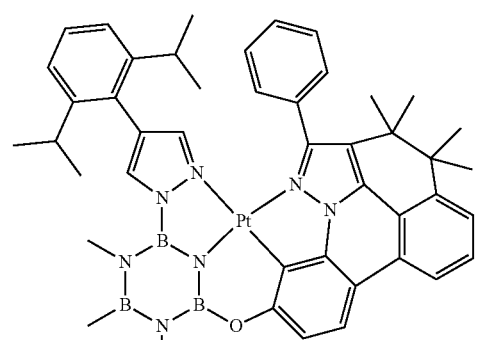
17
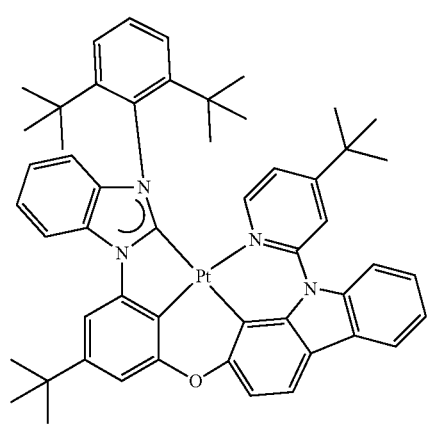
18

19
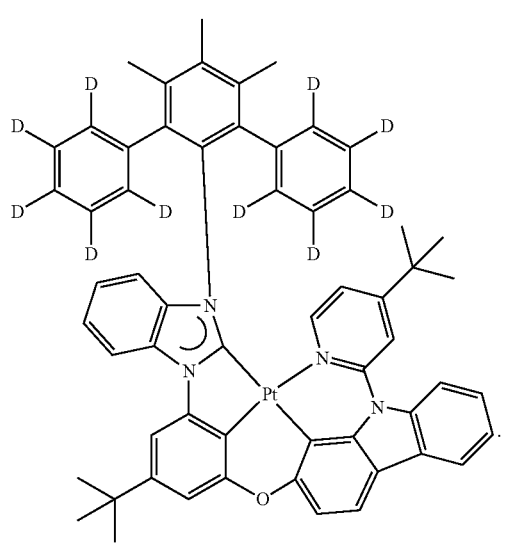
14. The organic electroluminescence device of claim 1, wherein the second compound comprises at least one compound represented by Compound Group H1:
Compound Group H1
1-1
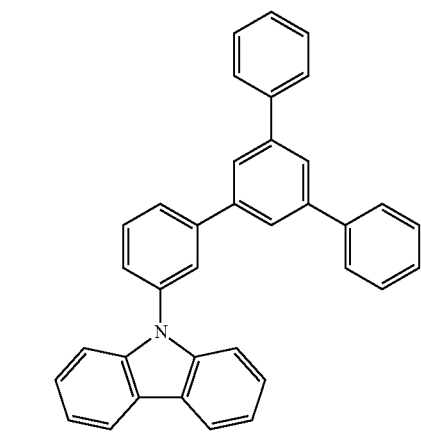
1-2
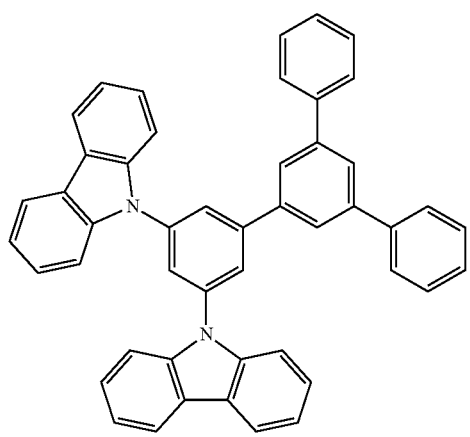
1-3
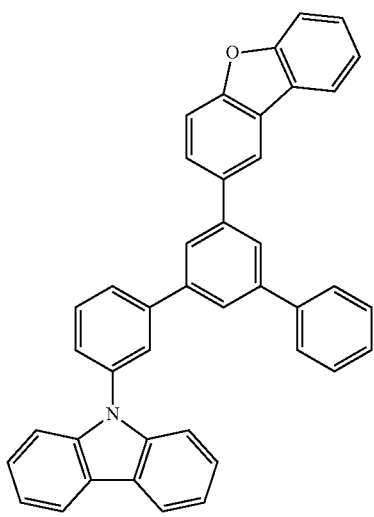
1-4
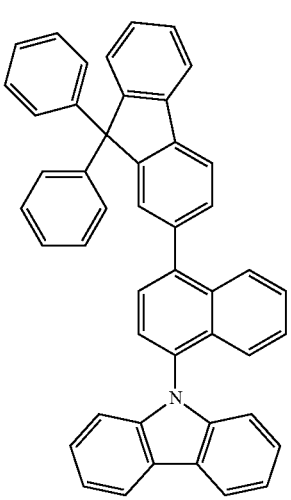
1-5
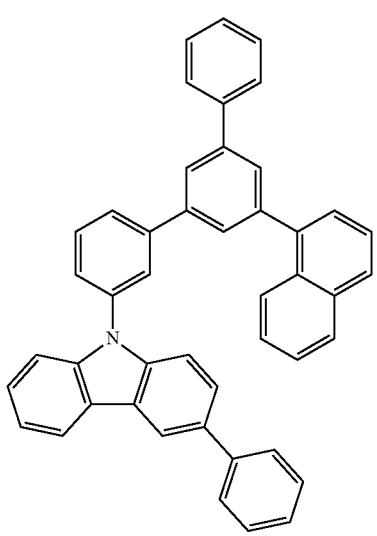

-continued
1-6
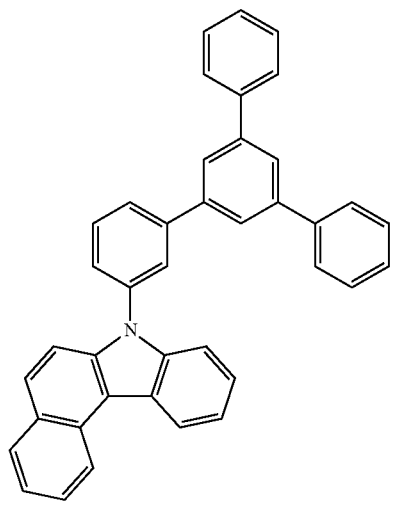
1-7
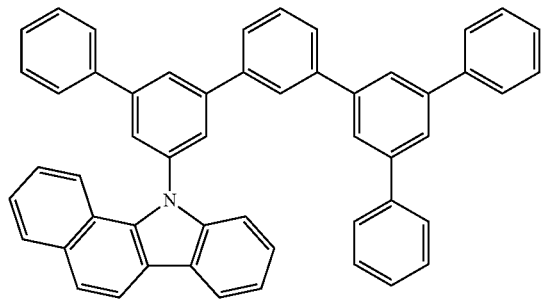
1-8
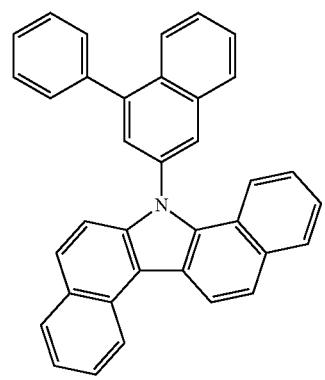
1-9
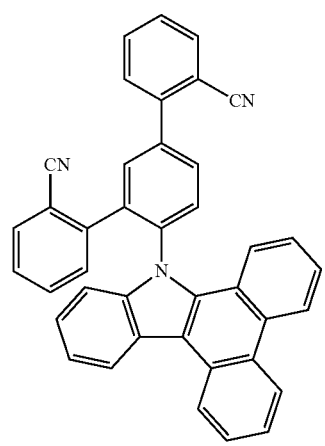
-continued
1-10
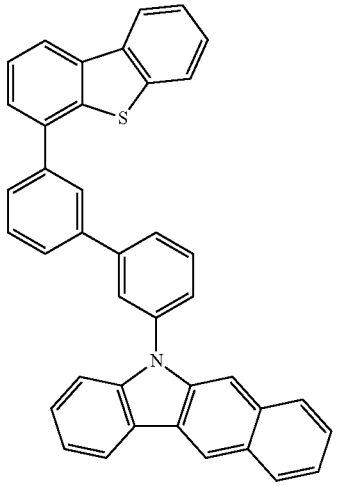
1-11
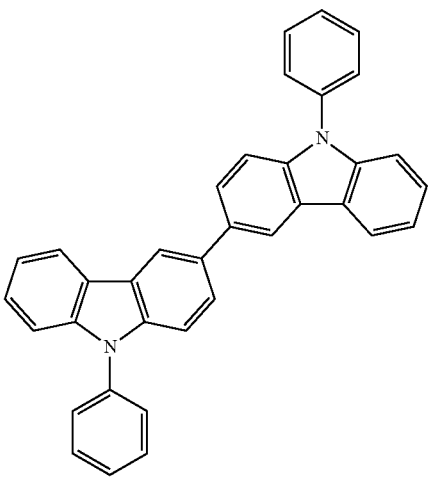
1-12
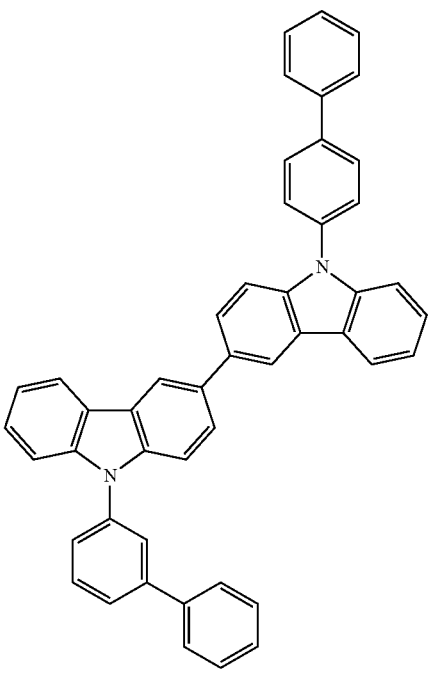

1-13
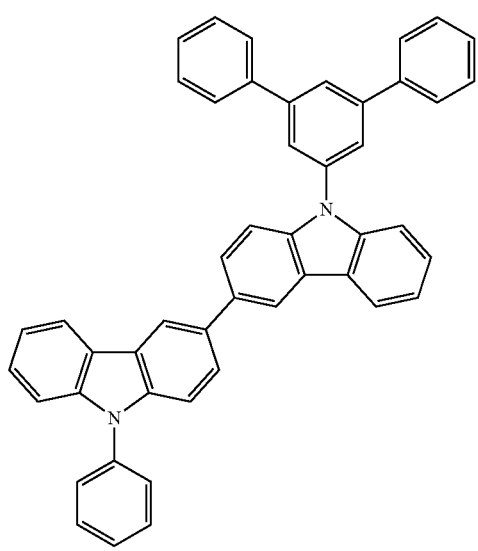
1-14
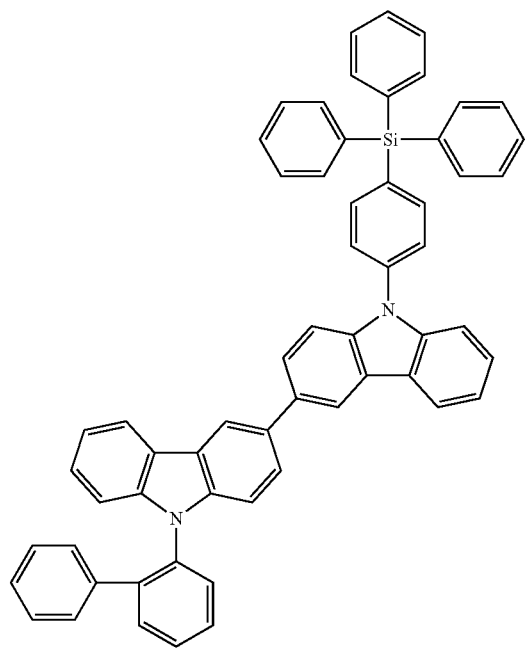
1-15
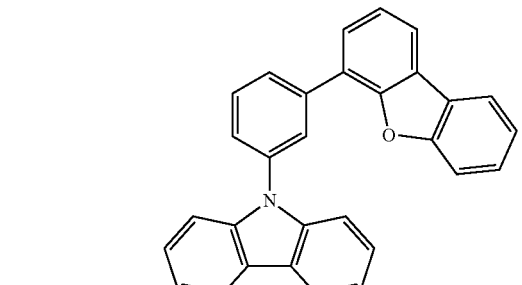
1-16
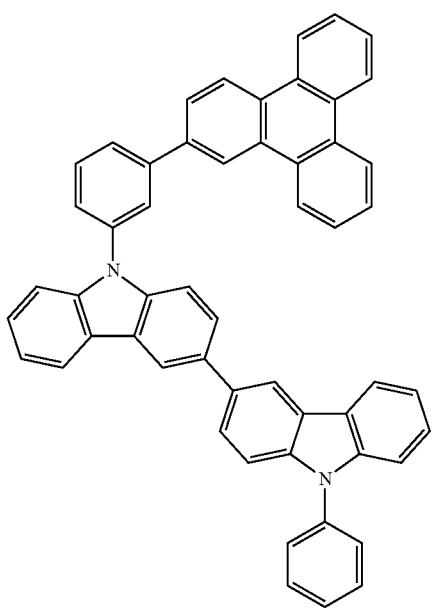
1-17
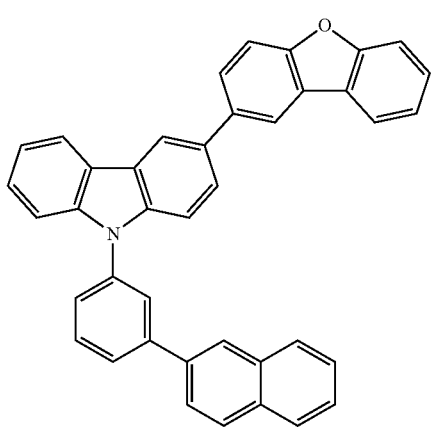

1-18
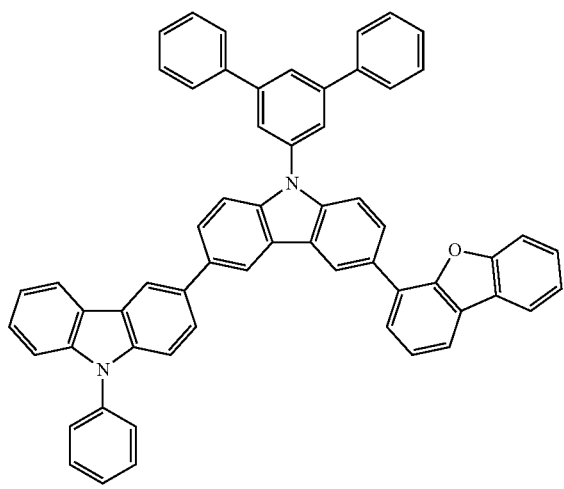
1-22
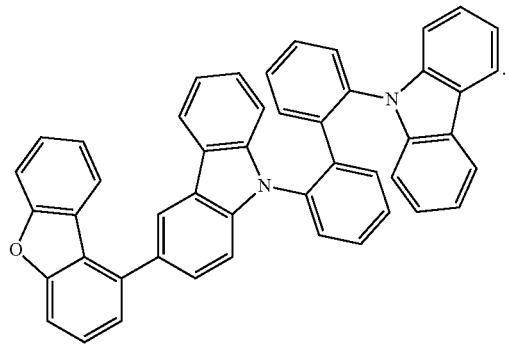
15. The organic electroluminescence device of claim 1, wherein the third compound comprises at least one compound represented by Compound Group H2:
Compound Group H2
1-19
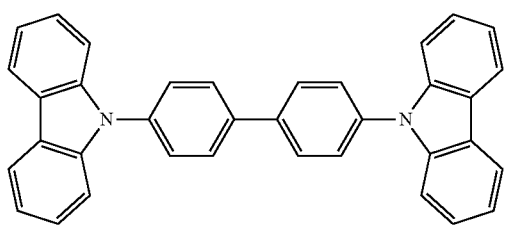
2-1
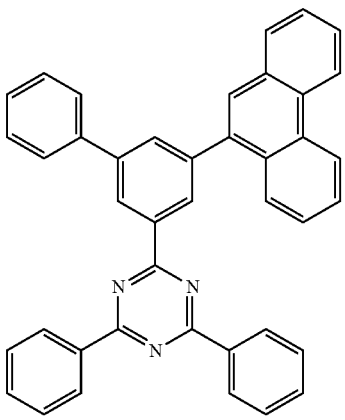
1-20
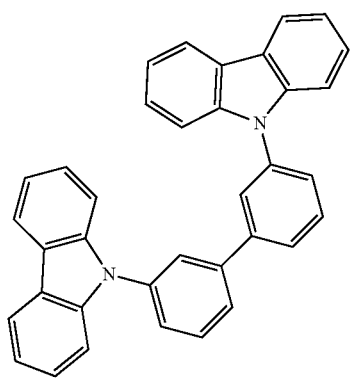
1-21
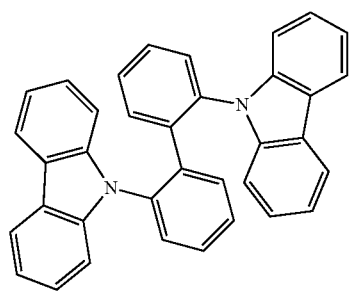
2-2
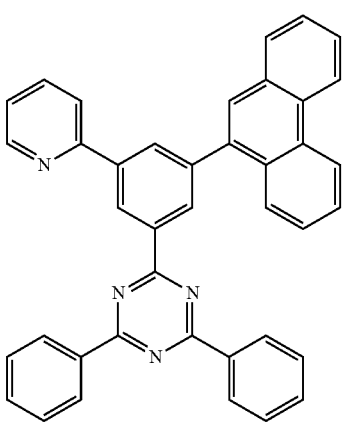

2-3
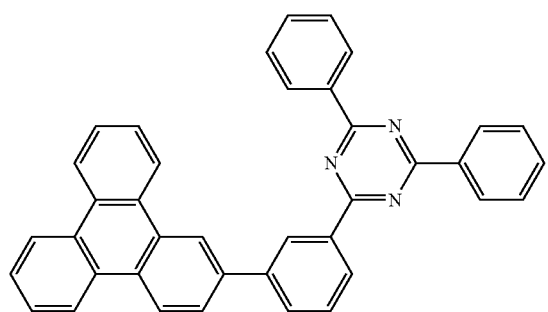
2-4
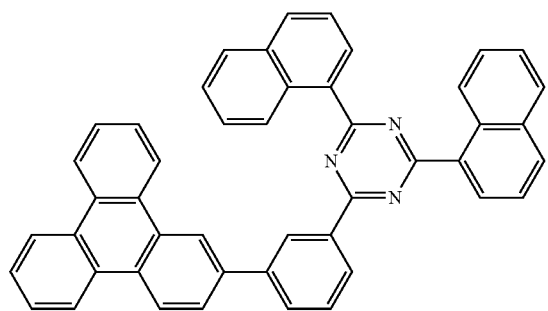
2-5
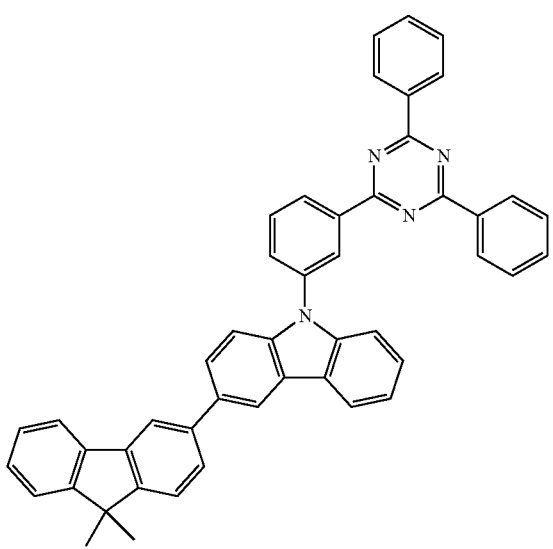
2-6
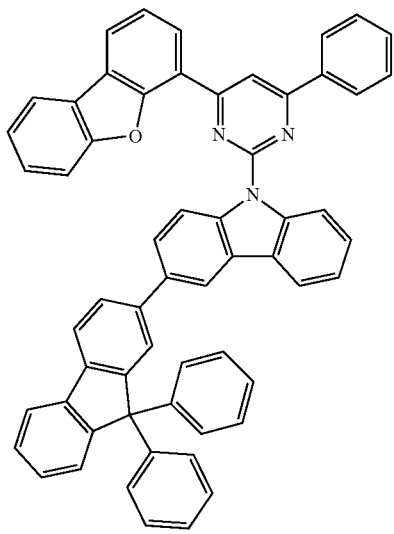
2-7
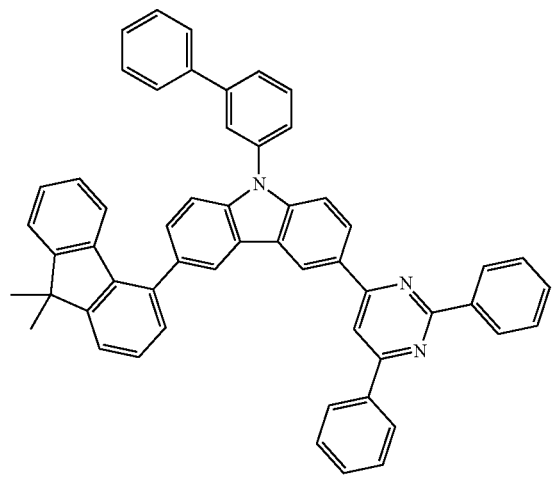
2-8
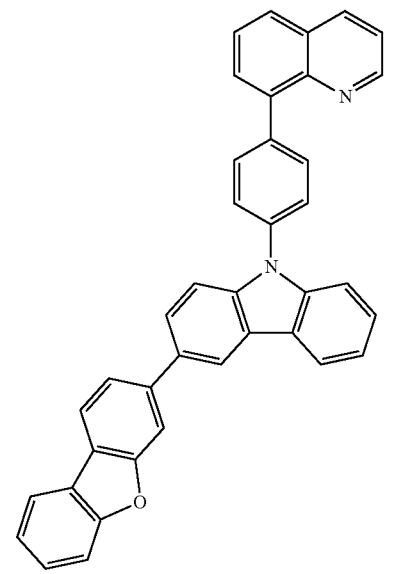

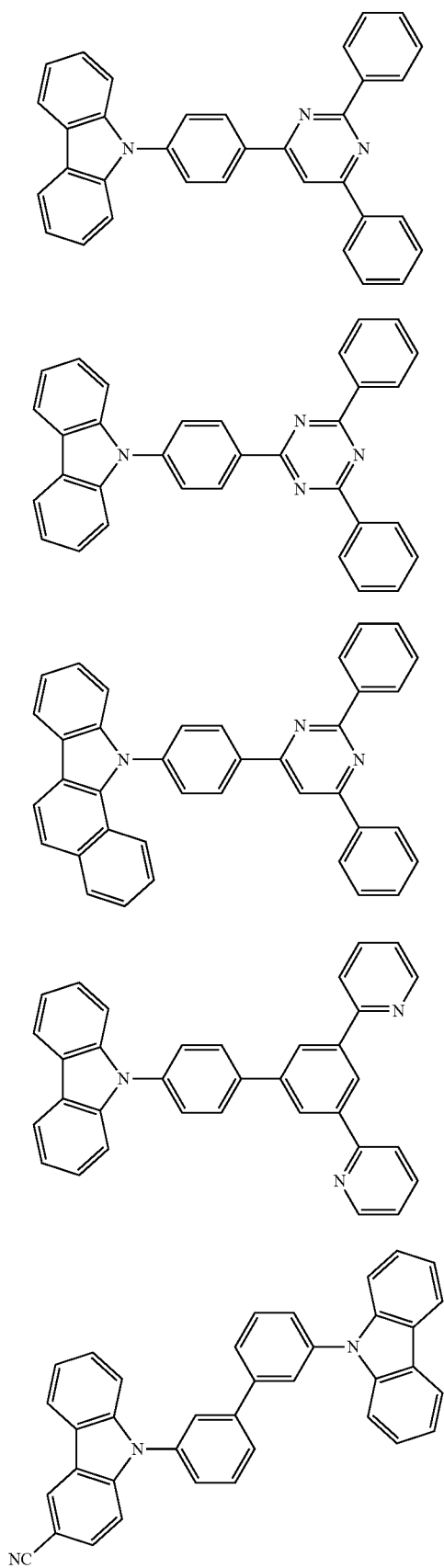
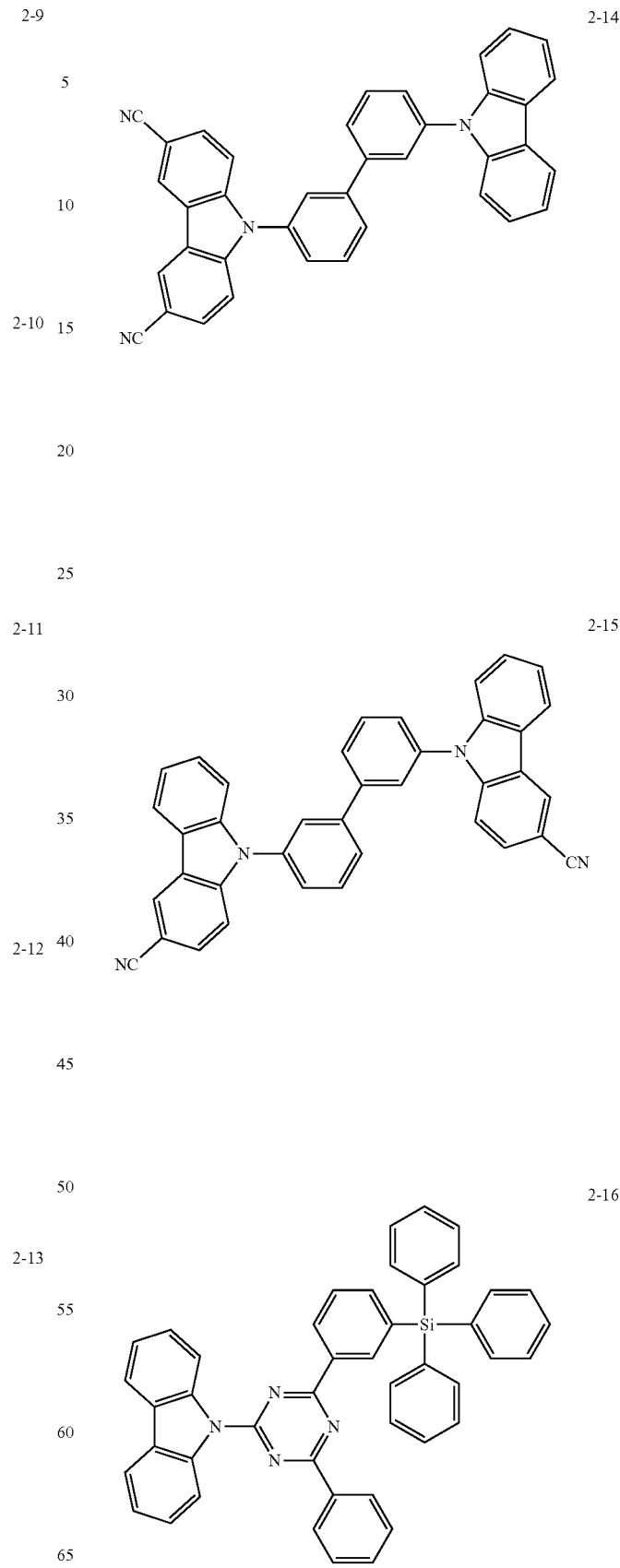

2-17
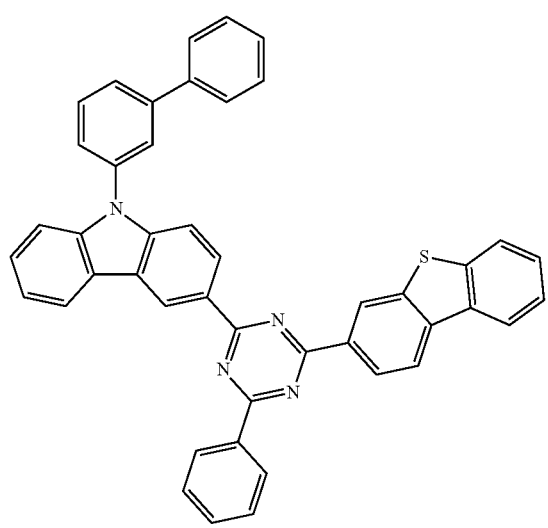
2-18
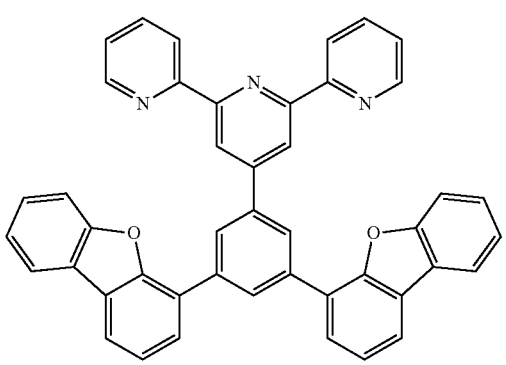
2-19
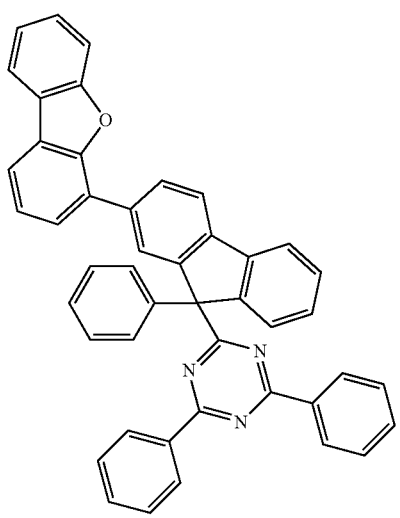
2-20
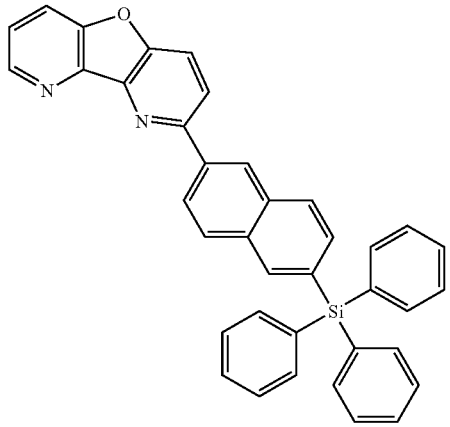
2-21
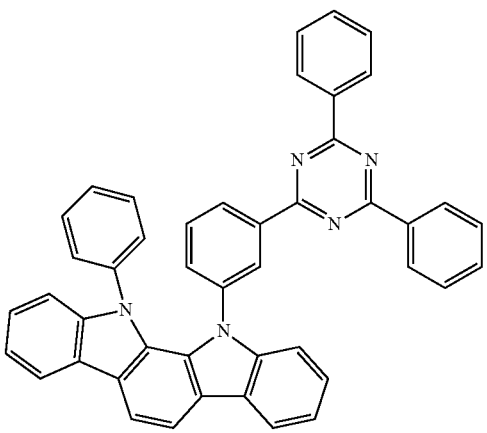
2-22
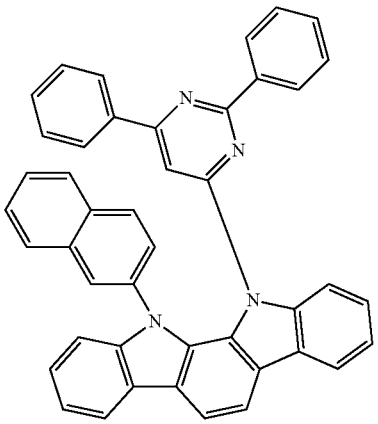

2-23
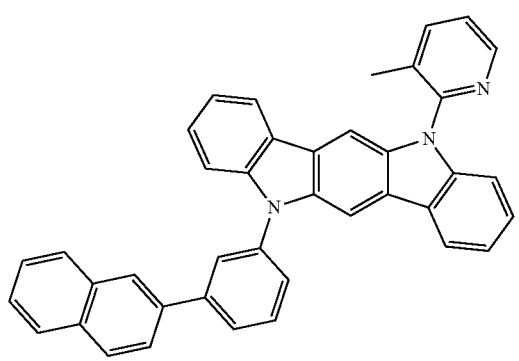
2-24
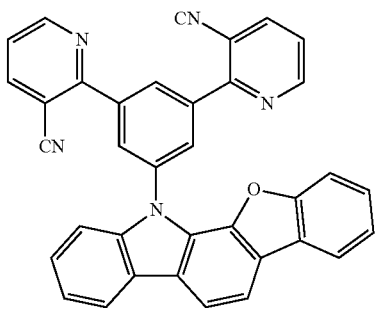
2-23
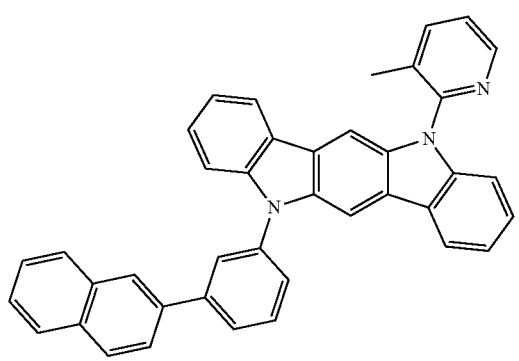
2-24
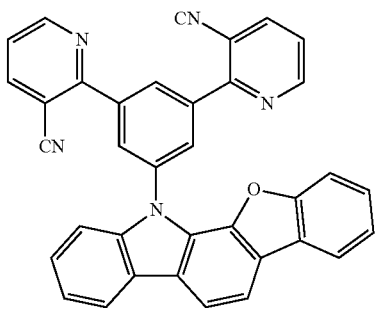
2-25
(bottom left image - not in crops list, skipping)
2-26
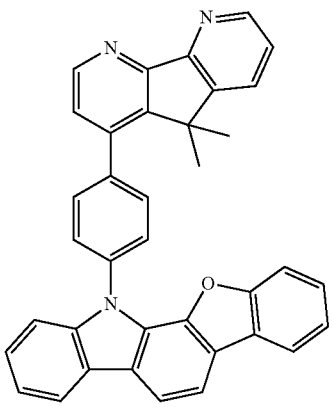
2-27
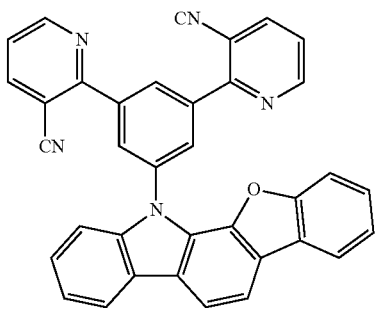
2-28
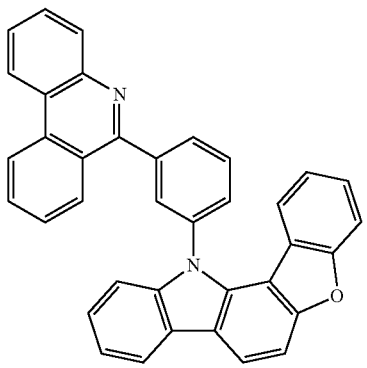
2-29
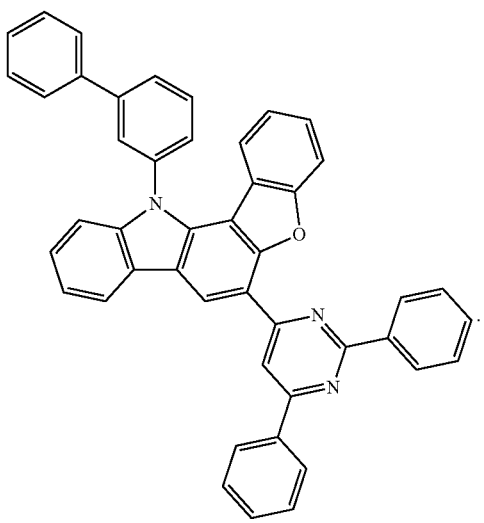

16. An organic electroluminescence device comprising:
a first electrode;
a second electrode facing the first electrode; and
a plurality of organic layers disposed between the first electrode and the second electrode,
wherein at least one organic layer of the organic layers comprises a first compound represented by Formula A or Formula B, a second compound represented by Formula 2, and a third compound represented by Formula 3:

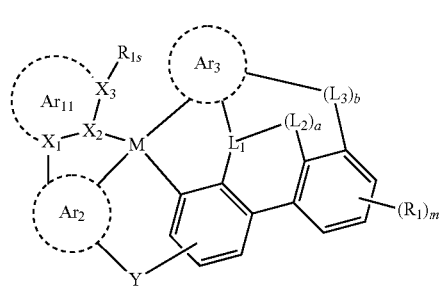

Formula A

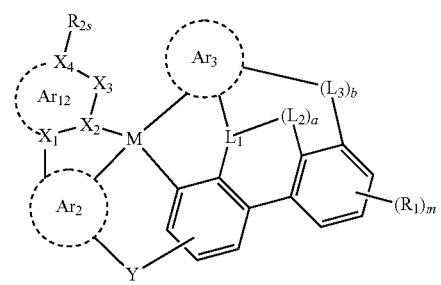

Formula B wherein, in Formula A and Formula B,

M is Pt, Au, Pd, Cu, or Ag, $Ar_{11}$, $Ar_{12}$, $Ar_2$, and $Ar_3$ are each, independently from one another, a substituted or unsubstituted aromatic hydrocarbon group of 6 to 30 ring-forming carbon atoms, or a substituted or unsubstituted aromatic heterocycle of 2 to 30 ring-forming carbon atoms, $X_1$, $X_2$, $X_3$, and $X_4$ are each, independently from one another, N or C, Y is O or S, $R_{1s}$ and $R_{2s}$ are each, independently from one another, an aryl group substituted with at least one of a hydrogen atom, a deuterium atom, a substituted or unsubstituted alkyl group, a cyano group, a substituted or unsubstituted aryl group, a substituted or unsubstituted alkyl group, and a substituted borazine group, $L_1$ is a direct linkage or N, $L_2$ is a direct linkage, $L_3$ is a substituted or unsubstituted alkylene group having 1 to 30 carbon atoms, a is 0 or 1, b is an integer of 0 to 2, $R_1$ is a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, and m is an integer of 0 to 4,

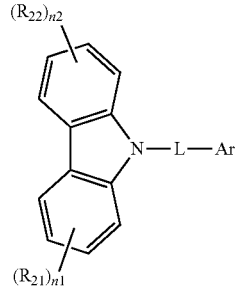

Formula 2 wherein, in Formula 2,

Ar is a substituted or unsubstituted silyl group, a substituted or unsubstituted aryl group of 6 to 30 ring-forming carbon atoms, or a substituted or unsubstituted heteroaryl group of 3 to 30 ring-forming carbon atoms, L is a direct linkage, a substituted or unsubstituted arylene group having 6 to 30 ring-forming carbon atoms, or a substituted or unsubstituted heteroarylene group having 3 to 30 ring-forming carbon atoms, $R_{21}$ and $R_{22}$ are each, independently from one another, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and n1 and n2 are each, independently from one another, an integer of 0 to 4, and

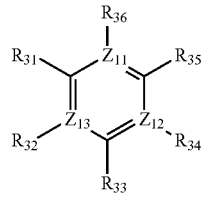

Formula 3 wherein, in Formula 3, $R_{31}$, $R_{32}$, $R_{33}$, $R_{34}$, $R_{35}$, and $R_{36}$ are each, independently from one another, a hydrogen atom, a deuterium atom, a cyano group, a substituted silyl group, a substituted or unsubstituted aryl group having 6 to 30 ring-forming carbon atoms, or a substituted or unsubstituted heteroaryl group having 3 to 30 ring-forming carbon atoms, or are bonded to an adjacent group to form a ring, and $Z_{11}$, $Z_{12}$, and $Z_{13}$ are each, independently from one another, C or N.

17. The organic electroluminescence device of claim 16, wherein $R_{1s}$ and $R_{2s}$ are, independently of one another, represented by any one of Formula S1 to Formula S3:

[S1]
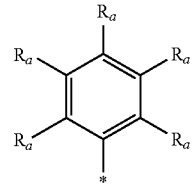

[S2]
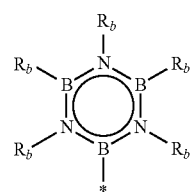

[S3]
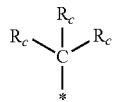

wherein, in Formula S1 to Formula S3, $R_a$, $R_b$, and $R_c$ are each, independently from one another, a hydrogen atom, a deuterium atom, a substituted or unsubstituted alkyl group having 1 to 30 carbon atoms, a cyano group, or a substituted or unsubstituted aryl group having 6 to 30 ring-forming carbon atoms, or are bonded to an adjacent group to form a ring.

18. The organic electroluminescence device of claim 16, wherein $R_{1s}$ and $R_{2s}$ comprise, independently of one another, at least one substituent represented by Group R:

Group R

RS1
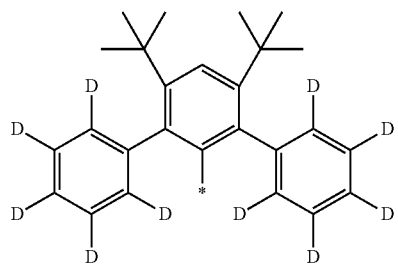

RS2
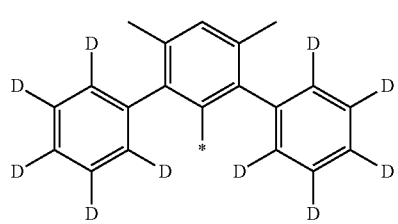

RS3
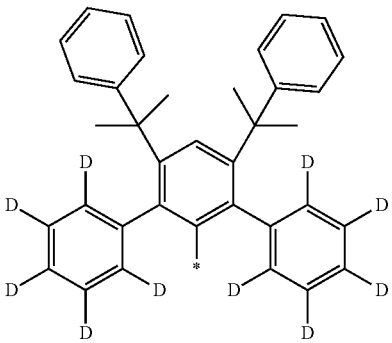

RS4
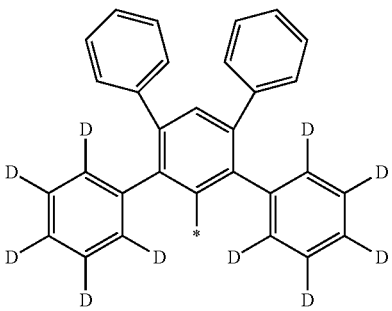

RS5
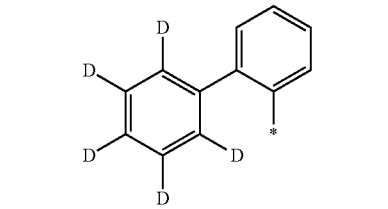

RS6
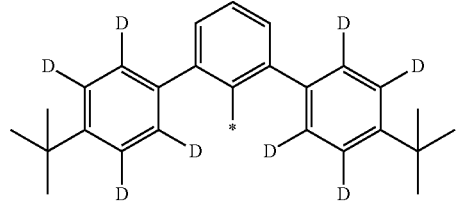

RS7
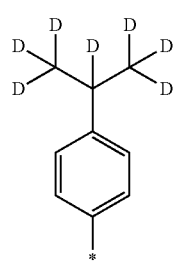

RS8
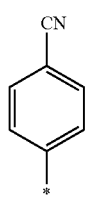

RS9

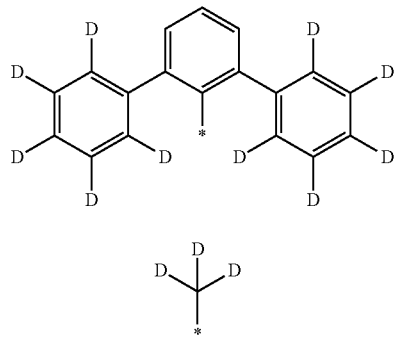

RS10

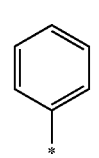

RS11

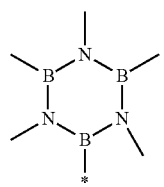

RS12

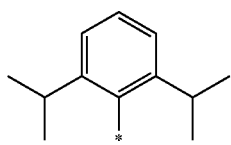

RS13

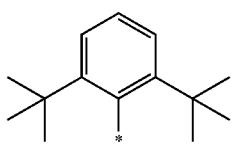

RS14

19. An organometallic compound for an organic electroluminescence device, the organometallic compound being represented by Formula A or Formula B:

Formula A

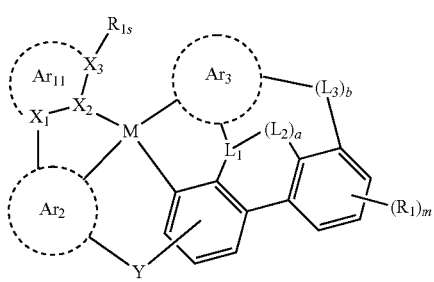

Formula B

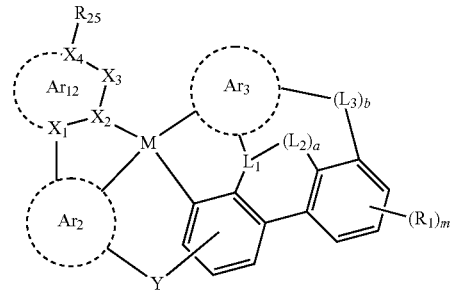

wherein, in Formula A and Formula B,

M is Pt, Au, Pd, Cu, or Ag, $Ar_{11}$, $Ar_{12}$, $Ar_2$, and $Ar_3$ are each, independently from one another, a substituted or unsubstituted aromatic hydrocarbon group of 6 to 30 ring-forming carbon atoms, or a substituted or unsubstituted aromatic heterocycle of 2 to 30 ring-forming carbon atoms, $X_1$, $X_2$, $X_3$, and $X_4$ are each, independently from one another, N or C, Y is O or S, $R_{1s}$ and $R_{2s}$ are each, independently from one another, an aryl group substituted with at least one of a hydrogen atom, a deuterium atom, a substituted or unsubstituted alkyl group, a cyano group, a substituted or unsubstituted aryl group, a substituted or unsubstituted alkyl group, and a substituted borazine group, $L_1$ is a direct linkage or N, $L_2$ is a direct linkage, $L_3$ is a substituted or unsubstituted alkylene group having 1 to 30 carbon atoms, a is 0 or 1, b is an integer of 0 to 2, $R_1$ is a direct linkage, a hydrogen atom, a deuterium atom, a substituted or unsubstituted aryl group having 6 to 30 ring-forming carbon atoms, or a substituted or unsubstituted heteroaryl group having 3 to 30 ring-forming carbon atoms, or is bonded to an adjacent group to form a ring, and m is an integer of 0 to 4.

20. The organometallic compound of claim 19, wherein the organometallic compound represented by Formula A or Formula B, independently from one another, comprises at least one compound represented by Compound Group 1:
Compound Group 1
1
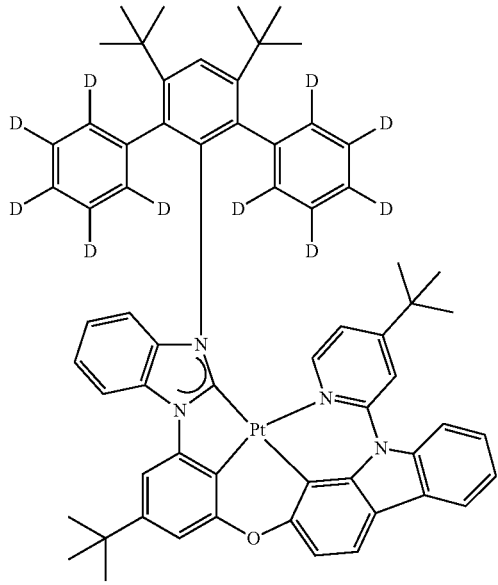
2
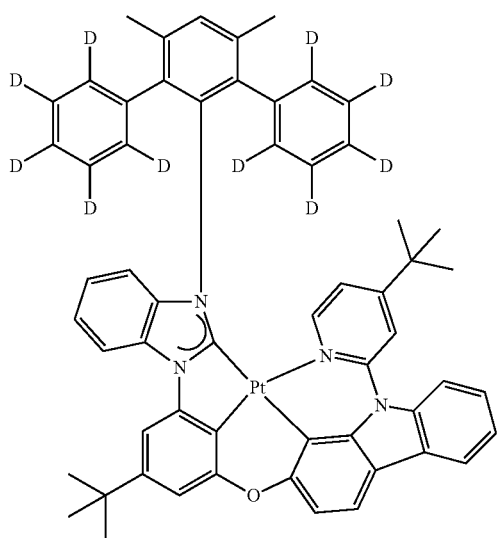
3
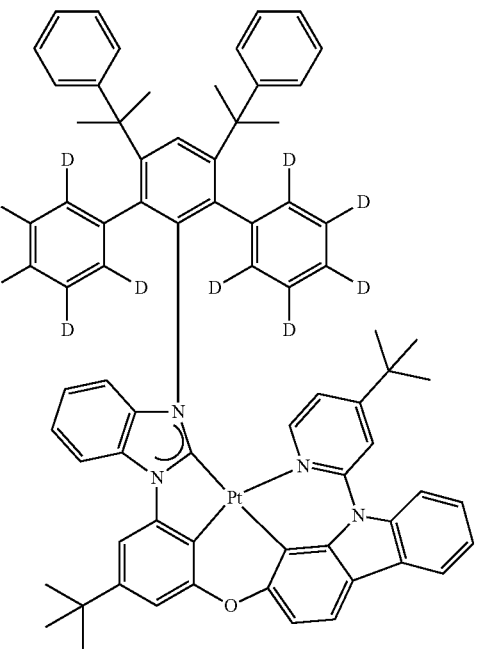
4
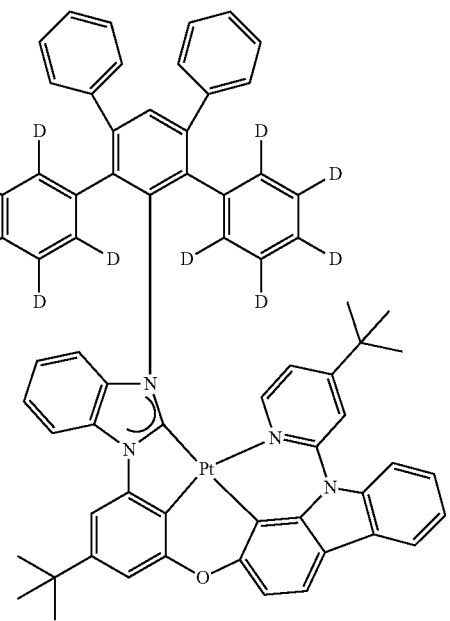

5
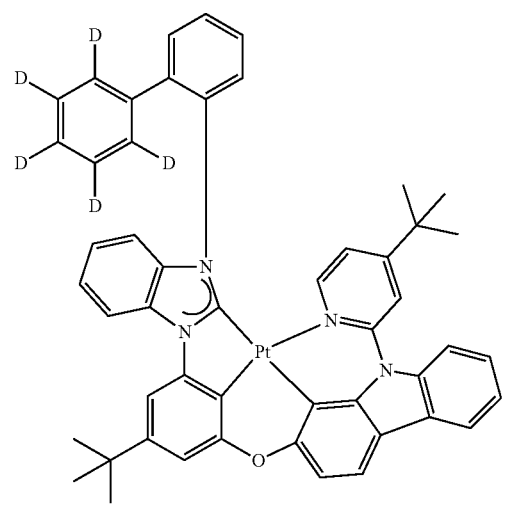
6
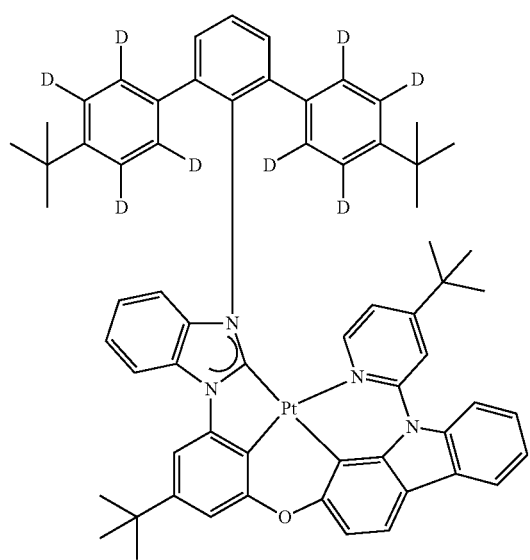
7
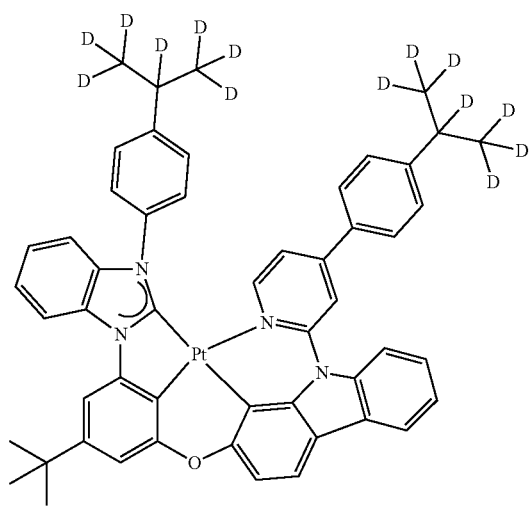
8
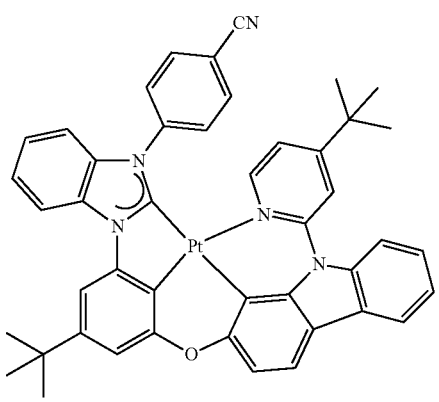
9
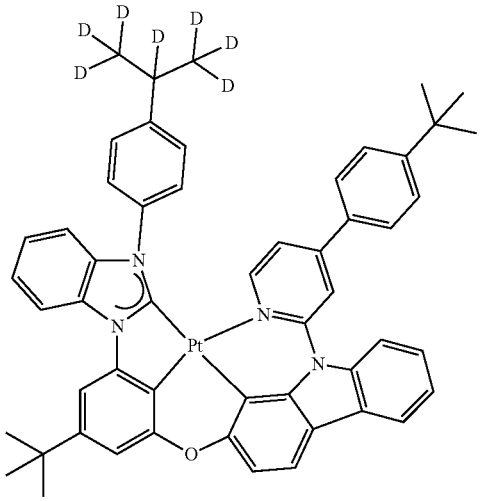
10
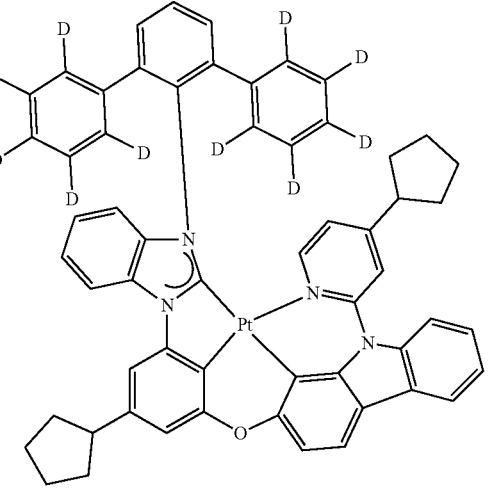

11
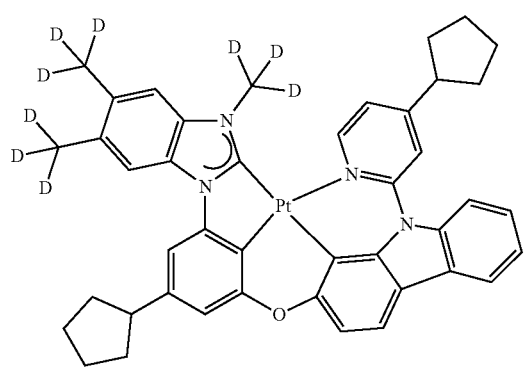
12
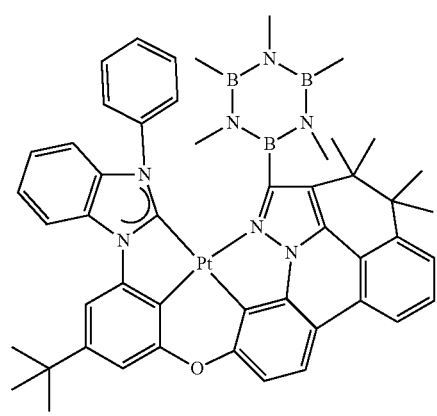
13
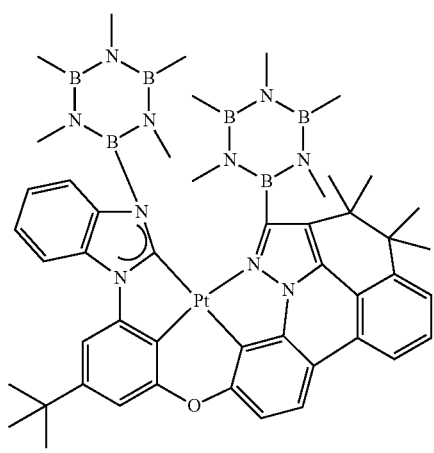
14
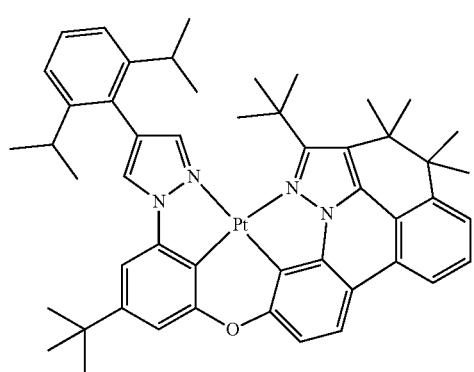
15
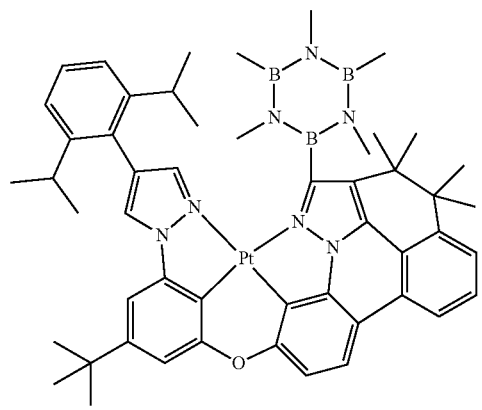
16
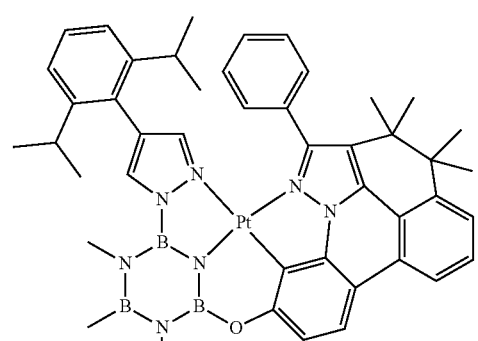
17
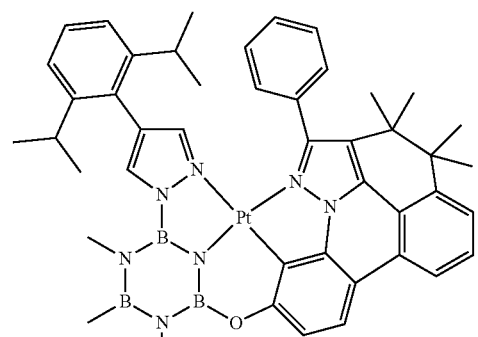
18
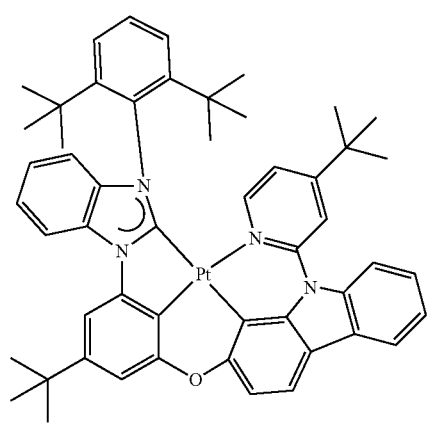

-continued
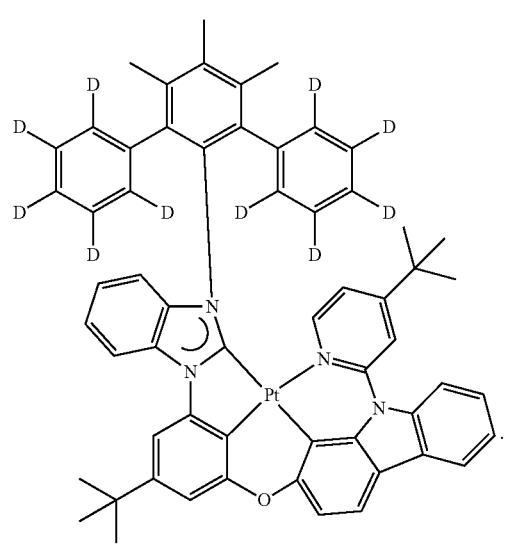
* * * * *

UNITED STATES PATENT AND TRADEMARK OFFICE
CERTIFICATE OF CORRECTION

PATENT NO. : 12,035,617 B2
APPLICATION NO. : 17/246691
DATED : July 9, 2024
INVENTOR(S) : Hyun Shin et al.

It is certified that error appears in the above-identified patent and that said Letters Patent is hereby corrected as shown below:

In the Claims

In Column 82, Lines 37-46, in Claim 2, formula 1-1b, delete "

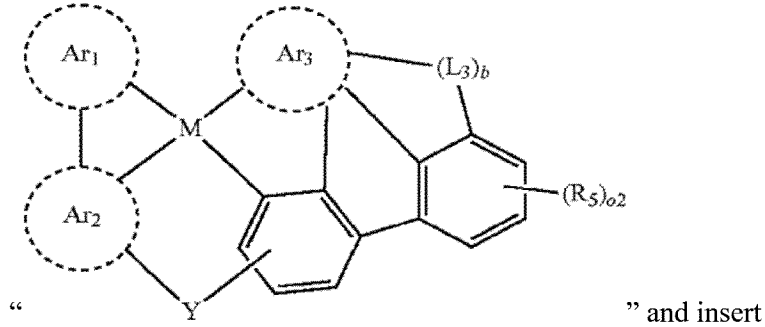

" and insert

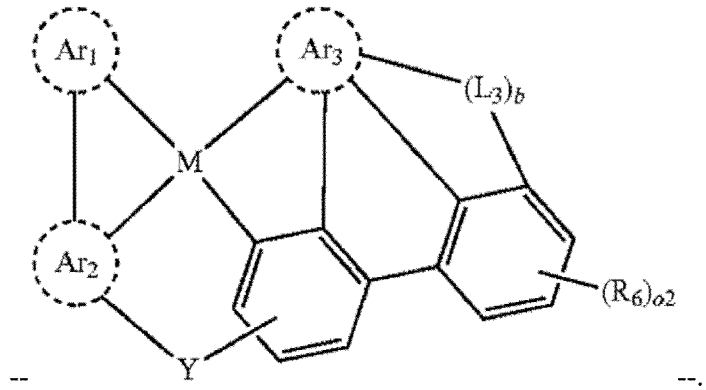

--.

Signed and Sealed this
Twenty-seventh Day of January, 2026

John A. Squires
*Director of the United States Patent and Trademark Office*

CERTIFICATE OF CORRECTION (continued)
U.S. Pat. No. 12,035,617 B2

In Column 85, Lines 3-14, in Claim 5, formula 1-4b, delete

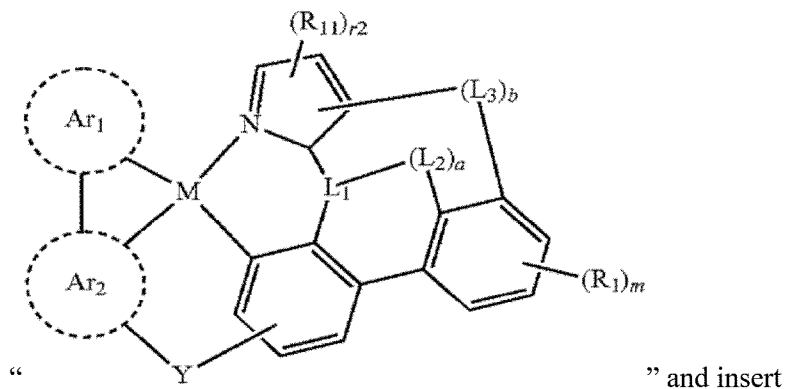

" and insert

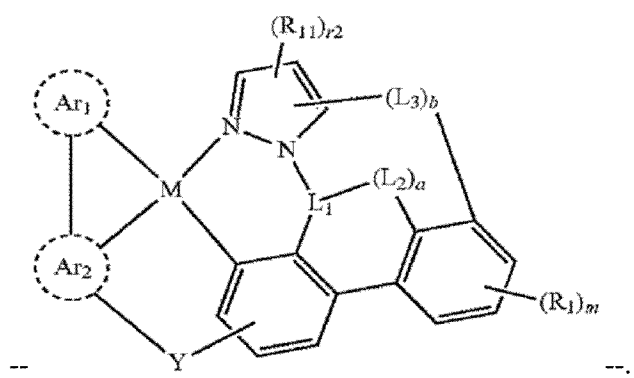

-- --.

In Column 108, Lines 18-29, in Claim 15, compound 2-27, delete

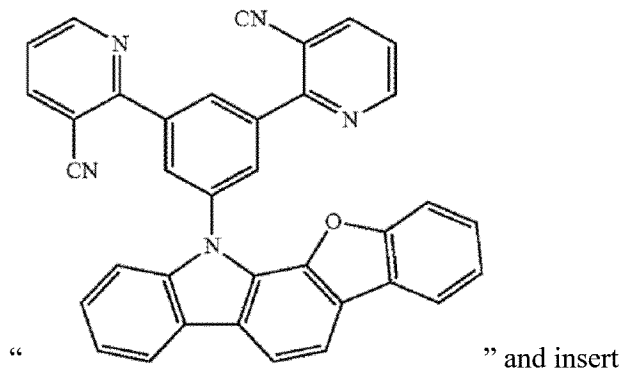

" and insert

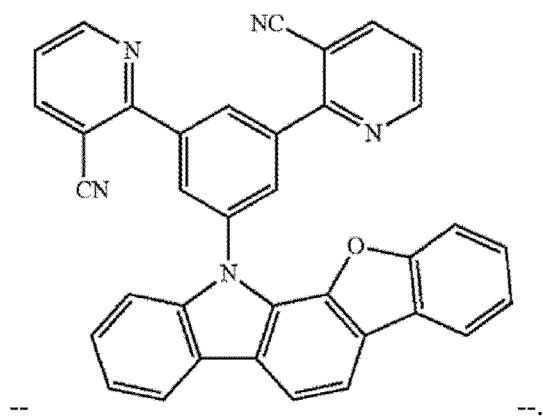

-- --.